United States Patent
Subauste et al.

(10) Patent No.: US 12,319,726 B2
(45) Date of Patent: *Jun. 3, 2025

(54) METHOD FOR TREATING CD40-MEDIATED DISEASES

(71) Applicants: CASE WESTERN RESERVE UNIVERSITY, Cleveland, OH (US); Carlos Subauste, Cleveland, OH (US)

(72) Inventors: Carlos Subauste, Cleveland, OH (US); Cecilia Subauste, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 666 days.

This patent is subject to a terminal disclaimer.

(21) Appl. No.: 16/890,486

(22) Filed: Jun. 2, 2020

(65) Prior Publication Data

US 2020/0308252 A1    Oct. 1, 2020

Related U.S. Application Data

(63) Continuation-in-part of application No. 15/346,252, filed on Nov. 8, 2016, now Pat. No. 10,669,345, which is a continuation-in-part of application No. 12/993,375, filed as application No. PCT/US2009/044500 on May 19, 2009, now Pat. No. 9,486,498.

(60) Provisional application No. 63/004,026, filed on Apr. 2, 2020, provisional application No. 61/054,293, filed on May 19, 2008.

(51) Int. Cl.
| | |
|---|---|
| *C07K 14/435* | (2006.01) |
| *A61P 29/00* | (2006.01) |
| *C07K 14/705* | (2006.01) |
| *A61K 38/00* | (2006.01) |

(52) U.S. Cl.
CPC ........ *C07K 14/70578* (2013.01); *A61P 29/00* (2018.01); *A61K 38/00* (2013.01)

(58) Field of Classification Search
None
See application file for complete search history.

(56) References Cited

U.S. PATENT DOCUMENTS

| | | |
|---|---|---|
| 9,486,498 B2 | 11/2016 | Subauste |
| 2003/0027744 A1 | 2/2003 | Dana et al. |
| 2004/0087774 A1 | 5/2004 | Goeddel et al. |
| 2004/0197867 A1 | 10/2004 | Titus et al. |
| 2005/0272050 A1 | 12/2005 | Mintz et al. |

OTHER PUBLICATIONS

Che, H., et al., "Interference with Nuclear Factor Kappa B and c-Jun NH2-Terminal Kinase Signaling by TRAF6C Small Interfering RNA Inhibits Myeloma Cell Proliferation and Enhances Apoptosiss", Oncogen, May 2006, vol. 25, pp. 6520-6527: Abstract, p. 6524.
Inwald, D.P., et al., CD40 is Constitutively Expressed on Platelets and Provides a Novel Mechanism for platelet Activation. Circulation Research. Apr. 2003, vol. 92(9), pp. 1041-1048: abstract.
Lee, H. H., et al., Specifics of CD40 signaling: Involvement of TRAF2 in CD40-Induced NF-kB Activation and Intracellular Adhesion Molecule-1 Up-Regulation. Proc. Natl. Acad. Sci. USA, Feb. 1999, vol. 96(4), pp. 1421-1426: abstract; p. 1423.

*Primary Examiner* — Michael D Pak
(74) *Attorney, Agent, or Firm* — Tarolli, Sundheim, Covell & Tummino LLP

(57) ABSTRACT

A cell-permeable polypeptide includes a membrane transduction domain and a polypeptide comprising an amino acid sequence substantially homologous to the amino acid sequence of the TRAF2,3 binding domain, the cell permeable peptide inhibiting binding of TRAF2 to the TRAF2,3 binding domain of CD40 to decrease or inhibit a CD-40 activity or signal transduction pathway associated with a CD40-mediated disease in cells of a subject.

6 Claims, 29 Drawing Sheets
Specification includes a Sequence Listing.

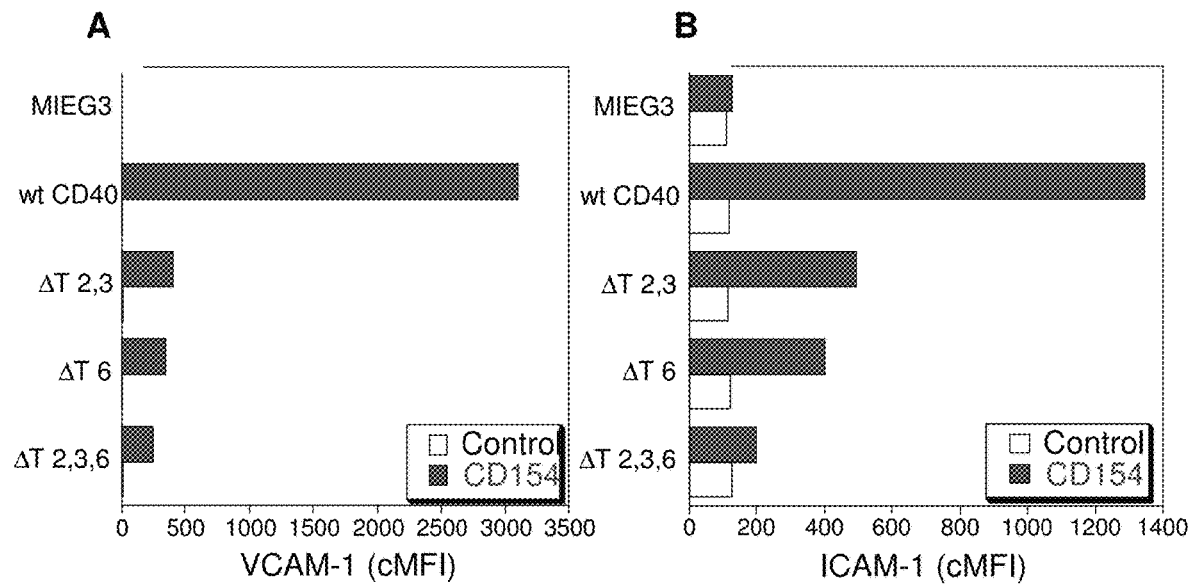
FIG. 2A  FIG. 2B
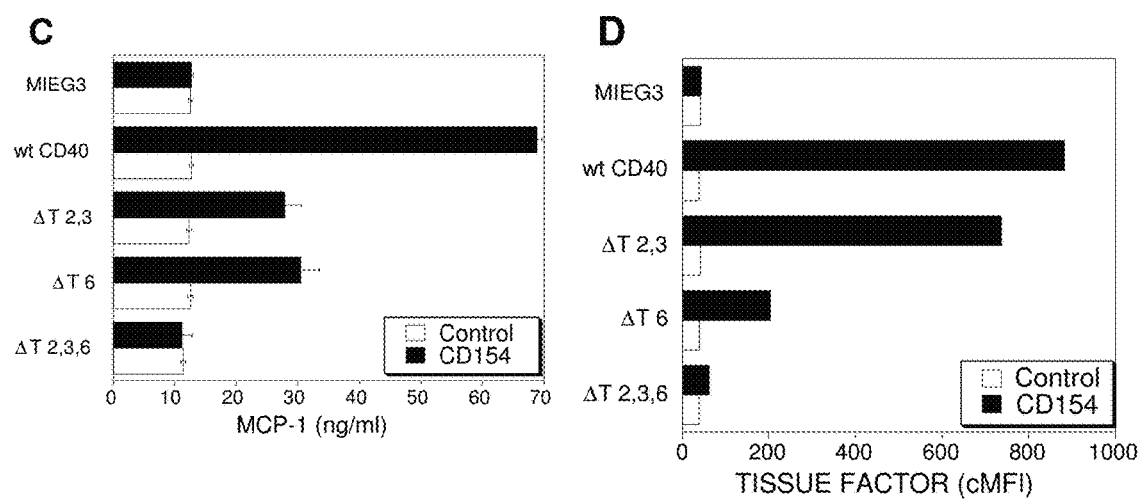
FIG. 2C  FIG. 2D

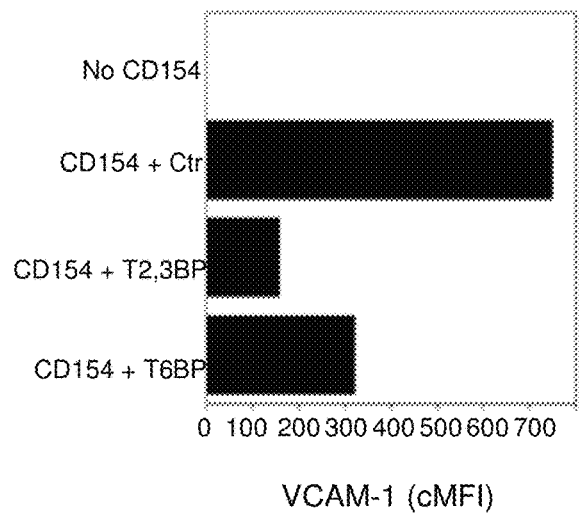
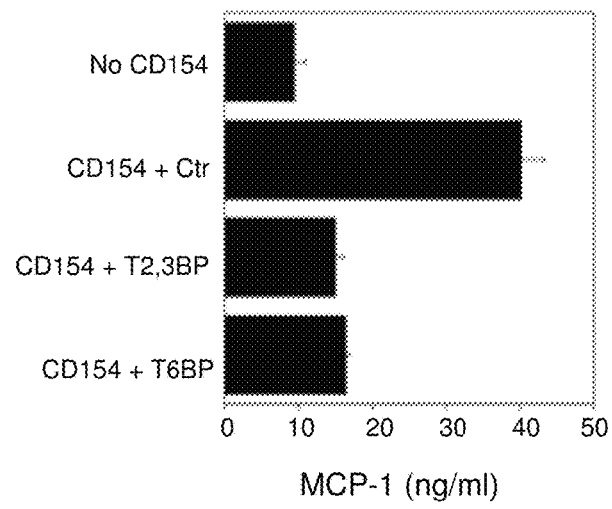
FIG. 3A          FIG. 3B
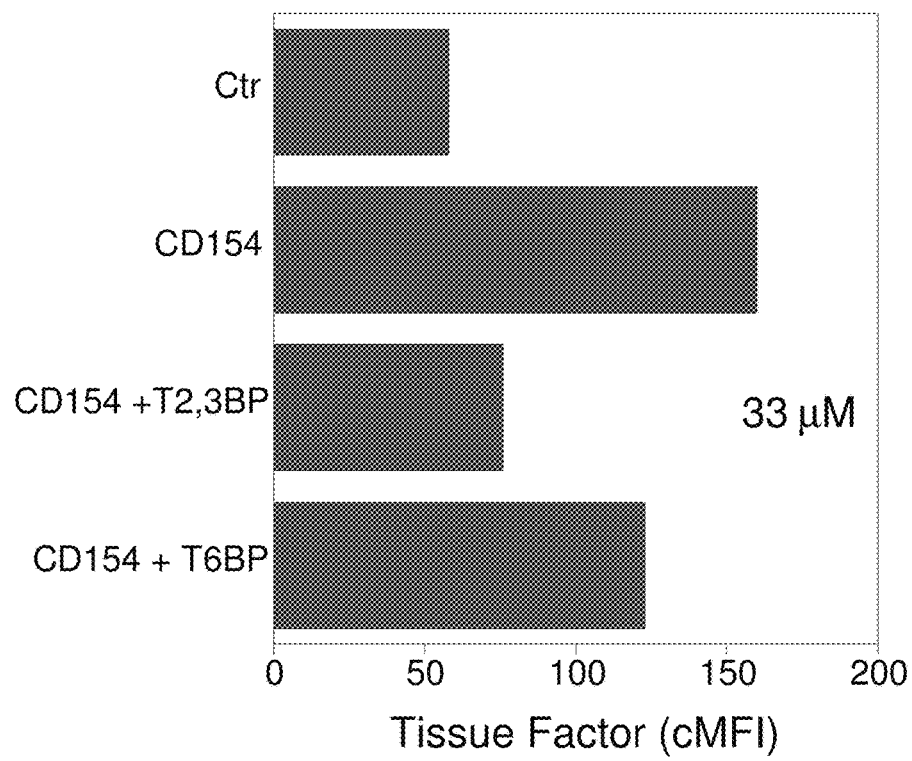
FIG. 4

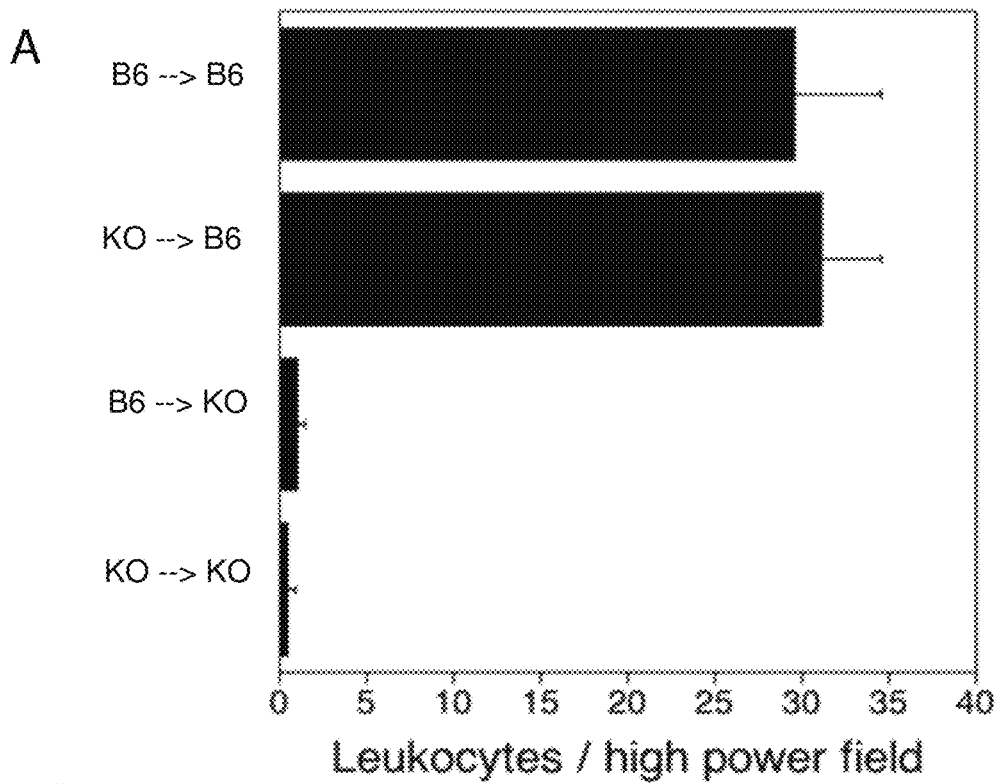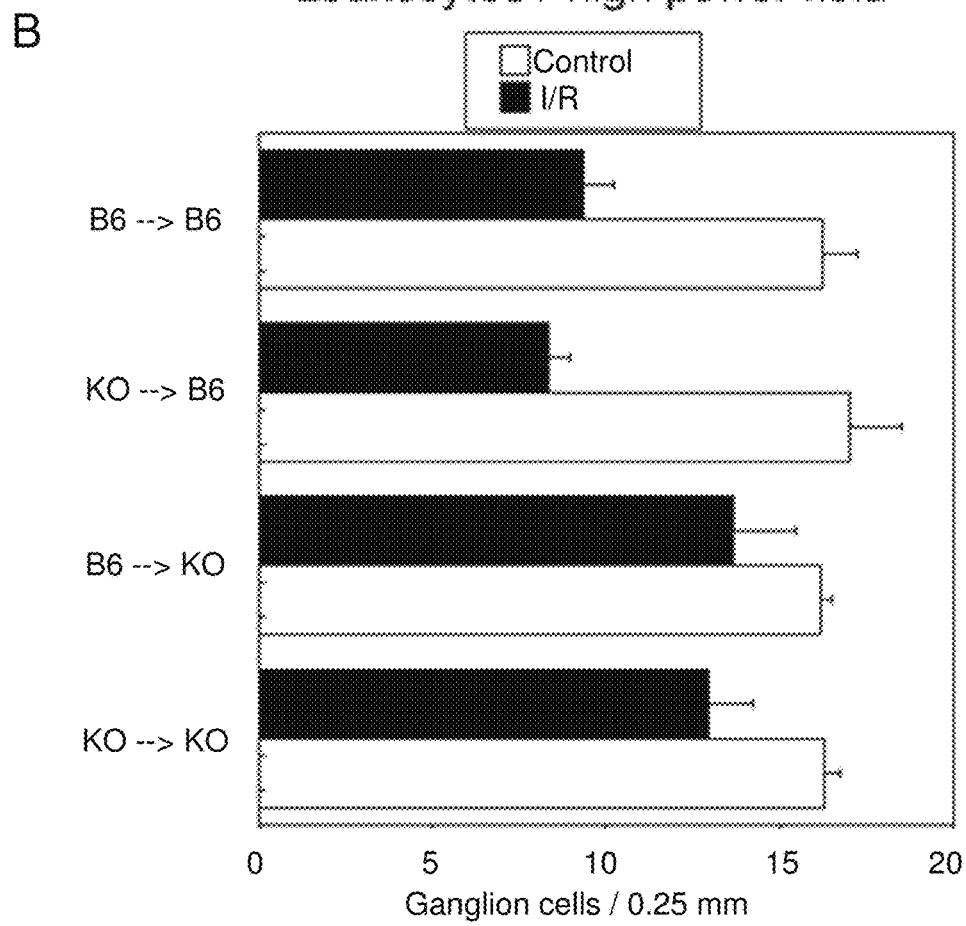
FIGS. 15A-B

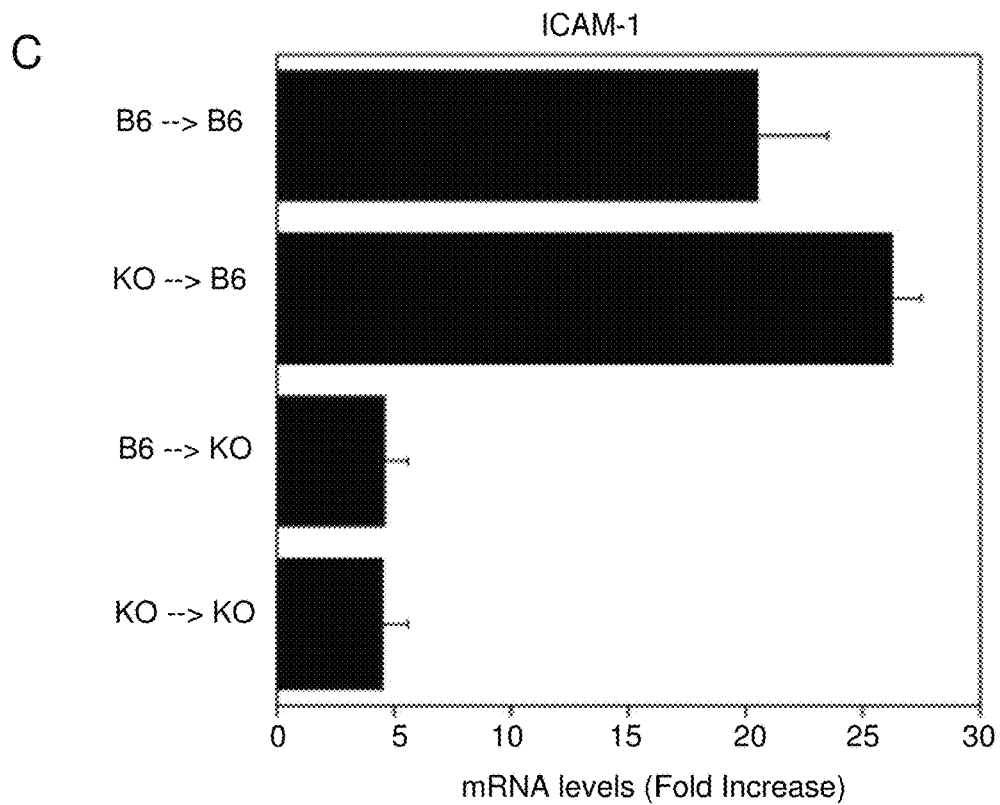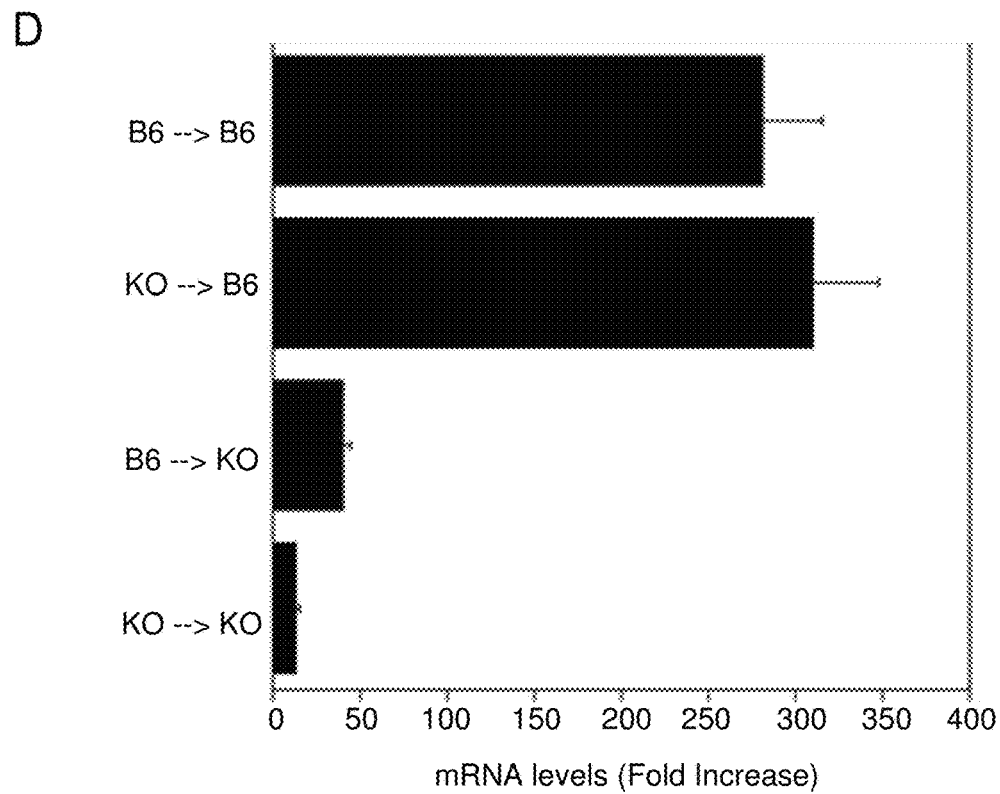
FIGS. 15C-D

```
                         SEQUENCE LISTING

<160> NUMBER OF SEQ ID NOS: 50

<210> SEQ ID NO 1
<211> LENGTH: 29
<212> TYPE: PRT
<213> ORGANISM: Artificial Sequence
<220> FEATURE:
<223> OTHER INFORMATION: Synthetic Construct

<400> SEQUENCE: 1

Ala Ala Val Ala Leu Leu Pro Ala Val Leu Leu Ala Leu Leu Ala Pro
1               5                   10                  15

Ser Asn Thr Ala Ala Pro Val Gln Glu Thr Leu His Gly
            20                  25

<210> SEQ ID NO 2
<211> LENGTH: 32
<212> TYPE: PRT
<213> ORGANISM: Artificial Sequence
<220> FEATURE:
<223> OTHER INFORMATION: Synthetic Construct

<400> SEQUENCE: 2

Ala Ala Val Ala Leu Leu Pro Ala Val Leu Leu Ala Leu Leu Ala Pro
1               5                   10                  15

Ala Pro His Pro Lys Gln Glu Pro Gln Glu Ile Asp Phe Pro Asp Asp
            20                  25                  30

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Ala Ala Val Ala Leu Leu Pro Ala Val Leu Leu Ala Leu Leu Ala Pro
1               5                   10                  15

<210> SEQ ID NO 4
<211> LENGTH: 34
<212> TYPE: PRT
<213> ORGANISM: Artificial Sequence
<220> FEATURE:
<223> OTHER INFORMATION: Synthetic Construct

<400> SEQUENCE: 4

Asn Ala Ala Thr Ala Thr Arg Gly Arg Ser Ala Ala Ser Arg Pro Thr
```

```
1               5                   10                  15
Glu Arg Pro Arg Ala Pro Ala Arg Ser Ala Ser Arg Pro Arg Pro
            20                  25                  30

Val Glu

<210> SEQ ID NO 5
<211> LENGTH: 15
<212> TYPE: PRT
<213> ORGANISM: Artificial Sequence
<220> FEATURE:
<223> OTHER INFORMATION: Synthetic Construct

<400> SEQUENCE: 5

Cys Gly Arg Lys Lys Arg Arg Gln Arg Arg Pro Pro Gln Cys
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Arg Lys Lys Arg Arg Gln Arg Arg Arg
1               5

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Arg Gln Ile Lys Ile Trp Phe Gln Asn Arg Arg Met Lys Trp Lys Lys
1               5                   10                  15

<210> SEQ ID NO 8
<211> LENGTH: 26
<212> TYPE: PRT
<213> ORGANISM: Artificial Sequence
<220> FEATURE:
<223> OTHER INFORMATION: Synthetic Construct

<400> SEQUENCE: 8

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 9
<211> LENGTH: 18
<212> TYPE: PRT
<213> ORGANISM: Artificial Sequence
<220> FEATURE:
<223> OTHER INFORMATION: Synthetic Construct

<400> SEQUENCE: 9

Lys Leu Ala Leu Lys Leu Ala Leu Lys Ala Leu Lys Ala Ala Leu Lys
1               5                   10                  15

Leu Ala

<210> SEQ ID NO 10
```

```
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Ser Asn Thr Ala Ala Pro Val Gln Glu Thr Leu His Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Asn Thr Ala Ala His Val Gln Glu Thr Leu His Gly
1               5                   10

<210> SEQ ID NO 12
<211> LENGTH: 24
<212> TYPE: PRT
<213> ORGANISM: Artificial Sequence
<220> FEATURE:
<223> OTHER INFORMATION: Synthetic Construct

<400> SEQUENCE: 12

Ser Asn Thr Ala Ala Pro Val Gln Glu Thr Leu His Gly Tyr Gly Arg
1               5                   10                  15

Lys Lys Arg Arg Gln Arg Arg Arg
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct

<400> SEQUENCE: 13

Asn Thr Ala Ala His Val Gln Glu Thr Leu His Gly Tyr Gly Arg Lys
1               5                   10                  15

Lys Arg Arg Gln Arg Arg Arg
            20

<210> SEQ ID NO 14
<211> LENGTH: 16
<212> TYPE: PRT
<213> ORGANISM: Artificial Sequence
<220> FEATURE:
<223> OTHER INFORMATION: Synthetic Construct

<400> SEQUENCE: 14

Ala Pro His Pro Lys Gln Glu Pro Gln Glu Ile Asp Phe Pro Asp Asp
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Synthetic Construct

<400> SEQUENCE: 15
```

-continued

Lys Gln Glu Pro Gln Glu Ile Asp Phe Pro Asp Asp
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct

<400> SEQUENCE: 16

Lys Gln Glu Pro Gln Glu Ile Asn Phe Pro Asp Asp Leu
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa is equal to Asp, Glu, Phe, Gly, His

<400> SEQUENCE: 17

Lys Gln Glu Ala Gln Glu Ile Asn Phe Xaa Asp Asp Leu
1               5                   10

<210> SEQ ID NO 18
<211> LENGTH: 23
<212> TYPE: PRT
<213> ORGANISM: Artificial Sequence
<220> FEATURE:
<223> OTHER INFORMATION: Synthetic Construct

<400> SEQUENCE: 18

Lys Gln Glu Pro Gln Glu Ile Asp Phe Pro Asp Asp Tyr Gly Arg Lys
1               5                   10                  15

Lys Arg Arg Gln Arg Arg Arg
            20

<210> SEQ ID NO 19
<211> LENGTH: 24
<212> TYPE: PRT
<213> ORGANISM: Artificial Sequence
<220> FEATURE:
<223> OTHER INFORMATION: Synthetic Construct

<400> SEQUENCE: 19

Lys Gln Glu Pro Gln Glu Ile Asn Phe Pro Asp Asp Leu Tyr Gly Arg
1               5                   10                  15

Lys Lys Arg Arg Gln Arg Arg Arg
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa is equal to Asp, Glu, Phe, Gly, His

<400> SEQUENCE: 20

```
Lys Gln Glu Ala Gln Glu Ile Asn Phe Xaa Asp Asp Leu Tyr Gly Arg
1               5                   10                  15

Lys Lys Arg Arg Gln Arg Arg Arg
            20
```

<210> SEQ ID NO 21
<211> LENGTH: 13
<212> TYPE: PRT
<213> ORGANISM: Artificial Sequence
<220> FEATURE:
<223> OTHER INFORMATION: Synthetic Construct

<400> SEQUENCE: 21

```
Ser Asn Thr Ala Ala His Val Gln Glu Thr Leu His Gly
1               5                   10
```

<210> SEQ ID NO 22
<211> LENGTH: 13
<212> TYPE: PRT
<213> ORGANISM: Artificial Sequence
<220> FEATURE:
<223> OTHER INFORMATION: Synthetic Construct

<400> SEQUENCE: 22

```
Ser Asn Thr Ala Ala His Ile Gln Glu Thr Leu His Gly
1               5                   10
```

<210> SEQ ID NO 23
<211> LENGTH: 13
<212> TYPE: PRT
<213> ORGANISM: Artificial Sequence
<220> FEATURE:
<223> OTHER INFORMATION: Synthetic Construct

<400> SEQUENCE: 23

```
Ser Asn Thr Ala Ala His Val Gln Glu Ser Leu His Gly
1               5                   10
```

<210> SEQ ID NO 24
<211> LENGTH: 13
<212> TYPE: PRT
<213> ORGANISM: Artificial Sequence
<220> FEATURE:
<223> OTHER INFORMATION: Synthetic Construct

<400> SEQUENCE: 24

```
Ser Asn Thr Ala Ala His Ile Gln Glu Ser Leu His Gly
1               5                   10
```

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

```
Ser Asn Thr Ala Ala Pro Ile Gln Glu Thr Leu His Gly
1               5                   10
```

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

```
<400> SEQUENCE: 26

Ser Asn Thr Ala Ala Pro Ile Gln Glu Ser Leu His Gly
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic Construct

<400> SEQUENCE: 27

Ser Asn Thr Ala Ala Pro Val Gln Glu Ser Leu His Gly
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Pro or His
<220> FEATURE:
<221> NAME/KEY: MOD_RES
<222> LOCATION: (2)..(2)
<223> OTHER INFORMATION: Xaa is Val, Ile, or Thr
<220> FEATURE:
<221> NAME/KEY: MOD_RES
<222> LOCATION: (5)..(5)
<223> OTHER INFORMATION: Xaa is Thr or Ser

<400> SEQUENCE: 28

Xaa Xaa Gln Glu Xaa
1               5

<210> SEQ ID NO 29
<211> LENGTH: 5
<212> TYPE: PRT
<213> ORGANISM: Homo sapiens

<400> SEQUENCE: 29

Pro Val Gln Glu Thr
1               5

<210> SEQ ID NO 30
<211> LENGTH: 14
<212> TYPE: PRT
<213> ORGANISM: Homo sapiens

<400> SEQUENCE: 30

Asp Leu Pro Gly Ser Asn Thr Ala Ala Pro Val Gln Glu Thr
1               5                   10

<210> SEQ ID NO 31
<211> LENGTH: 13
<212> TYPE: PRT
<213> ORGANISM: Homo sapiens

<400> SEQUENCE: 31

Asn Thr Ala Ala Pro Val Gln Glu Thr Leu His Gly Cys
1               5                   10

<210> SEQ ID NO 32
<211> LENGTH: 12
```

```
<212> TYPE: PRT
<213> ORGANISM: Homo sapiens

<400> SEQUENCE: 32

Asn Thr Ala Ala Pro Val Gln Glu Thr Leu His Gly
1               5                   10

<210> SEQ ID NO 33
<211> LENGTH: 11
<212> TYPE: PRT
<213> ORGANISM: Homo sapiens

<400> SEQUENCE: 33

Asn Thr Ala Ala Pro Val Gln Glu Thr Leu His
1               5                   10

<210> SEQ ID NO 34
<211> LENGTH: 10
<212> TYPE: PRT
<213> ORGANISM: Homo sapiens

<400> SEQUENCE: 34

Asn Thr Ala Ala Pro Val Gln Glu Thr Leu
1               5                   10

<210> SEQ ID NO 35
<211> LENGTH: 9
<212> TYPE: PRT
<213> ORGANISM: Homo sapiens

<400> SEQUENCE: 35

Asn Thr Ala Ala Pro Val Gln Glu Thr
1               5

<210> SEQ ID NO 36
<211> LENGTH: 29
<212> TYPE: PRT
<213> ORGANISM: Artificial Sequence
<220> FEATURE:
<223> OTHER INFORMATION: Synthetic Construct

<400> SEQUENCE: 36

Ala Ala Val Ala Leu Leu Pro Ala Val Leu Leu Ala Leu Leu Ala Pro
1               5                   10                  15

Ser Asn Thr Ala Ala Pro Val Gln Glu Thr Leu His Gly
            20                  25

<210> SEQ ID NO 37
<211> LENGTH: 23
<212> TYPE: PRT
<213> ORGANISM: Artificial Sequence
<220> FEATURE:
<223> OTHER INFORMATION: Synthetic Construct

<400> SEQUENCE: 37

Asn Thr Ala Ala Pro Val Gln Glu Thr Leu His Gly Tyr Gly Arg Lys
1               5                   10                  15

Lys Arg Arg Gln Arg Arg Arg
            20

<210> SEQ ID NO 38
<211> LENGTH: 5
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MOD_RES
<222> LOCATION: (1)..(1)
<223> OTHER INFORMATION: Xaa is Thr or Ser
<220> FEATURE:
<221> NAME/KEY: MOD_RES
<222> LOCATION: (4)..(4)
<223> OTHER INFORMATION: Xaa is Val, Ile, or Thr
<220> FEATURE:
<221> NAME/KEY: MOD_RES
<222> LOCATION: (5)..(5)
<223> OTHER INFORMATION: Xaa is Pro or His

<400> SEQUENCE: 38

Xaa Glu Gln Xaa Xaa
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Thr Glu Gln Val Pro
1               5

<210> SEQ ID NO 40
<211> LENGTH: 14
<212> TYPE: PRT
<213> ORGANISM: Artificial Sequence
<220> FEATURE:
<223> OTHER INFORMATION: Synthetic Construct

<400> SEQUENCE: 40

Thr Glu Gln Val Pro Ala Ala Thr Asn Ser Gly Pro Leu Asp
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic Construct

<400> SEQUENCE: 41

Thr Glu Gln Val Pro Ala Ala Thr Asn Ser Gly Pro Leu
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic Construct

<400> SEQUENCE: 42

Thr Glu Gln Val Pro Ala Ala Thr Asn Ser Gly Pro
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 43

Thr Glu Gln Val Pro Ala Ala Thr Asn Ser Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Thr Glu Gln Val Pro Ala Ala Thr Asn Ser
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Thr Glu Gln Val Pro Ala Ala Thr Asn
1               5

<210> SEQ ID NO 46
<211> LENGTH: 28
<212> TYPE: PRT
<213> ORGANISM: Artificial Sequence
<220> FEATURE:
<223> OTHER INFORMATION: Synthetic Construct

<400> SEQUENCE: 46

Gly His Leu Thr Glu Gln Val Pro Ala Ala Thr Asn Pro Ala Leu Leu
1               5                   10                  15

Ala Leu Leu Val Ala Pro Leu Leu Ala Val Ala Ala
            20                  25

<210> SEQ ID NO 47
<211> LENGTH: 28
<212> TYPE: PRT
<213> ORGANISM: Artificial Sequence
<220> FEATURE:
<223> OTHER INFORMATION: Synthetic Construct

<400> SEQUENCE: 47

Gly His Leu Thr Glu Gln Val His Ala Ala Thr Asn Pro Ala Leu Leu
1               5                   10                  15

Ala Leu Leu Val Ala Pro Leu Leu Ala Val Ala Ala
            20                  25

<210> SEQ ID NO 48
<211> LENGTH: 23
<212> TYPE: PRT
<213> ORGANISM: Artificial Sequence
<220> FEATURE:
<223> OTHER INFORMATION: Synthetic Construct

<400> SEQUENCE: 48

Arg Arg Arg Gln Arg Arg Lys Lys Arg Gly Tyr Gly His Leu Thr Glu
1               5                   10                  15

Gln Val Pro Ala Ala Thr Asn
            20
```

```
<210> SEQ ID NO 49
<211> LENGTH: 23
<212> TYPE: PRT
<213> ORGANISM: Artificial Sequence
<220> FEATURE:
<223> OTHER INFORMATION: Synthetic Construct

<400> SEQUENCE: 49

Arg Arg Arg Gln Arg Arg Lys Lys Arg Gly Tyr Gly His Leu Thr Glu
1               5                   10                  15

Gln Val His Ala Ala Thr Asn
            20

<210> SEQ ID NO 50
<211> LENGTH: 23
<212> TYPE: PRT
<213> ORGANISM: Artificial Sequence
<220> FEATURE:
<223> OTHER INFORMATION: Synthetic Construct

<400> SEQUENCE: 50

Arg Arg Arg Gln Arg Arg Lys Lys Arg Gly Tyr Asn Thr Gln Ala Leu
1               5                   10                  15

Ala His Thr Gly Glu Val His
            20
```

METHOD FOR TREATING CD40-MEDIATED DISEASES

RELATED APPLICATION

This application is a Continuation-in-Part of U.S. patent application Ser. No. 15/346,252, filed Nov. 8, 2016, now U.S. Pat. No. 10,669,345, which is a Continuation-in-Part of U.S. patent application Ser. No. 12/993,375, filed Nov. 18, 2010, now U.S. Pat. No. 9,486,498, which is a National Phase Filing of PCT/US2009/044500, filed May 19, 2009, which claims priority from U.S. Provisional Application No. 61/054,293, filed May 19, 2008, this application also claims priority to U.S. Provisional Application Ser. No. 63/004,026, filed Apr. 2, 2020, the subject matter of which are incorporated herein by reference in their entirety.

TECHNICAL FIELD

The present invention relates generally to methods for treating CD40-mediated diseases, and more particularly to methods for treating CD40-mediated inflammatory diseases.

BACKGROUND OF THE INVENTION

CD40 is a member of the TNF receptor superfamily that is expressed on a wide variety of cells including antigen presenting cells (e.g., dendritic cells, macrophages, B cells) and non-immune cells, such as endothelial cells, smooth muscle cells, fibroblasts, epithelial cells, astrocytes and neurons. Its counter-receptor, CD154 (CD40 ligand), is expressed primarily on activated CD4+ T cells; although, other cells, such as platelets can also express CD154.

The interaction between CD40 and CD154 is central to the pathogenesis of numerous diseases including, for example, atherosclerosis, neurodegenerative disorders (e.g., Alzheimer's disease, cerebral ischemia, multiple sclerosis, amyotrophic lateral sclerosis) various autoimmune disorders (e.g., inflammatory bowel disease, systemic lupus erythematosus, rheumatoid arthritis, graft rejection, idiopathic thrombocytopenic purpura, inflammatory myopathies, etc.), rejection of transplanted organs, and ischemia. Numerous studies have demonstrated that in vivo blockade of the CD40-CD154 pathway controls these diseases in animals. Another role of CD40-CD154 interaction is to activate mechanisms of resistance against a broad variety of pathogens. This is important because approaches to control CD40-mediated diseases should ideally manipulate this pathway so that mechanisms of host resistance remain largely intact.

The relevance of CD40-CD154 interaction in the pathogenesis of numerous diseases has led to clinical trials which examined the effects of blocking this pathway. While generalized blockade of CD40 signaling by administration of an anti-CD154 monoclonal antibody appeared effective, the studies were discontinued because anti-CD154 monoclonal antibodies caused platelet aggregation and thrombosis. These effects are likely caused by activation of platelets via engagement of CD154 expressed on their membrane. Thus, approaches to target CD40 for therapy have not been feasible, and indiscriminate inhibition of the CD40 pathway may cause susceptibility to opportunistic infections.

SUMMARY OF THE INVENTION

The present invention relates generally to methods for treating CD40-mediated diseases, and more particularly to methods for treating CD40-mediated inflammatory diseases. The method can include administering to cells expressing CD40 of the subject a therapeutically effective amount of an agent that inhibits binding of TNF receptor associated factor 2 (TRAF2) to a cytoplasmic portion of CD40. The agent in accordance with the invention does not inhibit binding of CD40 ligand (CD40L) to CD40 of the cells. The agent can be administered to the cells at an amount effective to inhibit at least one of the following pro-inflammatory responses: upregulation of VCAM-1 or ICAM-1 from the cells, or production of chemokines such as MCP-1 or CXCL1, or production of tissue factor or metalloproteinases, or nitric oxide, or prostaglandins from the cells. Advantageously, the agent does not promote platelet aggregation or thrombosis in the subject, and the cell-mediated immune response of the subject is substantially unimpaired.

In an aspect of the invention, the CD40-mediated disease can include an inflammatory disease, disorders of the immune system, or a disease comprising malignant B-cells. The inflammatory disease can be selected from the group consisting of an atherogenic disease, a neurodegenerative disease, an autoimmune disease, ischemia, diabetes mellitus, and retinopathy.

In another aspect of the invention, the CD40-expressing cell can include an antigen-presenting cell (APC) including B-cell as well as a non-immune cells selected from the group consisting of endothelial cells, smooth muscle cells, fibroblasts, epithelial cells, astrocytes, neurons, and Muller cells.

In a further aspect of the invention, the agent can include a cell-permeable polypeptide that competitively inhibits binding of TRAF2 to the TRAF2,3 binding domain of CD40. The cell-permeable polypeptide can include a membrane transduction domain and a polypeptide comprising an amino acid sequence substantially homologous to the amino acid sequence of the TRAF2,3 binding domain or a retro-inverso amino acid sequence thereof.

In a further aspect of the invention, the method can include administering to the subject a therapeutically effective amount of a second agent that inhibits the production or activity of interleukin-1 (IL-1) in the cell.

The present invention also relates to a method for treating a CD40-mediated disease in a subject that includes administering to cells expressing CD40 of the subject a therapeutically effective amount of a first agent that inhibits the binding of TRAF2 to CD40 and a second agent that inhibits the production or activity of interleukin-1 (IL-1). The first agent and the second agent do not inhibit binding of CD40L to CD40 of the cells. The first agent can be administered to the cells at an amount effective to inhibit at least one of the following pro-inflammatory responses: upregulation of VCAM-1 or ICAM-1 from the cells, or production of chemokines such as MCP-1 or CXCL1 or production of tissue factor, or metalloproteinases, or nitric oxide, or prostaglandins from the cells. Advantageously, the first agent and the second agent do not promote platelet aggregation or thrombosis in the subject and the cell-mediated immune response of the subject is substantially unimpaired.

In an aspect of the invention, the CD40-mediated disease can include an inflammatory disease, disorders of the immune system, or a disease comprising malignant B-cells. The inflammatory disease can be selected from the group consisting of an atherogenic disease, a neurodegenerative disease, an autoimmune disease, organ ischemia, diabetes mellitus, and retinopathy.

In another aspect of the invention, the CD40-expressing cell can include an antigen-presenting cell (APC) or B-cell as well as a non-immune cell selected from the group consisting of endothelial cells, smooth muscle cells, fibroblasts, epithelial cells, astrocytes, neurons, and Muller cells.

In a further aspect of the invention, the first agent can include a cell-permeable polypeptide that competitively inhibits binding of TRAF2 to the TRAF2,3 binding domain of CD40. The cell-permeable polypeptide can include a membrane transduction domain and a polypeptide comprising an amino acid sequence substantially homologous to the amino acid sequence of the TRAF2,3 binding domain.

In another aspect of the invention, the second agent can include a cell-permeable polypeptide that competitively inhibits binding of TRAF6 to the TRAF6 binding domain of CD40. The cell-permeable polypeptide can include a membrane transduction domain and a peptide comprising an amino acid sequence substantially homologous to the amino acid sequence of the TRAF6 binding domain. In a further aspect of the invention, the second agent can include an antibody or antibody fragment reactive against IL-1.

The present invention further relates to a method for treating atherosclerosis in a subject. The method includes administering to the subject a therapeutically effective amount of an agent that inhibits binding of TNF receptor associated factor 2 (TRAF2) to a cytoplasmic portion of CD40 of a cell. The agent does not inhibit binding of CD40 ligand (CD40L) to CD40 of the cell. The agent can be administered to the cells at an amount effective to inhibit at least one of the following pro-inflammatory responses: upregulation of VCAM-1 or ICAM-1 from the cells, or production of MCP-1 or production of tissue factor, or metalloproteinases from the cells. Advantageously, the agent does not promote platelet aggregation or thrombosis in the subject and the cell-mediated immune response of the subject is substantially unimpaired.

In an aspect of the invention, the agent can include a cell-permeable polypeptide that competitively inhibits binding of TRAF2 to the TRAF2,3 binding domain of CD40. The cell-permeable polypeptide can include a membrane transduction domain and a polypeptide comprising an amino acid sequence substantially homologous to the amino acid sequence of the TRAF2,3 binding domain.

In a further aspect of the invention, the method can include administering to the subject a therapeutically effective amount of a second agent that inhibits the production or activity of interleukin-1 (IL-1) in the cell. The second agent can include a cell-permeable polypeptide that competitively inhibits binding of TRAF6 to the TRAF6 binding domain of CD40. The cell-permeable polypeptide can include a membrane transduction domain and a peptide comprising an amino acid sequence substantially homologous to the amino acid sequence of the TRAF6 binding domain. In a further aspect of the invention, the second agent can include an antibody or antibody fragment reactive against IL-1.

The present invention also relates to a method of treating retinopathy (e.g., diabetic or ischemic retinopathy) in a subject. The method can include administering to retinal cells of the subject a therapeutically effective amount of an agent that inhibits binding of TNF receptor associated factor 2 (TRAF2) to a cytoplasmic portion of CD40. The agent can be administered to the cells at an amount effective to inhibit at least one of upregulation of VCAM-1 or ICAM-1 from the cells, or production of MCP-1 or CXCL1, or nitric oxide or prostaglandins or metalloproteinases from the cells.

In an aspect of the invention, the agent can include a cell-permeable polypeptide that competitively inhibits binding of TRAF2 to the TRAF2,3 binding domain of CD40. The cell-permeable polypeptide can include a membrane transduction domain and a polypeptide comprising an amino acid sequence substantially homologous to the amino acid sequence of the TRAF2,3 binding domain. The agent can also include at least one of an anti-CD40 antibody or an anti-CD154 antibody that is locally administered to the retinal cells.

In another aspect of the invention, the method can include administering to the subject a therapeutically effective amount of a second agent that inhibits the production or activity of interleukin-1 (IL-1) in the cell. Another agent can also include a cell-permeable polypeptide that competitively inhibits binding of TRAF6 to the TRAF6 binding domain of CD40. The cell-permeable polypeptide can include a membrane transduction domain and a peptide comprising an amino acid sequence substantially homologous to the amino acid sequence of the TRAF6 binding domain.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 2A-D are a series of graphs showing the induction of VCAM-1 (FIG. 2A), ICAM-1 (FIG. 2B), MCP-1 (FIG. 2C), and tissue factor (FIG. 2D) expression by TRAFs. Human aortic endothelial cells (HAEC) transduced with empty EGFP-encoding retroviral vector (MIEG3) or retroviral vector that encoded either wild type CD40 (wt CD40), CD40 with a mutation that prevents recruitment of TRAF2 and 3 ($\Delta$T2, 3), recruitment of TRAF6 ($\Delta$T6), or recruitment of TRAF2, 3, and 6 ($\Delta$T2, 3, and 6) were incubated with or without CD154. VCAM-1, ICAM-1, and tissue factor were assessed by FACS on transduced (EGFP+) cells. cMFI=corrected Mean Fluorescence Intensity. MCP-1 was measured by ELISA (N=3).

FIGS. 3A-B are a series of graphs showing the effects cell-permeable polypeptides that block CD40-TRAF interactions (T2,3BP and T6BP) on upregulation of VCAM-1 and MCP-1 in HAEC. HAEC were transduced with retroviral vectors encoding wild-type CD40 and incubated with or without CD154. HAEC were pre-treated with either control, TRAF2,3 blocking peptide (T2,3BP), or TRAF6 blocking peptide (T6BP) (200 μM) (N=2).

FIG. 4 is a graph showing the effects of first generation peptides that block CD40-TRAF interaction on CD40-induced tissue factor upregulation (MonoMac 6 cells);

FIGS. 15A-D illustrates retinal expression of CD40 promotes pro-inflammatory responses and ganglion cell loss after retinal I/R. Bone marrow cells from B6 and CD40$^{-/-}$ (KO) mice were used to generate bone marrow chimeras. Four weeks after transplant, one eye from each mouse was subjected to I/R. Nonischemic eyes were used as controls. Eyes were obtained 1 day after I/R. A and B, Leukocytes in the retina and vitreous (A) as well as marked decrease in ganglion cells (B) were noted in ischemic eyes from KO→B6 and B6→B6 mice. Ischemic eyes from B6→KO and KO→KO mice exhibited less pronounced ganglion cell loss. C and D, Retinal CD40 promotes up-regulation of ICAM-1 (C) and KC/CXCL1 (D) mRNA in ischemic retinas. RNA was isolated from ischemic and nonischemic retinas. cDNA was subjected to quantitative real-time PCR. ICAM-1 and KC/CXCL1 mRNA levels were normalized against 18S rRNA. Data are expressed as fold increase of KC/CXCL1 and ICAM-1 in the ischemic vs the nonischemic retina. Values represent means±SEM (three to five mice per group).

ONL=Outer nuclear layer. Data shown represent Mean±SEM (9 mice per group). *P<0.05; P<0.01; *P<0.01.

Figure 21:
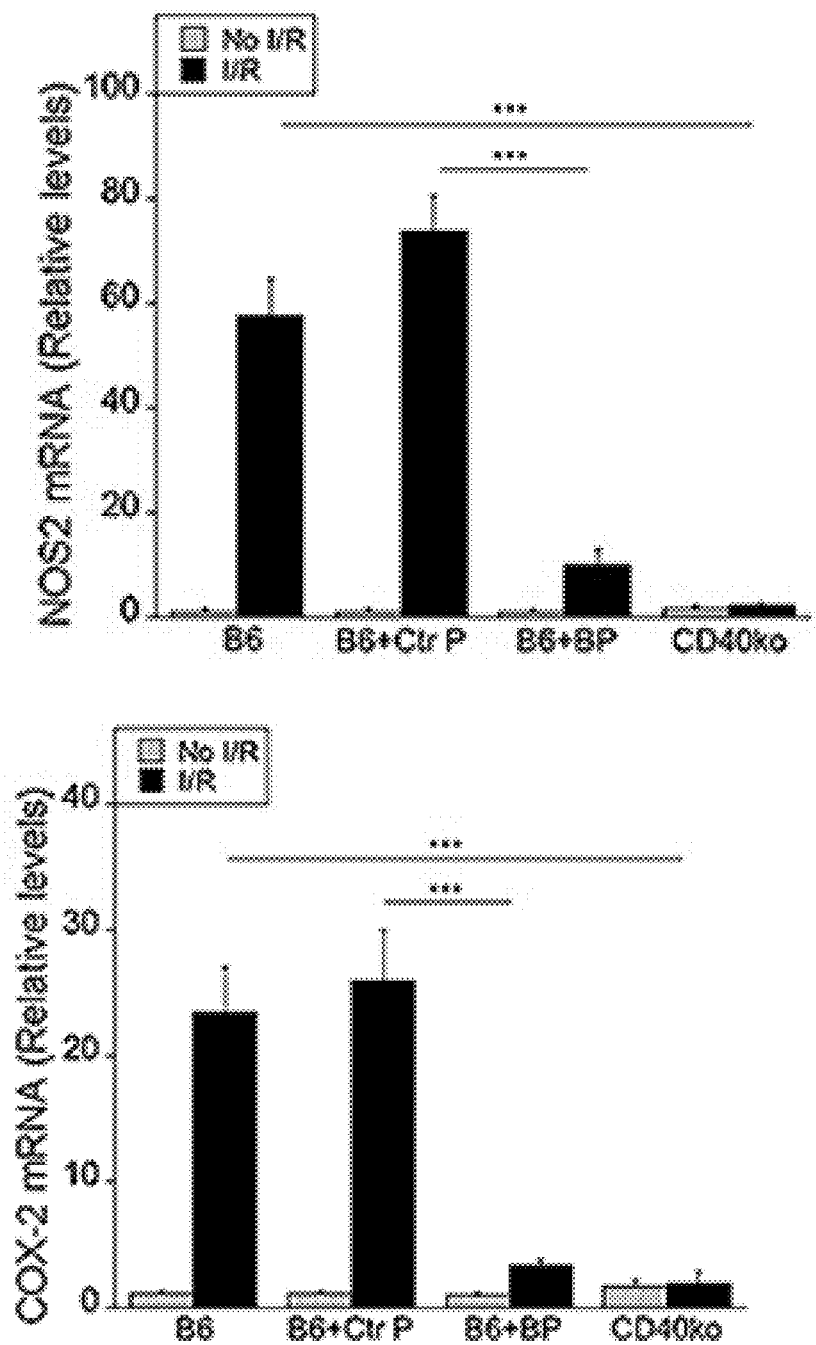

FIG. 21 illustrates graphs showing ri CD40-TRAF2,3 blocking peptide impairs upregulation of NOS2 and COX-2 in retinas subjected to I/R. One eye of each mouse was treated as above and subjected to I/R. Eyes were collected after 2 d. mRNA levels of NOS2 and COX-2 were assessed by quantitative real time PCR. One non-ischemic eye from a B6 mouse was given an arbitrary value of 1 and data are expressed as fold-increase compared to this animal. Data shown represent Mean±SEM (7-9 mice per group). ***P<0.001.

FIGS. 22(A-B) illustrate graphs and images showing ri CD40-TRAF2,3 blocking peptide impairs upregulation of ICAM-1 and KC/CXCL1 in retinal endothelial cells from retinas subjected to I/R. One eye of each mouse was subjected to I/R. Eyes were collected after 2 d. mRNA levels of ICAM-1 and KC/CXCL1 were assessed by quantitative real time PCR. One non-ischemic eye from a B6 mouse was given an arbitrary value of 1 and data are expressed as fold-increase compared to this animal. Data shown represent Mean±SEM (7-9 mice per group). ***P<0.001. Retinal sections were incubated with Tomato Lectin (labels endothelial cells) plus either anti-ICAM-1 or anti-KC/CXCL1 Ab. Original magnification ×600. GCL=Ganglion cell layer; IPL=Inner plexiform layer; INL=Inner nuclear layer. Scale bar, 10 μm. 6 mice/group.

Figure 23:
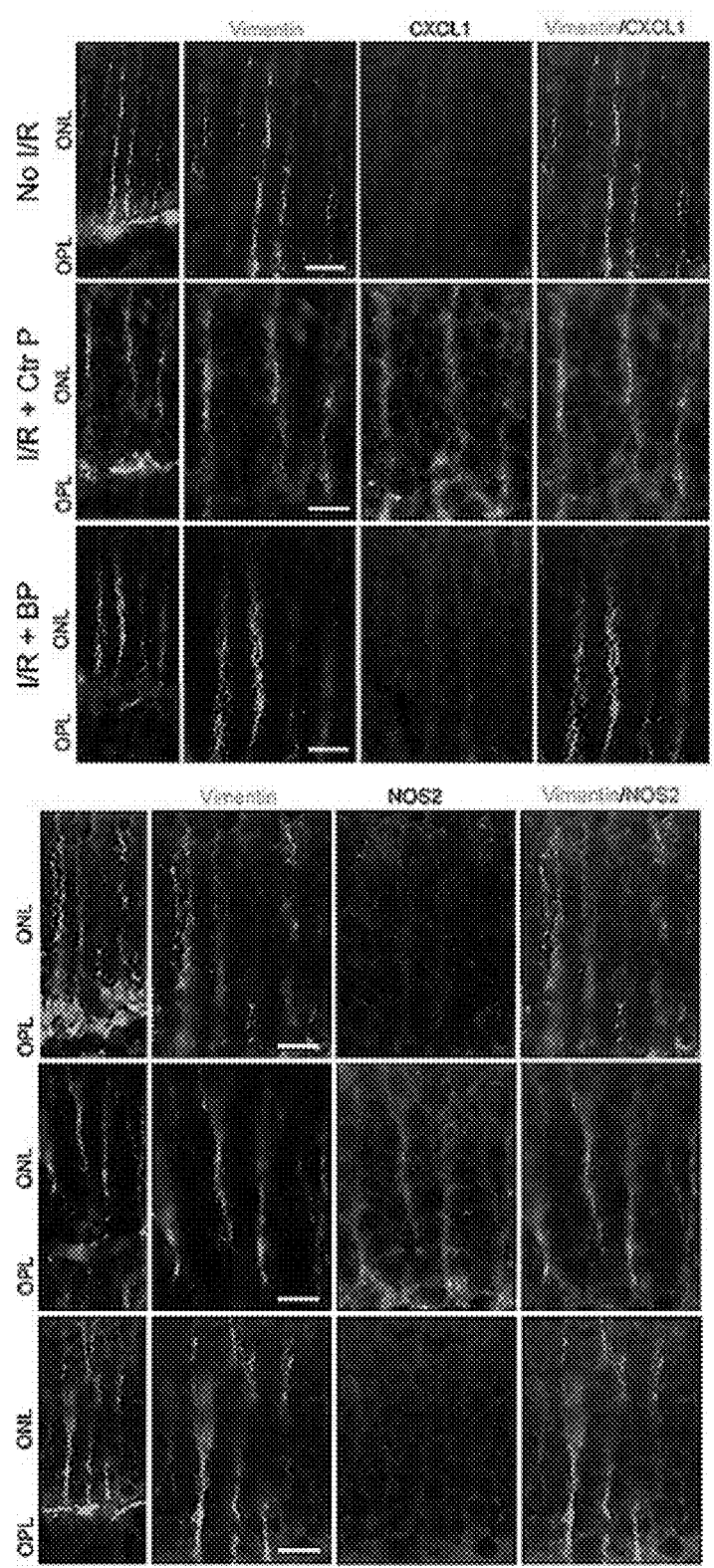
Figure 24A:
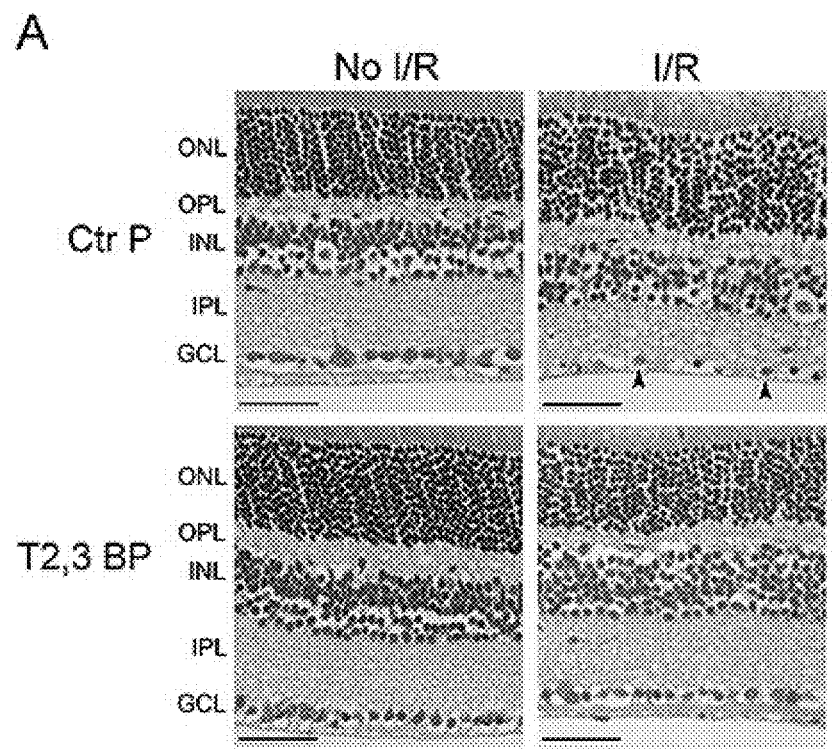
Figure 24B:
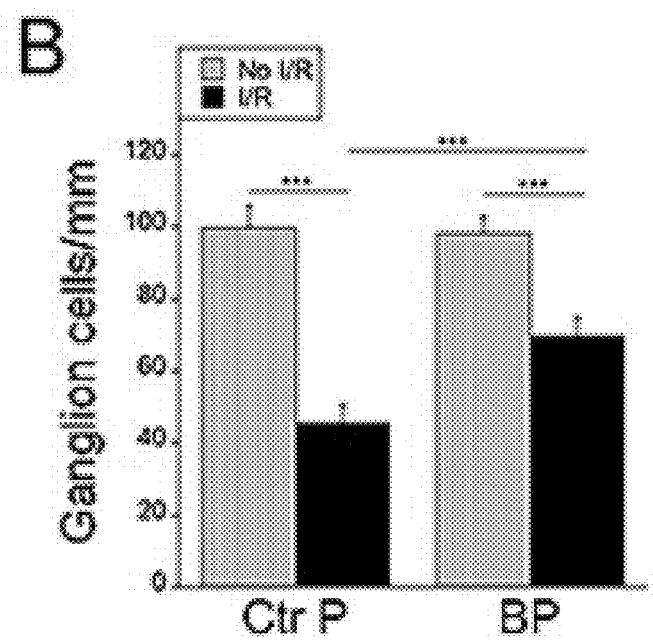
Figure 24C:
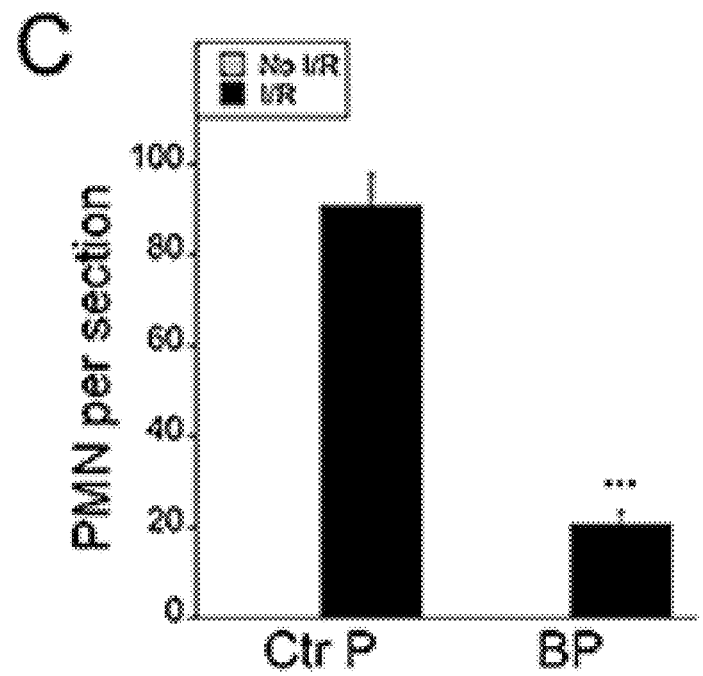
Figure 24D:
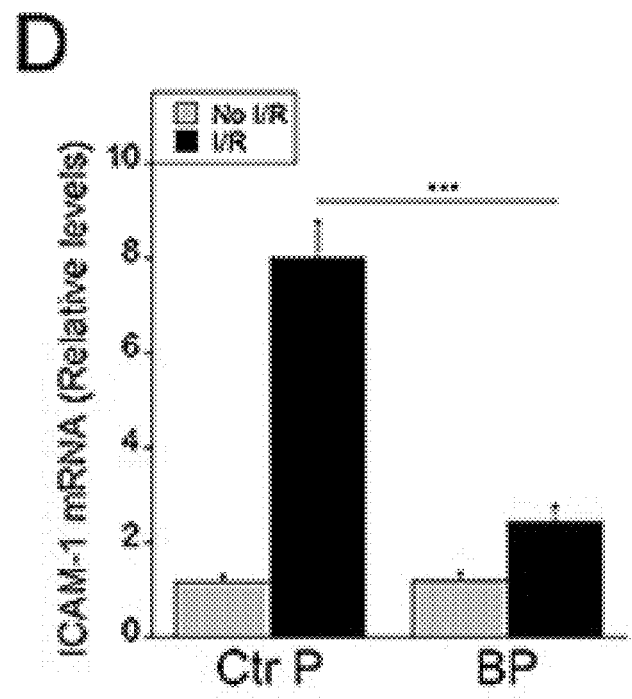
Figure 24D:
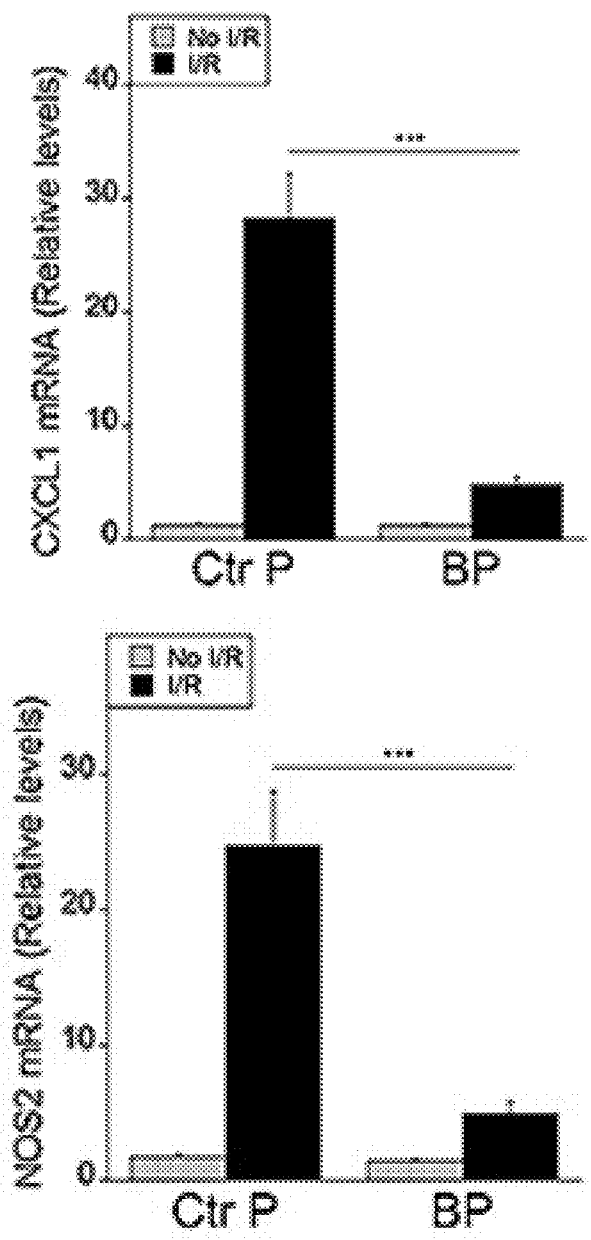
Figure 24D:
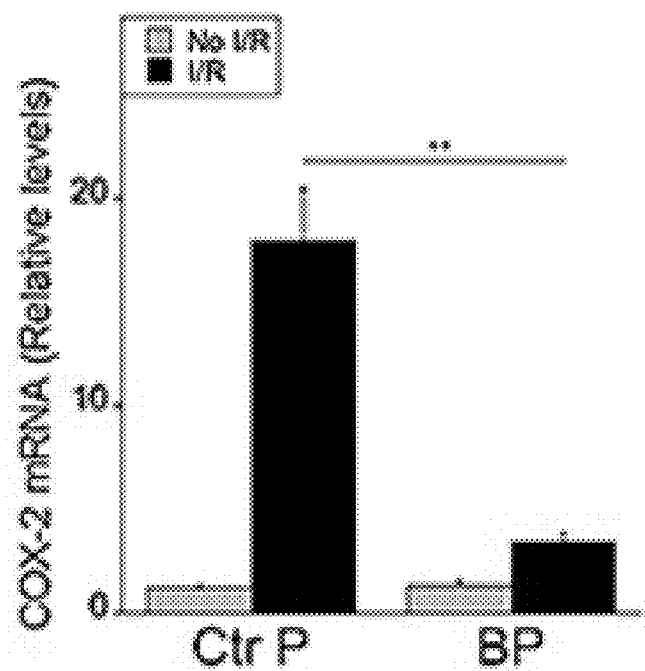

FIG. 23 illustrates images showing ri CD40-TRAF2,3 blocking peptide impairs NOS2 and KC/CXCL1 upregulation in Müller cells from retinas subjected to I/R. Eyes from B6 mice were treated with control peptide or CD40-TRAF2,3 blocking peptide, subjected to I/R and collected after 2 d. Retinal sections were incubated with anti-Vimentin Ab (labels Müller cells) plus either anti-NOS2 or anti-KC/CXCL1 Ab. Protein expression at the level of Müller cells stalks. OPL=Inner plexiform layer; ONL=Inner nuclear layer. Original magnification ×600. Scale bar, 10 μm. 6 mice/group.

FIGS. 24(A-D) illustrate images and graphs showing ri CD40-TRAF2,3 blocking peptide protects against loss of ganglion neurons and inflammation when administered after retinal I/R. One eye from each B6 mouse was subjected to I/R. Non-ischemic eyes were used as controls. Eyes that were subjected to I/R received either ri control peptide or ri CD40-TRAF2,3 blocking peptide 90 min after increase in IOP. Eyes were collected 2 d after I/R. Administration of the blocking peptide protects against ganglion cell loss and infiltration by leukocytes (arrowhead). Original magnification ×400. Scale bar, 50 μm. Number of ganglion cells per mm. Number of leukocytes in the inner retina and vitreous per section. mRNA levels of ICAM-1, KC/CXCL1, NOS2 and COX-2 were assessed by quantitative real time PCR as above. Data shown represent Mean±SEM (7-9 mice per group). P<0.01; *P<0.001. GCL=Ganglion cell layer; IPL=Inner plexiform layer; INL=Inner nuclear layer.

DETAILED DESCRIPTION

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The definitions provided herein are to facilitate understanding of certain terms used frequently herein and are not meant to limit the scope of the present invention.

In the context of the present invention, the term "CD40-mediated disease" refers to an activity of CD40/CD154 (CD40 ligand; CD40L), a signal transduction pathway of CD40/CD154, or an activity or signal transduction pathway that is mediated by CD40/CD154. Thus, a CD40-mediated disease can include a disease where a CD40 activity or signal transduction pathway can be modulated for treatment of a disease. More particularly, the present invention encompasses compositions and methods that modulate a CD40/CD154 activity and/or CD40/CD154 signal transduction pathway to provide a therapeutic benefit or therapeutic activity for treatment of a disease, e.g., an inflammatory disease, disorders of the immune system, or a disease comprising malignant B-cells.

The CD40-mediated disease can include a disease where a CD40 activity or signal transduction pathway can be modulated for treatment of the disease. Examples of CD40-mediated diseases can include, but are not limited to, inflammatory diseases (e.g., atherosclerosis, arteriosclerosis, organ ischemia, rejection of transplanted organs, retinopathy, ischemia-induced retinopathy, diabetes mellitus and complications of this disease, such as diabetic retinopathy, diabetic nephropathy, and diabetic neuropathy), neurodegenerative diseases (e.g., Alzheimer's disease, cerebral ischemia, multiple sclerosis, amyotrophic lateral sclerosis, and Parkinson's disease), autoimmune diseases (e.g., inflammatory bowel disease, systemic lupus erythematosus, rheumatoid arthritis, graft rejection, idiopathic thrombocytopenic purpura, Grave's disease, hemolytic anemia, and inflammatory myopathies), drug-induced autoimmune diseases (e.g., drug-induced lupus, psoriasis, or hyper IgE syndrome), allergic responses (e.g., hay fever or a penicillin allergy), and immune responses to an infectious agent (e.g., a bacterium or virus) as well as diseases or disorders associated with malignant B cells (e.g., B-cell lymphomas).

By "malignant" B cell is intended any neoplastic B cell, including but not limited to B cells derived from lymphomas including low-, intermediate-, and high-grade B-cell lymphomas, immunoblastic lymphomas, non-Hodgkin's lymphomas, Hodgkin's disease, Epstein-Barr Virus (EBV) induced lymphomas, and AIDS-related lymphomas, as well as B-cell acute lymphoblastic leukemias, myelomas, chronic lymphocytic leukemias, acute myeloblastic leukemias, and the like.

As used herein, the term "activity" with reference to CD40 activity refers to a cellular, biological, and/or therapeutic activity or function of CD40. Examples of such activities can include, but are not limited to, signal transduction, interacting or associating with a CD40 ligand or other binding partner (e.g., CD154 or CD40L) or cellular component, and modulating an inflammatory response or process, including atherosclerosis.

As used herein, the term "inflammatory disease" refers to a disease characterized by activation of the immune system to abnormal levels that lead to the disease. An inflammatory disease can include a state in which there is a response to tissue damage, cell injury, an antigen, an infectious disease, and/or some unknown cause. Symptoms of inflammation may include, but are not limited to, cell infiltration and tissue swelling.

As used herein, the term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, all "mimetic" and "peptidomimetic" polypeptide forms, and retro-inversion peptides (also referred to as all-D-retro or retro-enantio peptides).

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

As used herein, the term "antibody" refers to whole antibodies, e.g., of any isotype (IgG, IgA, IgM, IgE, etc.) and includes fragments thereof, which are also specifically reactive with a target polypeptide. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain polypeptide. Non-limiting examples of such proteolytic and/or recombinant fragments include Fab, F(ab')$_2$, Fab', Fv, and single chain antibodies (scFv) containing a V[L] and/or V[H] domain joined by a peptide linker. The scFv's may be covalently or non-covalently linked to form antibodies having two or more binding sites. The term "antibody" also includes polyclonal, monoclonal, or other purified preparations of antibodies, recombinant antibodies, monovalent antibodies, and multivalent antibodies. Antibodies may be humanized and may further include engineered complexes that comprise antibody-derived binding sites, such as diabodies and triabodies.

As used herein, the term "subject" refers to any warm-blooded organism including, but not limited to, human beings, pigs, rats, mice, dogs, goats, sheep, horses, monkeys, apes, rabbits, cattle, etc.

As used herein, the terms "treatment," "treating," or "treat" refer to any treatment of a CD40-mediated disease in a subject including, but not limited to, preventing the disease from developing, inhibiting disease development, arresting development of clinical symptoms associated with the disease, and/or relieving the symptoms associated with the disease.

As used herein, the term "effective amount" refers to a dosage of a first and/or second agent, which is sufficient to provide treatment for a CD40-mediated disease. The effective amount can vary depending on the subject, the disease being treated, and the treatment being effected.

As used herein, the term "therapeutically effective amount" refers to that amount of a first and/or second agent that results in amelioration of symptoms or a prolongation of survival in a subject. A therapeutically relevant effect relieves to some extent one or more symptoms of a CD40-mediated disease or condition (e.g., an inflammatory disease) or returns to normal, either partially or completely, one or more physiological or biochemical parameters associated with or causative of the disease.

The present invention relates generally to methods for treating CD40-mediated diseases, and more particularly to methods for treating CD40-mediated inflammatory diseases. It was found that: (1) blocking the function of the TNF receptor associated factor 2,3 (TRAF2,3) binding domains (or sites) and/or TRAF6 binding domains (or sites) of CD40 can impair CD40-induced effector responses associated with the development of inflammation; and (2) simultaneous blockade of the TRAF2,3 binding domain and IL-1β cooperate to control CD40-driven tissue factor (TF) upregulation. For example, it was found that: (1) incubation of human aortic endothelial cells (HAEC) with a TRAF 2 inhibitor AAVALLPAVLLALLAP SNTAAPVQETLHG (SEQ ID NO: 1) and a TRAF 6 inhibitor AAVALLPAVLLALLAP APHPKQEPQEIDFPDD (SEQ ID NO: 2), caused a marked inhibition in intracellular adhesion molecule-1 (ICAM-1) and vascular cell adhesion molecule-1 (VCAM-1) upregulation and monocyte chemotactic protein-1 (MCP-1) and tissue factor production and secretion in response to CD154; and (2) that a neutralizing monoclonal antibody directed against IL-1β blocks monocytic cell production of tissue factor driven by TRAF6.

In accordance with one aspect of the invention, a method for treating a CD40-mediated diseases, such as atherosclerosis and retinopathy (e.g., diabetic retinopathy, ischemic retinopathy), in a subject can include administering to a cell expressing CD40 a first agent that inhibits binding of a native TRAF 2 polypeptide to a cytoplasmic part of CD40. As used herein, the term "cytoplasmic part of CD40" refers to a part of CD40 comprising the 62 carboxy-terminal amino acids of human CD40 (amino acid 216-277), or the homologous mouse sequence, or another homologous sequence with similar biological activity.

The cell can include any immune or non-immune cell of the subject that expresses CD40 on the cell surface. One example of an immune cell that can express CD40 on the cell surface can include an antigen-presenting cell (APC), such as B-cell. APCs can include any cell that presents on its surface an antigen in association with a MHC or portion thereof, or, one or more non-classical MHC molecules, or a portion thereof. Examples of APCs can include, but are not limited to, Langerhans cells, veiled cells of afferent lymphatics, dendritic cells, interdigitating cells of lymphoid organs, and mononuclear cells, such as macrophages, microglia. Non-immune CD40-expressing cells can include, but are not limited to, endothelial cells, smooth muscle cells, epithelial cells, neurons, Muller retinal cells and other glial cells, such as astrocytes.

The first agent can include any polypeptide, polynucleotide, small molecule, or combination thereof that is capable of inhibiting binding of a native TRAF 2 to a cytoplasmic part of CD40 (e.g., TRAF 2,3 binding site) but does not inhibit binding of CD40 ligand (CD40L) to CD40 of the cells. The first agent can inhibit at least one of the following pro-inflammatory responses: upregulation of VCAM-1 or ICAM-1 from the cells, or production of chemokines such as MCP-1 or CXCL1 or production of tissue factor, or metalloproteinases, or nitric oxide, or prostaglandins from the cells. Advantageously, the first agent does not promote platelet aggregation or thrombosis in the subject and the cell-mediated immune response of the subject is substantially unimpaired.

In one example, the first agent can include a TRAF 2 inhibitor that competitively inhibits binding of the native TRAF 2 polypeptide to a TRAF 2,3 binding domain located on the cytoplasmic part of CD40. The TRAF 2 inhibitor can include a cell-permeable polypeptide comprising a membrane transduction domain (MTD) polypeptide and a polypeptide comprising an amino acid sequence substantially homologous to the amino acid sequence of TRAF 2 binding domain (e.g., TRAF 2,3 binding site). Generally, MTDs consist of positively-charged, short peptide sequences that have the ability to cross a plasma membrane to the cell interior in an energy- and receptor-independent manner (i.e., via endocytosis). For example, the MTD can facilitate uptake of the amino acid sequence substantially homologous to the amino acid sequence of a TRAF binding domain into a cell (e.g., a human or animal cell) or tissue. It should be appreciated however, that MTDs which cross the plasma membrane in ways other than endocytosis are also included within the scope of the present invention.

Numerous types of MTDs are known in the art and can be included as part of the cell-permeable polypeptide. For example, the MTD can include Kaposi fibroblast growth factor (K-FGF). In particular, a region of K-FGF, such as the hydrophobic region having the amino acid sequence AAVALLPAVLLALLAP (SEQ ID NO: 3), can be used to facilitate translocation of the amino acid sequence substantially homologous to the amino acid sequence of a TRAF binding domain into a cell.

Another example of the MTD can include the VP22 tegument protein of herpes simplex virus type 1 (HSV-1). An important property VP22 is that when applied to a surrounding medium, VP22 may be taken up by cells and accumulate in the nucleus of the cells. Fusion proteins of VP22 conjugated to GFP, thymidine kinase protein, and p53, for example, have been targeted to cells in this manner. The VP22 polypeptide can have an amino acid sequence substantially similar to native mammalian VP22 polypeptide. For example, a VP22 polypeptide can have the amino acid sequence NAATATRGRSAASRPTERPRAPARSASR-PRRPVE (SEQ ID NO: 4). Other amino acid and polynucleotide sequences corresponding to VP22 polypeptides, such as homologs, mutants, variants, and/or fragments thereof are known in the art and are available through the GenBank sequence database, for example.

Another example of the MTD can include the human immunodeficiency virus (HIV) trans-activating protein (Tat). Tat is an 86-102 amino acid long protein involved in HIV replication. Tat can translocate through a plasma membrane and reach the cell nucleus, where it then transactivates the viral genome. One particular sequence of amino acids 48-60 CGRKKRRQRRRPPQC (SEQ ID NO: 5) from Tat is important for translocation, nuclear localization, and trans-activation of cellular genes. Numerous other Tat-derived short membrane translocation domains and sequences have been identified that possess translocation activity. Examples of such domains can include amino acids 37-72 and 49-58 RKKRRQRRR (SEQ ID NO: 6). Any of these fragments may be used alone or in combination with each other to enable translocation of the cell-permeable polypeptide into a cell.

Tat-derived polypeptides lacking the cysteine rich region (amino acids 22-36) and the carboxyl terminal domain (amino acids 73-86) have been also found to be particularly effective in translocation. Absence of the cysteine-rich region and the carboxy-terminal domain can prevent spurious trans-activation and disulfide aggregation. In addition, the reduced size of the transport polypeptide can minimize interference with the biological activity of the molecule being transported and increase uptake efficiency. Accordingly, use of MTDs comprising such Tat-derived polypeptides (i.e., those lacking the carboxyl terminal domain and/or the cysteine rich-region) may be used to improve the translocation efficiency of the cell-permeable polypeptide.

The MTD can alternatively include all or part of the Drosophila Antennapedia (Antp) homeodomain (HD) protein. For example, the MTD may comprise the third helix of Antp-HD, which has cell penetration properties. The region responsible for translocation in Antp-HD has been localized to amino acids 43-58 (i.e., the third helix), a 16 amino acid-long peptide rich in basic amino acids. The third helix has the amino acid sequence RQIKIWFQNRRMKWKK (SEQ ID NO: 7). This polypeptide has been used to direct biologically active substances to the cytoplasm and nucleus of cells in culture. Accordingly, the MTD of the present invention may comprise an Antp-HD polypeptide, an Antp-HD homolog, an Antp-HD variant, and/or an Antp-HD fragment, such as a fragment containing the third helix of Antp-HD, for example.

Another example of the MTD can include polypeptides having a high arginine content. For example, polyarginine polypeptides of about 6 to 11 residues in length can have translocating activities similar to Tat (Wender, P. A., et al., Proc. Natl Acad. Sci. USA. 97:13003-13008 (2000); Suzuki et al., 2001; Masayuki et al., 2001; and Han, K., et al., Mol. Cells 12:267-271 (2001)). For example, the polyarginine polypeptides can have structures selected from the group (ZYZ)nZ, (ZY)nZ, (ZYY)nA and (ZYYY)nZ, where Z is L-arginine or D-arginine, Y is an amino acid other than one that contains an amidino or guanidino moiety, and n is an integer ranging from 2 to 10. U.S. Patent Pub. No. 2003/0032593 A1 describes translocating peptides having spaced arginine moieties.

The MTD can include at least one signal sequence. Signal sequences of polypeptides are recognized by acceptor proteins that aid in mobilizing pre-proteins from the translation machinery to the membrane of appropriate intracellular organelles. Signal sequence-based translocators are thought to function by acting as a leader sequence ("leading edge") to carry polypeptides and proteins into cells. The core hydrophobic region of a signal peptide sequence may be used as a carrier for cellular import of, for example, intracellular proteins. Synthetic membrane translocation domains and amino acid sequences containing such hydrophobic regions may also be able to translocate into cells. One particular hydrophobic region, known as the h region, consists of 7-16 non-conserved amino acids and has been identified in 126 signal peptides ranging in length from 18-21 amino acids. Accordingly, a cell-permeable polypeptide of the present invention may include any one or combination of these or other known signal sequences.

MTDs comprising signal sequence-based peptides coupled to nuclear localization sequences (NLSs) may also be used as part of the cell-permeable polypeptide. For example, the peptide signal sequence-based peptide I is a chimera of the hydrophobic terminal domain of the viral gp41 protein and the NLS from the 5V40 large antigen, and has been found to be active in membrane translocation. Additionally, the peptide signal sequence-based peptide II is derived from the nuclear localization signal of NF-κB p50 and USF2. Any one or combination of known membrane translocation sequences, including those provided herein may be used alone or in combination with the cell-permeable polypeptide of the present invention to deliver the amino acid sequence substantially homologous to the amino acid sequence of a TRAF binding domain into a cell.

The cell-permeable polypeptide may also include transportan. Transportan is a fusion between the neuropeptide galanin and the wasp venom peptide mastoparan. It can be localized in both the cytoplasm and nucleus, and may comprise the amino acid sequence GWTLNSAGYLLKINLKALAALAKKIL (SEQ ID NO: 8). The mechanism of cell penetration by transportan is not clear; however, it is known to be energy-independent and that receptors and endocytosis are not involved. Accordingly, the cell-permeable polypeptide of the present invention can comprise transportan, transportan homologues, and/or fragments thereof. For example, a cell-permeable polypeptide comprising a transportan variant may include N-terminal deletions of about 1-6 amino acids as such deletions are known to increase translocational activity of transportan.

The MTD can also include an amphiphilic model peptide. Amphiphilic model peptide is a synthetic 18-mer, KLALKLALKALKAALKLA (SEQ ID NO: 9). The only essential structural requirement for amphiphilic model peptides is a length of four complete helical turns. The amphiphilic model peptide can cross the plasma membrane of various cell types, including mast and endothelial cells, for example, by both energy-dependent and energy-independent mechanisms. The translocation behavior of amphiphilic model peptide shows analogy to several membrane translocation domain sequences including, for example, Antp-HD and Tat. Accordingly, the MTD of the present invention can comprise any amphiphilic model peptide, homolog, variant, and/or fragment thereof.

While any of the MTDs (including domains and/or sequences and/or fragments thereof exhibiting membrane translocation activity) provided above may be used for the purpose of generating a cell-permeable polypeptide, it should be appreciated that other variations are also possible. For example, variations such as mutations (e.g., point mutations, deletions, insertions, etc.) of any of the sequences disclosed herein may be employed, provided that some membrane translocation activity is retained. Furthermore, it will be appreciated that homologues of MTDs from any other organism, including those of synthetic origin, may also be used.

The polypeptide comprising the amino acid sequence substantially homologous to the TRAF2,3 binding domain can be SNTAAPVQETLHG (SEQ ID NO: 10). It will be appreciated that variations of SEQ ID NO: 10 are possible, provided that the polypeptide can still competitively inhibit binding of native TRAF2 polypeptides to the TRAF2,3 binding domain of CD40.

In some embodiments, polypeptides that are substantially homologous to the TRAF2,3 binding domain and can competitively inhibit binding of native TRAF2 polypeptides to the TRAF2,3 binding domain of CD40 (i.e., CD40-TRAF2,3 blocking peptide) can have an amino acid sequence at least about 70%, about 75%, about 80%, about 85%, about 90%, or about 95% identical to SEQ ID NO: 10. For example, the polypeptide can have the amino acid sequence of NTAAHVQETLHG (SEQ ID NO: 11). SEQ ID NO: 11 includes a deletion of the serine residue of SEQ ID NO: 10 that mismatches human and mouse sequences.

Other examples of polypeptides that can have an amino acid sequence at least about 70%, about 75%, about 80%, about 85%, about 90%, or about 95% identical to SEQ ID NO: 10 and can competitively inhibit binding of native TRAF2 polypeptides to the TRAF2,3 binding domain of CD40 can have the following amino acid sequences: SNTAAHVQETLHG (SEQ ID NO: 21), SNTAAHIQETLHG (SEQ ID NO: 22), SNTAAHVQESLHG (SEQ ID NO: 23), SNTAAHIQESLHG (SEQ ID NO: 24), SNTAAPIQETLHG (SEQ ID NO: 25), SNTAAPIQESLHG (SEQ ID NO: 26), and SNTAAPVQESLHG (SEQ ID NO: 27).

The CD40-TRAF2,3 blocking peptides comprising the amino acid sequence substantially homologous to the TRAF2,3 binding domain can be SNTAAPVQETLHG (SEQ ID NO: 10). It will be appreciated that variations of SEQ ID NO: 10 are possible, provided that the polypeptide can still competitively inhibit binding of native TRAF2 polypeptides to the TRAF2,3 binding domain of CD40.

In other embodiments, CD40-TRAF2,3 blocking peptides that are substantially homologous to the TRAF2,3 binding domain and can competitively inhibit binding of native TRAF2 polypeptides to the TRAF2,3 binding domain of CD40 can have an amino acid sequence of $X_1X_2QEX_3$ (SEQ ID NO: 28);

wherein $X_1$ is P or H;
$X_2$ is V, I, or T;
$X_3$ is T or S.

For example, the CD40-TRAF2,3 blocking peptides can have the amino acid sequence of PVQET (SEQ ID NO: 29).

Other examples of polypeptides that can include the amino acid sequence of SEQ ID NO: 28 and can competitively inhibit binding of native TRAF2 polypeptides to the TRAF2,3 binding domain of CD40 can have the following amino acid sequences:

```
                            (SEQ ID NO: 30)
    DLPGSNTAAPVQET, (SEQ ID NO: 31)
    NTAAPVQETLHGC, (SEQ ID NO: 32)
    NTAAPVQETLHG, (SEQ ID NO: 33)
    NTAAPVQETLH, (SEQ ID NO: 34)
    NTAAPVQETL,
    or (SEQ ID NO: 35)
    NTAAPVQET.
```

The CD40-TRAF2,3 blocking peptides can be subject to various changes, substitutions, insertions, and deletions where such changes provide for certain advantages in its use. In this regard, the CD40-TRAF2,3 blocking peptides that block TRAF2 binding to CD40 can be substantially homologous with, rather than be identical to, the sequence of a recited peptide where one or more changes are made and it retains the ability to function as specifically block TRAF2 binding to CD40.

The CD40-TRAF2,3 blocking peptides can be in any of a variety of forms of polypeptide derivatives, that include amides, conjugates with proteins, cyclized polypeptides, polymerized polypeptides, retro-inverso peptides, analogs, fragments, chemically modified polypeptides, and the like derivatives.

Retro-inverso peptides are linear peptides whose amino acid sequence is reversed and the α-center chirality of the amino acid subunits is inverted as well. These types of peptides are designed by including D-amino acids in the reverse sequence to help maintain side chain topology similar to that of the original L-amino acid peptide and make them more resistant to proteolytic degradation. D-amino acids represent conformational mirror images of natural L-amino acids occurring in natural proteins present in biological systems. Peptides that contain D-amino acids have advantages over peptides that just contain L-amino acids. In general, these types of peptides are less susceptible to proteolytic degradation and have a longer effective time when used as pharmaceuticals. Furthermore, the insertion of D-amino acids in selected sequence regions as sequence blocks containing only D-amino acids or in-between L-amino acids allows the design of peptide based drugs that are bioactive and possess increased bioavailability in addition to being resistant to proteolysis. Furthermore, if properly designed, retro-inverso peptides can have binding characteristics similar to L-peptides.

In some embodiments, retro-inverso CD40-TRAF2,3 blocking peptides (i.e., ri CD40-TRAF2,3 blocking peptides) that can competitively inhibit binding of native TRAF2 polypeptides to the TRAF2,3 binding domain of CD40 can have an amino acid sequence of $X_1EQX_2X_3$ (SEQ ID NO: 38);

wherein $X_1$ is T or S;

$X_2$ is V, I, or T;

$X_3$ is P or H.

For example, the ri CD40-TRAF2,3 blocking peptides can have the amino acid sequence of TEQVP (SEQ ID NO: 39).

Other examples of ri CD40-TRAF2,3 blocking peptides that can include the amino acid sequence of SEQ ID NO: 38 and can competitively inhibit binding of native TRAF2 polypeptides to the TRAF2,3 binding domain of CD40 can have the following amino acid sequences:

```
TEQVPAATNSGPLD,                       (SEQ ID NO: 40)

TEQVPAATNSGPL,                        (SEQ ID NO: 41)

TEQVPAATNSGP,                         (SEQ ID NO: 42)

TEQVPAATNSG,                          (SEQ ID NO: 43)

TEQVPAATNS,                           (SEQ ID NO: 44)
or

TEQVPAATN.                            (SEQ ID NO: 45)
```

The term "analog" includes any polypeptide having an amino acid residue sequence substantially identical to a sequence specifically shown herein in which one or more residues have been conservatively substituted with a functionally similar residue and that specifically block TRAF2 binding to CD40 as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

The term "fragment" refers to any subject polypeptide having an amino acid sequence shorter than that of a polypeptide whose amino acid sequence is shown herein.

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases, such as sodium hydroxide, ammonium hydroxide, potassium hydroxide and the like; and organic bases such as mono-, di- and tri-alkyl and arylamines (e.g., triethylamine, diisopropylamine, methylamine, dimethylamine and the like) and optionally substituted ethanolamines (e.g., ethanolamine, diethanolamine and the like).

The CD40-TRAF2,3 blocking peptides can be synthesized by any of the techniques that are known to those skilled in the peptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

The TRAF 2 inhibitor may be prepared using techniques known in the art. For example, a cell-permeable polypeptide can be chemically synthesized by synthesizing a MTD and CD40-TRAF2,3 blocking peptide, and then fusing the respective polypeptides using known techniques (see, e.g., Mukundan, L. et al., J. Immunol. 174:1081-1090 (2005); Tsao, D. H. et al., Mol. Cell 5:1051-1057 (2000)).

One example of a TRAF 2 inhibitor cell-permeable polypeptide comprising a MTD and a CD40-TRAF2,3 blocking peptide is SEQ ID NO: 1. Another example of a TRAF 2 inhibitor cell-permeable polypeptide comprising a MTD and a CD40-TRAF2,3 blocking peptide is SNTAAPVQETLHG YGRKKRRQRRR (SEQ ID NO: 12). Still another example of a TRAF 2 inhibitor cell-permeable polypeptide comprising a MTD and a CD40-TRAF2,3 blocking peptide is NTAAHVQETLHG YGRKKRRQRRR (SEQ ID NO: 13). Other examples of TRAF 2 inhibitor cell-permeable polypeptides comprising a MTD and a CD40-TRAF2,3 blocking peptide are AAVALLPAVLLALLAP SNTAAPVQETLHG (SEQ ID NO: 36) or NTAAPVQETLHG YGRKKRRQRRR (SEQ ID NO: 37). Still other examples of TRAF 2 inhibitor cell-permeable polypeptides comprising a MTD and a CD40-TRAF2,3 blocking peptide are GHLTEQVPAATN PALLALLVAPLLAVAA (SEQ ID NO: 46), GHLTEQVHAATN PALLALLVAPLLAVAA (SEQ ID NO: 47), RRRQRRKKRGY GHLTEQVPAATN (SEQ ID NO: 48), or RRRQRRKKRGY GHLTEQVHAATN (SEQ ID NO: 49).

It will be appreciated that the cell permeable polypeptides can also be chemically cross-linked or coupled to larger peptides and proteins. The coupling may be permanent or transient, and may involve covalent or non-covalent interactions. Direct linkage, for example, may be achieved by localizing a functional group, such as a hydroxyl, carboxy, or amino group on the peptides. Indirect linkage can be achieved through a linking moiety, such as one or more of bi-functional cross-linking agents, for example. Coupling technologies are well known in the art.

Other methods for forming fusion proteins are known in the art and can include, for example, fusing a MTD to an amino acid sequence substantially homologous to the amino acid sequence of a TRAF binding domain using a suitable host, such as a eukaryotic or prokaryotic cell. For example, a cDNA encoding a cell-permeable polypeptide having SEQ ID NO:1 may be constructed to include nucleic acid sequences encoding both a K-FGF MTD and the amino acid sequence of SEQ ID NO: 10. The nucleic acid sequences may be in-frame and may be located downstream of an N-terminal leader sequence (e.g., a sequence comprising a 6-Histidine tag). The N-terminal leader sequence may enable purification of the expressed cell-permeable polypeptide using methods known in the art.

Additionally or optionally, the TRAF 2 inhibitor can include a linker sequence that operably couples the MTD with the amino acid sequence that is substantially homologous to a TRAF binding domain. Such a linker sequence may include a sequence of amino acids susceptible to cleavage by native enzymes (e.g., proteases), for example. The linker may comprise amino acid residues and/or hydrocarbon chains capable of connecting the MTD and the amino acid sequence that is substantially homologous to a TRAF binding domain, for example, via peptide bonds. Useful linkers can also include natural and unnatural biopolymers. A non-exclusive example of a natural linker includes L-oligopeptides, while examples of unnatural linkers include D-oligopeptides, lipid oligomers, liposaccharide oligomers, peptide nucleic acid oligomers, polylactate, polyethylene glycol, cyclodextrin, polymethacrylate, gelatin, and oligourea.

Additionally, the TRAF 2 inhibitor can be modified by natural processes, such as posttranslational processing, and/or by chemical modification techniques, which are known in the art. Modifications may occur anywhere in the polypeptide including the polypeptide backbone, the amino acid side-chains and the amino or carboxy termini. It will be appreciated that the same type of modification may be present in the same or varying degrees at several sites in a given polypeptide. The polypeptides may be branched as a result of ubiquitination, and they may be cyclic, with or without branching. Cyclic, branched and branched cyclic polypeptides may result from posttranslational natural processes or may be made by synthetic methods. Modifications comprise for example, without limitation, acetylation, acylation, addition of acetomidomethyl (Acm) group, ADP-ribosylation, amidation, covalent attachment to flavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, $2^{nd}$ Ed., T. E. Creighton, W. H. Freeman and Company, New-York, 1993).

Other type of polypeptide modification may include for example, amino acid insertion (i.e., addition), deletion and substitution (i.e., replacement), either conservative or non-conservative (e.g., D-amino acids) in the polypeptide sequence where such changes do not substantially alter the overall bioactivity of the polypeptide.

Various delivery systems can be used to administer the first agent to a cell of the subject to inhibit TRAF 2 binding to CD40. Examples of such delivery systems can include, but are not limited to, encapsulation in liposomes, microparticles, microcapsules, recombinant cells capable of expressing the agent, receptor-mediated endocytosis, construction of a nucleic acid as part of a retroviral or other vector, commercially available products (e.g., the CHARIOT protein delivery system), and the like. Methods of introduction into the subject can include, but are not limited to, intradermal, intramuscular, intraperitoneal, intravenous, subcutaneous, intranasal, epidural, and oral routes. The agent may be administered by any convenient route, for example, by infusion or bolus injection, by absorption through epithelial, or by absorption through mucocutaneous linings (e.g., oral mucosa, rectal and intestinal mucosa, etc.). Administration can be systemic or local. Pulmonary administration can also be employed, e.g., by use of an inhaler or nebulizer and formulation with an aerosolizing agent.

In another aspect of the invention, the first agent can be a small molecule or small chemical entity that is capable of inhibiting binding of a native TRAF 2 to a cytoplasmic part of CD40 (e.g., TRAF 2,3 binding site). Small molecules that inhibit binding of native TRAF 2 to a cytoplasmic part of CD40 can be readily determined using a cell-based assays that measure the effects of molecules on intracellular pathways.

By way of example, an endothelial cell line mHEVc that lacks endogenous CD40, can be genetically engineered to express CD40 such that is does not recruit TRAF6 (ΔT6). The ΔT6 mHEVc can only signal through the TRAF2,3 binding site when stimulated with CD154. The ΔT6 mHEVc can also be stably transfected with an NF-κB response element upstream of a firefly luciferase plasmid. Activation of NF-κB is a critical mediator of the cellular effects of CD40-TRAF signaling. The ΔT6 mHEVc can be plated in a 96 well plate ($4\times10^4$ cells/well) followed by pre-incubation for 3 h with compounds that are potentially capable of inhibiting binding of a native TRAF 2 to a cytoplasmic part of CD40. Cells can then be stimulated with recombinant CD154 (3 µg/ml). Activation of NF-κB can be assessed by performing a luciferase assay. Cells incubated with CD154 alone (no drug) and cells incubated with medium alone (no CD154) will be positive and negative controls (all run in quadruplicate). mHEVc can then be incubated with increasing concentrations of the tested molecules followed by a commercially available MTT assay. Identified molecules that have no evidence of toxic effects can then be tested at different concentrations to determine the IC50 for inhibition of CD40-induced luciferase activity.

Small molecules initially identified by the T6 mHEVc can then be tested or screened to determine if they inhibit CD40-dependent pro-inflammatory responses in retinal cells. For example, mouse retinal endothelial cells and mouse microglia (available in our laboratory) can be pre-incubated with increasing concentrations of the small molecules followed by stimulation with CD154. Using FACS, ELISA and western blot, endothelial cells can then be tested for ICAM-1 upregulation, production of MCP-1 and VEGF and microglia for expression of NOS2 and COX-2. Nitric oxide and PGE2 can be measured by Griess reaction and ELISA respectively. To determine if the small molecules specifically inhibit CD40 signaling, they can also be tested with cells that are stimulated with IFN-γ and LPS.

In a further aspect of the invention, the first agent can include a physiologically acceptable diluent or a pharmaceutically acceptable carrier, such as sterile water or sterile isotonic saline. As used herein, the term "pharmaceutically acceptable carrier" refers to any and all solvents, dispersion media, coatings, antibacterial and antifungal agents, isotonic and absorption delaying agents, and the like, compatible with administration of the formulation to a subject. The appropriate carrier will be evident to those skilled in the art and will depend in part upon the route of administration.

Additional components that may be present with the formulation can include adjuvants, preservatives, chemical stabilizers, and/or other proteins. Typically, stabilizers, adjuvants, and preservatives are optimized to determine the best formulation for efficacy in a subject. Examples of preservatives can include, but are not limited to, chlorobutanol, potassium sorbate, sorbic acid, sulfur dioxide, propyl gallate, the parabens, ethyl vanillin, glycerin, phenol, and parachlorophenol. Stabilizing ingredients can include, for example, casamino acids, sucrose, gelatin, phenol red, N-Z amine, monopotassium diphosphate, lactose, lactalbumin hydrolysate, and dried milk.

Other components of the formulation can include, for example, surface active substances (e.g., hexadecylamine, octadecylamine, octadecyl amino acid esters, lysolecithin, dimethyl-dioctadecylammonium bromide), methoxyhexadecyiglycerol, pluronic polyols, polyamines (e.g., pyran, dextransulfate, poly IC, carbopol), oil emulsions, mineral gels (e.g., aluminum phosphate), liposomes, polysaccharides, lipopolysaccharides, and/or other polymers.

The first agent can be delivered to a cell expressing CD40 at amount effective to inhibit activation of the cell by CD154. Administering an effective amount of the agent to a CD40-expressing cell can inhibit activation of the cell by CD154 by blocking the interaction (i.e., binding) of native TRAF polypeptides with their respective TRAF binding domains. Preventing or blocking the interaction of native TRAF polypeptides with their respective TRAF binding domains can in turn disrupt the CD40-signaling pathway and reduce or inhibit the expression of inflammatory molecules.

In an example of the method, a therapeutically effective amount of a first agent comprising a TRAF 2 inhibitor (e.g., SEQ ID NO: 1, SEQ ID NO: 12, SEQ ID NO: 13) can be administered to subject suffering from atherosclerosis. The TRAF 2 inhibitor can be prepared using a known method, such as synthetic peptide synthesis. The TRAF 2 inhibitor can then be administered to the subject via local or systemic injection. For example, the TRAF 2 inhibitor can be injected into a coronary artery having an atherosclerotic lesion.

Upon injection into the coronary artery, the MTD of the TRAF 2 inhibitor can contact the cell membrane of an endothelial cell, which lines a portion of the arterial surface. The TRAF 2 inhibitor can then be translocated across the plasma membrane of the endothelial cell via an energy- and receptor-independent mechanism. Entry of the TRAF 2 inhibitor into the cytoplasm of the endothelial cell allows the portion of the TRAF 2 inhibitor comprising an amino acid sequence substantially homologous with TRAF 2,3 binding site to bind to TRAF 2 and inhibit binding of TRAF2 to the TRAF2,3 binding domain. Inhibition of TRAF 2 binding to TRAF 2,3 binding domain can decrease or inhibit the CD40-signaling pathway in the endothelial cell and thereby decrease or inhibit the activity or expression of pro-inflammatory molecules, such as VCAM-1, ICAM-1, MCP-1, RANTES, IL-8, metalloproteinases, tissue factor, NOS2, COX-2, and VEGF. Decreasing or inhibiting the activity or expression of such pro-inflammatory molecules can decrease or inhibit the pro-atherogenic response in the subject.

The present invention also relates to a method of treating a CD40-mediated disease in a subject by administering to a cell expressing CD40 a first agent that inhibits the binding of a native TRAF 2 polypeptide to a TRAF 2,3 binding domain and a second agent that inhibits the activity of IL-1.

In an aspect of the invention, the first agent can include a TRAF 2 inhibitor as described above. The second agent can include any polypeptide, polynucleotide, small molecule, or combination thereof that is capable of inhibiting IL-1 activity. In one aspect, the second agent can include a TRAF 6 inhibitor that inhibits binding of native TRAF 6 polypeptide to a cytoplasmic part of CD40. TRAF 6 binding to the TRAF6 binding site of CD40 can control IL-1 and other pro-inflammatory cytokine production by macrophages. Inhibition of the TRAF 6 binding the TRAF 6 binding site can therefore inhibit IL-1 production and/or IL-1 activity.

The TRAF 6 inhibitor can be a cell permeable polypeptide that includes a MTD polypeptide and a polypeptide comprising an amino acid sequence substantially homologous to the amino acid sequence of a TRAF 6 binding domain. The MTD can include any one or combination of the MTDs described above, so long as the MTD has the ability to cross a plasma membrane into a cell interior in an energy- and receptor-independent manner (i.e., via endocytosis). In an example of the present invention, the MTD of a cell-permeable polypeptide comprising the second agent can include K-FGF. It should be appreciated however, that MTDs which cross the plasma membrane in ways other than endocytosis are also included within the scope of the present invention.

The polypeptide comprising the amino acid sequence that is substantially homologous to the amino acid sequence of a TRAF 6 binding domain can be APHPKQEPQEIDFPDD (SEQ ID NO: 14). It will be appreciated that sequence variations of SEQ ID NO: 14 are possible, provided that the polypeptide can still competitively inhibit binding of native TRAF6 polypeptides to the TRAF6 binding domain of CD40. For example, variations of the amino acid sequence of SEQ ID NO: 4 that can competitively inhibit binding of TRAF 6 polypeptides to the TRAF 6 binding domain can include KQEPQEIDFPDD (SEQ ID NO: 15), KQEPQEINFPDDL (SEQ ID NO: 16), KQEAQEINFD(E,F,G,H)DDL (SEQ ID NO: 17). It will be appreciated that the TRAF 6 can include other variations as long as these other variations inhibit binding of TRAF 6 polypeptides to TRAF 6 binding domain of CD40.

As described above, the cell-permeable polypeptide may be prepared using techniques known in the art. For example, the cell-permeable polypeptide can be synthesized by fusing a MTD and an amino acid sequence substantially homologous to the TRAF 6 binding domain.

One example of a TRAF 6 inhibitor cell-permeable polypeptide synthesized from a MTD and a polypeptide substantially homologous to TRAF 6 binding domain is SEQ ID NO: 2. Another example of a TRAF 6 inhibitor cell-permeable polypeptide comprising a MTD and a polypeptide substantially homologous to TRAF 6 binding domain is KQEPQEIDFPDD YGRKKRRQRRR (SEQ ID NO: 18). Still other examples of a TRAF 6 inhibitor cell-permeable polypeptides comprising a MTD and a polypeptide substantially homologous to TRAF 6 binding domain are KQEPQEINFPDDL YGRKKRRQRRR (SEQ ID NO: 19) and KQEAQEINFD(E,F,G,H)DDL YGRKKRRQRRR (SEQ ID NO: 20).

Alternatively, the second agent can include a monoclonal or polyclonal antibody capable of inhibiting or decreasing the activity of IL-1. For example, the second agent can include a monoclonal or polyclonal antibody directed against IL-1α or IL-1β or agents that block the function of IL-1 receptors. Examples of anti-IL-1 antibodies are well known in the art and can include those disclosed in PCT Pub. No. WO/9501997, PCT Pub. No. WO/9402627, PCT Pub. No. WO/9006371, U.S. Pat. No. 4,935,343, European Patent No. EP 364778, European Patent No EP 267611, and European Patent No EP 220063.

Administration of the first agent and the second agent to the cell expressing CD40 can have a multi-factorial effect on the pro-inflammatory response of the subject. As described above administering an effective amount of the TRAF 2 inhibitor to a CD40-expressing cell can inhibit activation of the cell by CD154 by blocking the interaction (i.e., binding) of native TRAF polypeptides with their respective TRAF binding domains. Preventing or blocking the interaction of native TRAF polypeptides with their respective TRAF binding domains can in turn disrupt the CD40-signaling pathway and reduce or inhibit the expression of inflammatory molecules.

Delivering the second agent to a cell can also affect the pro-inflammatory response by directly reducing the production and hence activity of IL-1 (e.g., TRAF 6 inhibitor) or inhibiting the activity of IL-1 (IL-1 antibody). By blocking the activity of IL-1, the inflammatory response mediated by IL-1 and TNF-α can thus be decreased or inhibited. Additionally, it is known that blockade of IL-1 does not appear to cause significant susceptibility to opportunistic infections, and CD40-induced dendritic cell activation and macrophage anti-microbial activity are independent of IL-1 activity. Thus, simultaneous blockade of the TRAF2,3 binding domain plus inhibition of IL-1 activity may leave cell-mediated immunity largely unimpaired.

The present invention further relates to a method for treating atherosclerosis in a subject. The method includes administering to the subject a therapeutically effective amount of an agent that inhibits binding of TNF receptor associated factor 2 (TRAF2) to a cytoplasmic portion of CD40 of a cell. The TRAF 2 inhibitor can be prepared using a known method, such as synthetic peptide synthesis. The TRAF 2 inhibitor can then be administered to the subject via local or systemic injection.

The TRAF 2 inhibitor can translocate across the plasma membrane of the endothelial cell and inhibit binding of TRAF2 to the TRAF2,3 binding domain. Inhibition of TRAF 2 binding to TRAF 2,3 binding domain can decrease or inhibit the CD40-signaling pathway in the endothelial cell and thereby decrease or inhibit the activity or expression of pro-inflammatory molecules, such as VCAM-1, ICAM-1, MCP-1, RANTES, IL-8, MMP, TF, NOS2, COX-2, and VEGF. Decreasing or inhibiting the activity or expression of such pro-inflammatory molecules can decrease or inhibit the pro-atherogenic response in the subject.

In a further aspect of the invention, the method of treating atherosclerosis can include administering to the subject a therapeutically effective amount of a second agent that inhibits the production or activity of interleukin-1 (IL-1) in the cell. The second agent can include a cell-permeable polypeptide that competitively inhibits binding of TRAF6 to the TRAF6 binding domain of CD40. The cell-permeable polypeptide can include a membrane transduction domain and a peptide comprising an amino acid sequence substantially homologous to the amino acid sequence of the TRAF6 binding domain. In a further aspect of the invention, the second agent can include an antibody or antibody fragment reactive against IL-1.

The present invention further relates to a method of treating retinopathy (e.g., diabetic retinopathy) in a subject. The method include administering to retinal cells of the subject a therapeutically effective amount of an agent that inhibits binding of TNF receptor associated factor 2 (TRAF2) to a cytoplasmic portion of CD40. The agent can be administered to the cells at an amount effective to inhibit at least one of upregulation of VCAM-1 or ICAM-1 from the cells, or production of MCP-1, CXCL1, nitric oxide, prostaglandins or metalloproteinases from the cells.

In an aspect of the invention, the agent can include a cell-permeable polypeptide that competitively inhibits binding of TRAF2 to the TRAF2,3 binding domain of CD40. The cell-permeable polypeptide can include a membrane transduction domain and a polypeptide comprising an amino acid sequence substantially homologous to the amino acid sequence of the TRAF2,3 binding domain.

In another aspect of the invention, the agent can include at least one of an anti-CD40 antibody or an anti-CD154 antibody that is locally administered to the retina. Examples of antibodies to CD40 are known in the art. See, for example, the sections dedicated to B-cell antigen in McMichael, ed. (1987; 1989) Leukocyte Typing III and IV (Oxford University Press, New York); U.S. Pat. Nos. 5,674,492; 5,874,082; 5,677,165; 6,056,959; WO 00/63395; copending U.S. Provisional Patent Application Ser. No. 60/237,556, titled, "Human Anti-CD40 Antibodies," filed Oct. 2, 2000; Gordon et al. (1988) J. Immunol. 140:1425; Valle et al. (1989) Eur. J. Immunol. 19:1463; Clark et al. (1986) PNAS 83:4494; Paulie et al. (1989) J. Immunol. 142:590; Gordon et al. (1987) Eur. J. Immunol. 17:1535; Jabara et al. (1990) J. Exp. Med. 172:1861; Zhang et al. (1991) J. Immunol. 146:1836; Gascan et al. (1991) J. Immunol. 147:8; Banchereau et al. (1991) Clin. Immunol. Spectrum 3:8; and Banchereau et al. (1991) Science 251:70; all of which are herein incorporated by reference.

In another aspect of the invention, the method can include administering to the subject a therapeutically effective amount of a second agent that inhibits the production or activity of interleukin-1 (IL-1) in the cell.

The following examples are for the purpose of illustration only, and are not intended to limit the scope of the claims, which are appended hereto.

Example 1

Atherosclerosis is an inflammatory disorder triggered by injury to the vasculature. Migration of monocytes (Mo)/macrophages (Mφ) and T cells to the vessel wall is dependent on adhesion molecules and chemokine production. Secretion of pro-inflammatory cytokines and chemokines causes proliferation and migration of smooth muscle cells (SMC) to the intima. Vascular and inflammatory cells produce metalloproteinases (MMPs) that promote plaque rupture. Moreover, tissue factor is induced causing thrombosis.

CD40 is a central mediator of atherosclerosis. CD40 is present on endothelial cells, SMC and Mo/Mφ present in the atheroma. Its counter-receptor, CD514 is expressed in atheromas by $CD4^+$ T cells. Activated platelets also express CD154. The CD40-CD154 pathway is also involved in re-stenosis after angioplasty or stent placement since levels of soluble CD154 are independent predictors of re-stenosis.

CD40 is an attractive target for control of atherosclerosis because: i) CD40 triggers pro-atherogenic responses in vascular and inflammatory cells such as increased expression of adhesion molecules, production of chemokines, expression of MMPs and tissue factor; ii) Progression of atherosclerotic lesions is impaired in $ApoE^{-/-}$ mice that lack CD154; iii) Blocking CD40-CD154 interaction with antibodies inhibits formation of atherosclerotic lesions, prevents evolution of established atheroma and causes a more stable plaque phenotype. Unfortunately, clinical trials of administration of an anti-CD154 mAb revealed that this therapy caused platelet aggregation and thrombosis. These effects are likely caused by activation of platelets via engagement of CD154 expressed on their membrane.

CD40 Signaling

Figure 1:
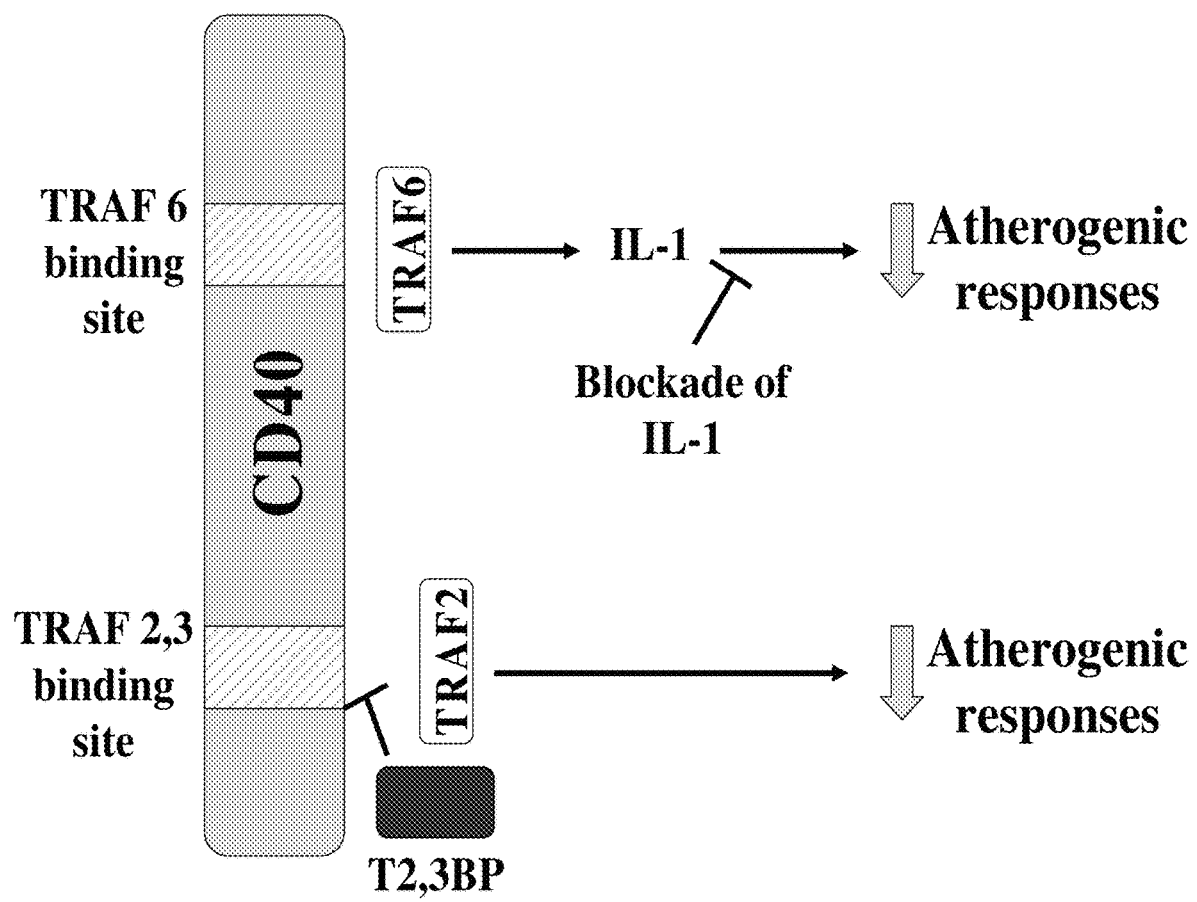
FIG. 1 is a schematic illustration depicting the mechanism underlying the method of the present invention.

Recruitment of TRAF2 and TRAF6 to the TRAF2,3 and TRAF6 binding sites respectively is important for CD40 signaling (TRAF3 is an inhibitor of CD40 signaling) (FIG. 1). TRAF binding sites can control non-overlapping responses. We demonstrated that CD40 stimulation and CD40 plus exogenous TNF-α induced Mφ anti-microbial activity against *Toxoplasma gondii* and *Leishmania major* (Portillo and Subauste, Manuscript in preparation) respectively. Induction of anti-microbial activity is dependent on the TRAF6 binding site. In addition, TRAF6 is central for IL-12 production by dendritic cells stimulated through CD40 and dendritic cell maturation. Thus, CD40-TRAF6 interaction regulates responses key for control of intracellular pathogens.

The identity of the TRAF signals used by CD40 to activate pro-atherogenic responses is unknown. We recently found that the TRAF2,3 site controls important pro-atherogenic responses triggered by CD40. Using transduction of human aortic endothelial cells (HAEC) with retroviral vectors that encode wild type (wt) CD40 or CD40 with mutations at the TRAF2,3, the TRAF6 or the TRAF2,3 plus TRAF6 binding sites we found that TRAFs are essential for CD40-induced upregulation of VCAM-1 and ICAM-1, production of MCP-1 and tissue factor expression by HAEC. Moreover, the mutation that prevents recruitment at the TRAF2,3 site markedly inhibits VCAM-1 and ICAM-1 upregulation and MCP-1 secretion. These results show modulation of TRAF recruitment to the TRAF2,3 site is a novel approach to control atherosclerosis. Importantly, such measure leaves largely unimpaired aspects of cell-mediated immune (CMI) responses key for control of intracellular pathogens.

Cell Permeable Peptides as Manipulators of Intracellular Signaling

We found that preventing CD40-TRAF interaction can become a novel therapeutic strategy for control of atherosclerosis. Peptides that penetrate cells can readily block intracellular protein-protein interactions. Peptides become cell-permeable by expressing protein transduction domains enabling them to enter virtually all cells. In vivo administration of cell-permeable peptides that target a variety of signaling pathways have been shown to be effective therapeutic approaches in animal models of inflammatory bone resorption, lung injury, various cancers and amyotrophic lateral sclerosis.

Peptides that include the amino acid sequence of the TRAF2,3 or TRAF6 binding site of CD40 were found to block appropriate CD40-TRAF interaction and cell signaling (FIGS. 3-8). We also found that a cell-permeable peptide that encodes the TRAF2,3 binding domain of CD40 (TRAF2,3 blocking peptide, T2,3BP) inhibits pro-atherogenic responses in HAEC, SMC and Mφ, and controls vascular injury and atherogenesis in vivo. Indeed, such a peptide markedly impairs VCAM-1 upregulation and MCP-1 secretion by HAEC.

IL-1 is Key for Atherogenesis

CD40 controls pro-atherogenic responses by directly activating intracellular signaling. However, there is likely an additional level of control of atherosclerosis since CD40 triggers pro-inflammatory cytokines (IL-1, TNF-α) that could in turn further amplify pro-atherogenic responses. IL-1 upregulates adhesion molecules, induces chemokine production, stimulates SMC proliferation, MMP and tissue factor expression. Animal models established the importance of IL-1 in atherosclerosis. ApoE$^{-/-}$ mice lacking IL-1β develop less atherosclerotic lesions. LDLR$^{-/-}$ mice crossed with transgenic mice expressing high levels of IL-1 receptor antagonist (IL-1Ra, an inhibitor of IL-1 signaling) were partially protected against atherosclerosis. In addition, administration of human IL-1Ra to ApoE$^{-/-}$ mice decreased the size of atherosclerotic lesions. Moreover, IL-1Ra gene polymorphism is associated with coronary artery disease. Thus, IL-1 is a suitable target for therapy of atherosclerosis.

The CD40-IL-1 interplay supports targeting these pathways for control of atherosclerosis. CD40 not only induces IL-1β but CD40 and IL-1 also synergize for tissue factor expression. Studies on TRAF signaling further support combining blockade of CD40-TRAF and IL-1 for treatment of atherosclerosis. While the TRAF2, 3 binding site controls important atherogenic responses, some of these responses can remain to varying degrees when CD40 no longer signals through the TRAF2, 3 site and signals only through the TRAF6 site.

The TRAF6 binding site controls IL-1 and other pro-inflammatory cytokines production by Mφ, factors that upregulate chemokines and tissue factor. It is not known through which signaling cascade CD40 induces pro-inflammatory cytokines in vascular cells. We found that the TRAF6 site in vascular cells regulates IL-1 and through this cytokine activates atherogenesis (FIG. 1). Thus, blockade of signals downstream of the TRAF2,3 site plus blockade of IL-1 would optimally control vascular injury and atherosclerosis.

Targeting CD40 plus IL-1 has two additional advantages: i) While CD40 induces production of not only IL-1 but also of TNF-α, IL-1 can act as a mediator of TNF-α induced disease. Thus, blocking IL-1 would inhibit atherogenesis triggered by IL-1 and TNF-α. ii) In contrast to inhibition of TNF-α, blockade of IL-1 does not appear to cause susceptibility to opportunistic infections. CD40-induced dendritic cell activation and Mφ anti-microbial activity are IL-1 independent. Thus, combining blockade of CD40-TRAF2,3 plus IL-1 would leave CMI largely unimpaired. In summary, the proposed work will determine whether selective manipulation of signaling cascades central to atherosclerosis can be used as a novel approach to control this disease.

Example 2

The TRAF2,3 Binding Site Controls CD40-Induced VCAM-1 and ICAM-1 Upregulation and MCP-1 Production by Endothelial Cells CD40 activates a variety of signaling cascades. We explored if CD40 acts through TRAFs to induce pro-atherogenic responses. Human aortic endothelial cells (HAEC) were transduced with retroviral vectors that encode either wild type (wt) CD40 or CD40 with mutations at the TRAF2,3 binding site (ΔT2,3), the TRAF6 binding site (ΔT6) or the TRAF2,3 and TRAF6 binding sites (ΔT2,3,6). These mutations block recruitment of appropriate TRAFs to CD40. The retroviral vector (MIEG3) encodes EGFP enabling identification of transduced cells. In contrast to HAEC transduced with the empty vector (MIEG3), those transduced with wt CD40 or CD40 mutants expressed CD40 and levels of expression of this protein were similar among all groups (p=0.5; n=4). Incubation with CD154 (CD40 ligand) upregulated VCAM-1 and ICAM-1 in HAEC that expressed wt CD40. (FIG. 2A-B). This response is TRAF-dependent because it was ablated in HAEC that expressed CD40 that lacked TRAF binding sites (ΔT2,3,6) (91% inhibition; p<0.001; n=3). Next, we determined if preventing the function of the TRAF2,3 binding site affects adhesion molecule upregulation. HAEC that expressed CD40 ΔT2,3 exhibited a markedly impaired VCAM-1 and ICAM-1 upregulation (78% inhibition; n=3; p<0.01). Expression of CD40 ΔT6 also inhibited adhesion molecule upregulation (81% inhibition; n=3; p<0.001). Thus, preventing the function of the TRAF2,3 binding site of CD40 is sufficient to markedly inhibit VCAM-1 and ICAM-1 upregulation in HAEC.

The chemokine MCP-1 is pivotal for atherogenesis. Thus, we examined the role of TRAF signaling in secretion of MCP-1 in response to CD40 stimulation. Similar to the VCAM-1/ICAM-1 data, HAEC that lacked TRAF binding sites (CD40 ΔT2,3,6) were unable to secrete MCP-1 in response to CD40 ligation. (FIG. 2C) Importantly, expression of CD40 ΔT2,3 markedly inhibited MCP-1 secretion (85% inhibition; n=3; p<0.001). Expression of CD40 ΔT6 also impaired MCP-1 production. Thus, our results indicate that the TRAF2,3 binding site plays a major role in controlling crucial events in atherogenesis: adhesion molecule upregulation and MCP-1 secretion.

We examined the role of TRAF signaling in tissue factor expression induced by CD40. HAEC transduced with wt CD40 upregulated tissue factor in response to CD154. This effect was inhibited by a mutation at the TRAF6 binding site and to a lesser extent by one at the TRAF2,3 site. (FIG. 2D) The human monocytic line MonoMac 6 was also transduced with the retroviral vectors. Similar to our results with HAEC, CD154 upregulated tissue factor in MonoMac 6 cells and this effect was inhibited in cells that expressed CD40 ΔT6 (77% inhibition; n=3). Mutation at the TRAF2,3 binding site caused a 50% inhibition in tissue factor upregulation (n=3). In recent studies we have found that both TRAF binding sites control expression of stromelysin-1 (MMP-3) and gelatinase B (MMP-9) in HAEC stimulated with CD154.

A Cell-Permeable CD40-TRAF2,3 Blocking Peptide Markedly Inhibits Adhesion Molecule Upregulation and MCP-1 Secretion by HAEC Stimulated through CD40

We used peptides that consisted of the amino acid sequence of the TRAF2,3 or the TRAF6 binding sites of CD40 fused a protein transduction domain derived from the Kaposi fibroblast growth factor to make the peptides cell-permeable, (SEQ ID NO: 1 or SEQ ID NO: 2, respectively). These peptides have been shown to effectively block the respective TRAF-CD40 interaction and signaling. The cell-permeable peptides did not affect viability of HAEC. Incubation with TRAF2,3 blocking peptide caused a marked inhibition in VCAM-1 upregulation and MCP-1 secretion in response to CD154 (71% inhibition; n=2; p<0.01). (FIG. 3) The TRAF6 blocking peptide also inhibited these responses. Thus, the results obtained with the blocking peptides were similar to those obtained with CD40 mutants. These data support exploring the use of TRAF2,3 blocking peptide as an approach to impair CD40-induced atherogenic responses.

Figure 5:
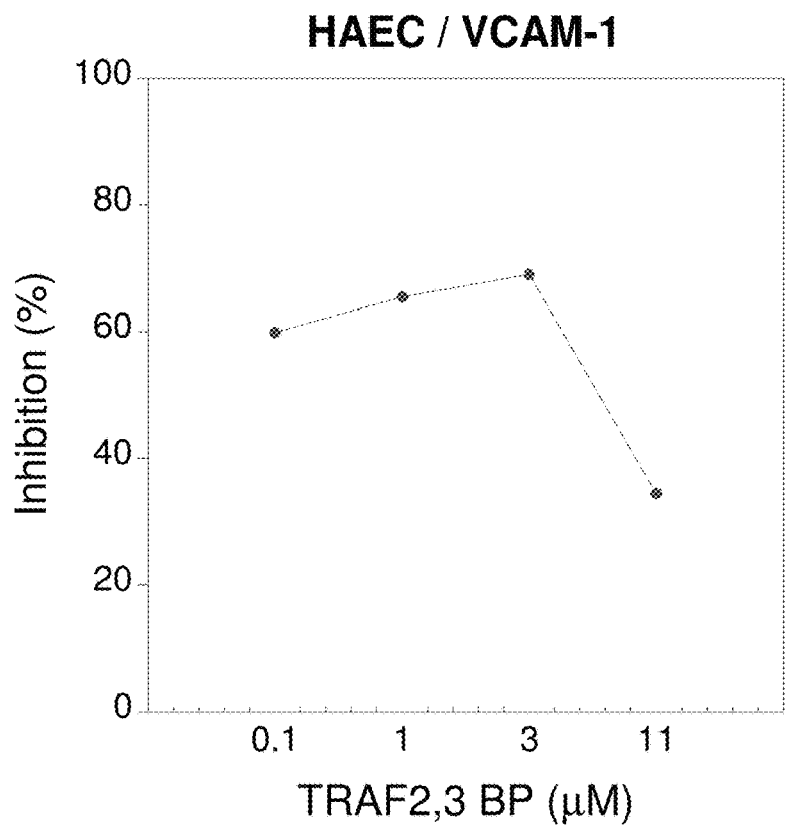
FIG. 5 is a graph showing the effects of second generation TRAF2, 3 blocking peptide on VCAM-1 upregulation in HAEC. Note that at 0.1 μM the blocking peptide has an inhibitory effect on VCAM-1 upregulation that is similar to the inhibition observed when HAEC express CD40 that cannot recruit TRAF2, 3 ($\Delta$T2, 3).
Figure 6:
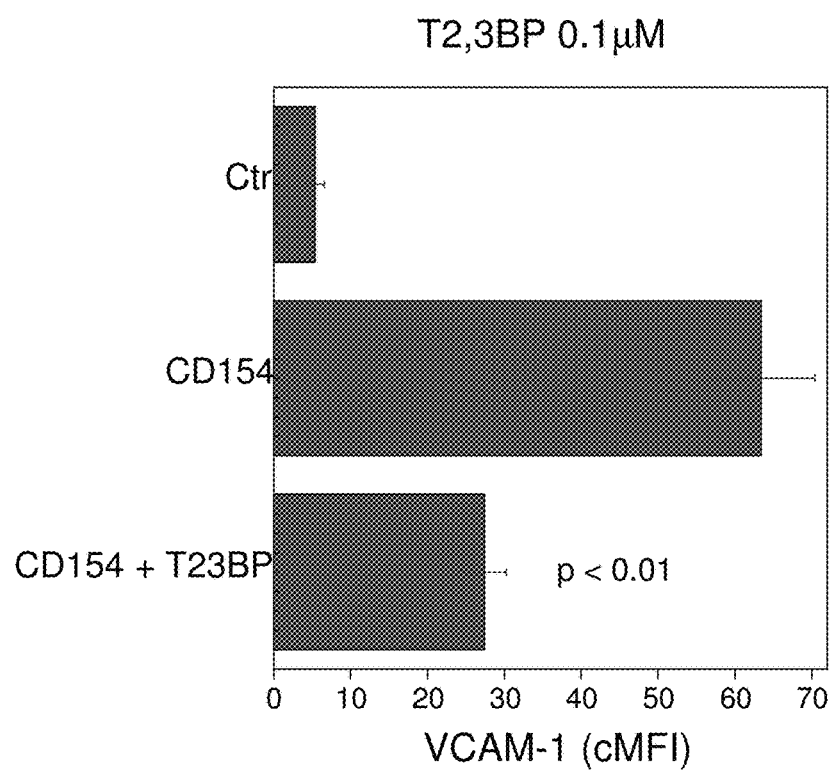
FIG. 6 is a graph showing the effects of second generation TRAF 2, 3 blocking peptide on VCAM-1 upregulation in HAEC.
Figure 7:
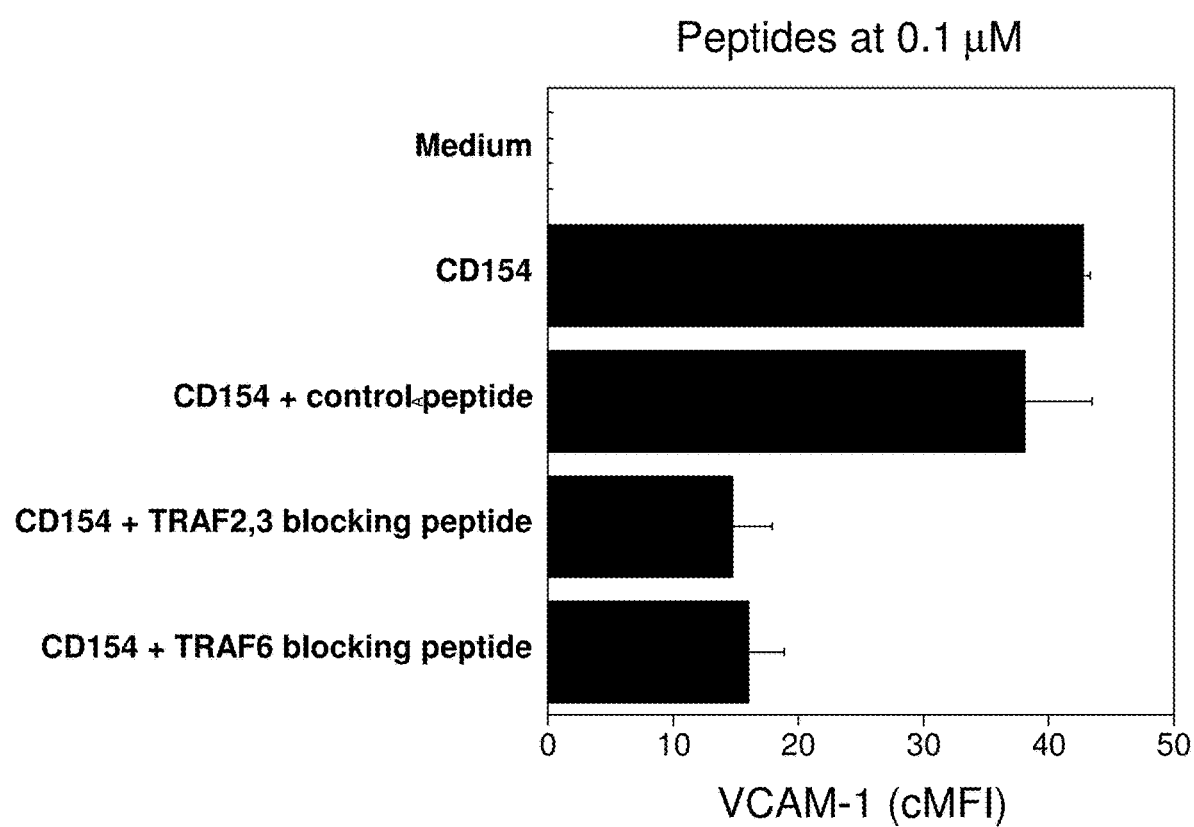
FIG. 7 is a graph showing the effects of second generation TRAF2,3 and TRAF6 blocking peptides (at 0.1 μM) on VCAM-1 upregulation in HAEC.

We used second generation blocking peptides that included a Tat MTD. Incubation of HAEC with TRAF2,3 blocking peptide (SEQ ID NO: 13) or TRAF6 blocking peptide or (SEQ ID NO: 18) caused a 60% inhibition of upregulation of VCAM-1 triggered by CD154 (p<0.02) (FIG. 5). In parallel experiments, a scrambled peptide showed no inhibitory effect. The second-generation peptides had an inhibitory effect that mimicked those of CD40 mutants that cannot recruit appropriate TRAFs indicating the efficacy of blocking peptides. Moreover, these effects were achieved at concentrations of 100 nM.

Potential Role of IL-1 in CD40-Induced Pro-Atherogenic Responses

Some atherogenic responses (e.g., tissue factor expression) remain after the function of the TRAF2,3 site has been prevented (ΔT2,3). The TRAF6 site drives these responses in cells that express ΔT2,3. This site regulates pro-inflammatory cytokine secretion (such as IL-1) in Mφ. We hypothesized that the TRAF6 binding site controls atherosclerosis through IL-1 since this cytokine activates atherogenesis. Thus, blockade of IL-1 would impair atherogenic responses that persist when the function of the TRAF2,3 site has been prevented.

Figure 8:
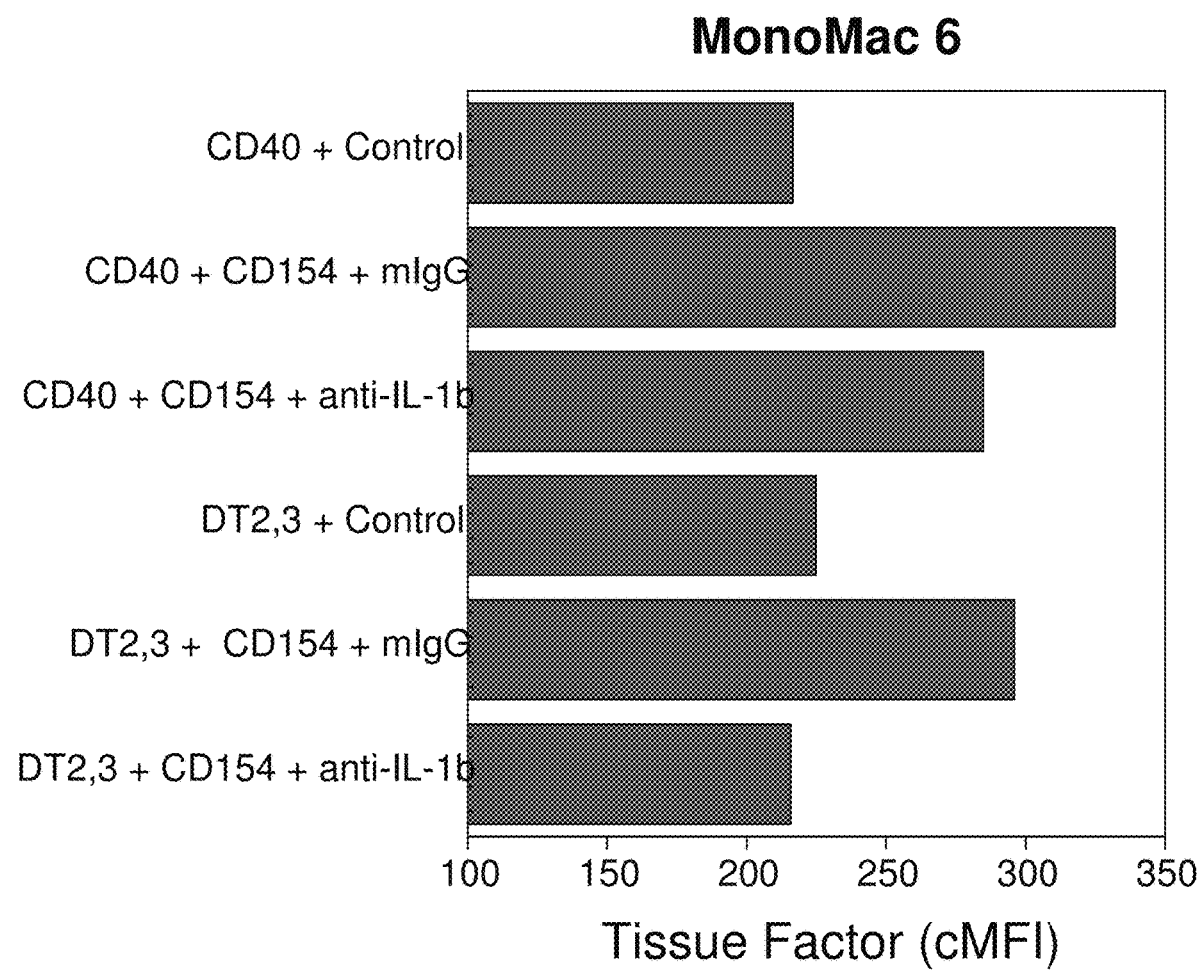
FIG. 8 is a graph showing that IL-1 and CD40 cooperate to induce tissue factor upregulation on MonoMac 6 cells.

We centered on IL-1 because of its key role in atherosclerosis, IL-1 can act downstream of other pro-inflammatory cytokines and blockade of IL-1 does not appear to impair resistance to opportunistic pathogens. MonoMac 6 cells were transduced with wt CD40 or CD40 ΔT2,3. HAEC were incubated with a neutralizing anti-IL-1β or control mAbs followed by addition of CD154. The expression of tissue factor that was still detected by cells that expressed CD40 ΔT2,3 (these cells signal through TRAF6) was inhibited by neutralization of IL-1β (FIG. 8). These results show that simultaneous blockade of CD40-TRAF plus IL-1 signaling optimally impairs pro-atherogenic responses in vitro and in vivo.

Example 3

Using a model of ischemia/reperfusion (I/R)-induced retinopathy, we examined whether CD40 is an upstream regulator of retinal inflammation and neurovascular degeneration.

Materials and Methods

Animals

Male C57BL/6 (B6), CD40−/− (B6 background), and C57BL/6-TgN(ACTbEGFP)1Osb (B6 EGFP, in which EGFP is enhanced green fluorescent protein; mice were bred at the Animal Resource Center (Case Western Reserve University, Cleveland, OH). B6 EGFP mice express EGFP under the control of chicken β-actin promoter (Okabe, M., M. Ikawa, K. Komitnami, T. Nakanishi, and Y. Nishimune. 1997. "Green mice" as a source of ubiquitous green cells. FEBS Lett. 407: 313-319). All animals were originally obtained from The Jackson Laboratory. Animals weighed 25-30 g when used for experiments.

Model of Retinal I/R

Retinal ischemia was induced as we previously described (Zheng, L., B. Gong, D. A. Hatala, and T. S. Kern. 2007. Retinal ischemia and reperfusion causes capillary degeneration: similarities to diabetes. Invest. Ophthalmol. Visual Sci. 48: 361-367). The anterior chamber of one eye was cannulated with a 30-gauge needle attached to a catheter infusing normal saline. Intraocular pressure (IOP) was measured by a handheld tonometer (TONO Pen; Medtronic Solan), and pressure in the eye was regulated to 80-90 mm Hg with a pressure infuser (Infu-surg; Ethox) and maintained for 90 min. The other eye of the same animal was set up as a control. After ischemia, the needle was withdrawn, IOP was normalized, and reflow of the retinal circulation was documented visually. Animals were euthanized 1, 2, or 8 days after I/R injury as indicated. Studies were approved by the Institutional Animal Care and Use Committee of Case Western Reserve University School of Medicine.

Bone Marrow Transplantation

This was conducted as previously described (van Parijs, L., Y. Refaeli, A. K. Abbas, and D. Baltimore. 1999. Autoimmunity as a consequence of retrovirus-mediated expression of C-FLIP in lymphocytes. Immunity 11: 763-770). Briefly, bone marrow cells were obtained from the femur and tibia of B6 EGFP or CD40−/− mice. Recipient B6 and CD40−/− mice received 12 Gy of whole-body irradiation in two doses 3 h apart followed by i.v. administration of 4×106 bone marrow cells. Mice were used for experiments at 4 wk posttransplant. The success of the transplant was assessed at 4 wk by examining the percentage of peripheral blood leukocytes that express EGFP. Administration of EGFP B6 bone marrow cells to CD40−/− (knockout; KO) mice (B6→KO) and of CD40−/− bone marrow cells to EGFP B6 mice (KO→B6) resulted in >90% EGFP+ and >90% EGFP− leukocytes in peripheral blood respectively.

Histopathology and Quantitation of Degenerate (Acellular) Capillaries

Histological changes induced by I/R were assessed as described before (Visual Sci. 48: 361-367). Formalin-fixed, paraffin-embedded sections were stained with periodic acid-Schiff and hematoxylin for light microscopy. The ganglion cell nuclei and leukocytes were counted under 400×. Retinal vasculatures were isolated as we previously described (Zheng, L., C. Szabo, and T. S. Kern. 2004. Poly(ADP-ribose) polymerase is involved in the development of diabetic retinopathy via regulation of nuclear factor κB. Diabetes 53: 2960-2967, Kern, T. S., J. Tang, M. Mizutani, R. A. Kowluru, R. H. Nagaraj, G. Romeo, F. Podesta, and M. Lorenzi. 2000. Response of capillary cell death to aminoguanidine predicts the development of retinopathy: comparison of diabetes and galactosemia. Invest. Ophthalmol. Visual Sci. 41: 3972-3978). Briefly, freshly isolated eyes were fixed with 10% neutral buffered formalin for 1 day. Retinas were isolated, washed in water overnight, and then incubated with 3% crude trypsin (Difco; BD BioSciences) at 37° C. for 1 h. Nonvascular cells were gently brushed away from the vasculature, and the isolated vasculature laid out on slides and used for acellular capillary examination. Sections were then stained with periodic acid-Schiff and hematoxylin. Acellular capillaries were identified as capillary-sized vessel tubes having no nuclei anywhere along their length and are reported per square millimeter of retinal area (Visual Sci. 48: 361-367, Diabetes 53: 2960-2967).

Immunohistochemistry

Eyes were fixed overnight in 4% paraformaldehyde in phosphate buffer and embedded in paraffin. Sections were deparaffinized and subjected to Ag retrieval by heating in citrate buffer with a microwave for 15 min. Sections were permeabilized with 0.1% Triton X-100. After blocking for 1 h with PBS containing 5% normal goat serum, sections were incubated overnight at 4° C. with anti-NOS2 or anti-COX-2 Ab (Millipore and Cayman Chemical Co., respectively) followed by incubation with secondary Ab conjugated to biotin (Jackson ImmunoResearch Laboratories) for 1 h at room temperature. Sections were resolved using a Vectastain ABC kit (Vector Laboratories) followed by diaminobenzidine substrate and counterstaining with hematoxylin. Specificity of staining was determined by incubating sections with control primary Ab plus secondary Ab or with secondary Ab alone.

Real-Time Quantitative RT-PCR

Total cellular RNA from retinas was isolated using the RNeasy kit (Qiagen). After treatment with DNase (Ambion), 0.5 μg of RNA was used to generate cDNA using oligo (dT)$_{12-18}$ primers and Superscript III reverse transcriptase (Invitrogen Life Technologies) as we described (Subauste, C. S., A. Subauste, and M. Wessendarp. 2007. Role of CD40-dependent down-regulation of CD154 in impaired induction of CD154 in CD4+ T cells from HIV-1-infected patients. J. Immunol. 178: 1645-1653). cDNA (2.5 µl) was used as template for RT-PCR using SYBR Green PCR Master Mix (Applied Biosystems) and 20 pM (each) primers in a final volume of 50 µl. Primer sequences for NOS2 (Park, E.-M., S. Cho, K. Frys, G. Racchumi, P. Zhou, J. Anrather, and C. Iadecola. 2004. Interaction between inducible nitric oxide synthase and polyADP-ribose polymerase in focal ischemic brain injury. Stroke 35: 2896-2901), COX-2 (Wei, X., X. Zhang, M. J. Zuscik, M. H. Drissi, E. M. Schwarz, and R. J. O'Keefe. 2005. Fibroblasts express RANKL and support osteoclastogenesis in a COX-2-dependent manner after stimulation with titanium particles. J. Bone Min. Res. 20: 1136-1148), ICAM-1 (Stroke 35: 2896-2901), keratinocyte-derived chemokine (KC)/CXCL1 (Zhou, J. T., L. Pham, N. Zhang, S. He, M.-A. Gamulescu, C. Spee, J. Ryan, and D. R. Hinton. 2005. Neutrophils promote experimental choroidal neovascularization. Mol. Vision 11: 414-424), MCP-1 (Zaheer, A., S. K. Sahu, Y. Wu, A. Zaheer, J. Haas, K. Lee, and B. Yang. 2007. Diminished cytokine and chemokine expression in the central nervous system of GMF-deficient mice with experimental autoimmune encephalomyelitis. Brain Res. 1144: 239-247), and 18S rRNA (J. Immunol. 178: 1645-1653) were previously described. Expression of these genes was assessed using a 7300 Real Time PCR System (Applied Biosystems). Each cDNA sample was run in duplicate. Samples were normalized according to the content of 18S rRNA (J. Immunol. 178: 1645-1653).

Isolation of Primary Retinal Cells

Mice were anesthetized and eyes were enucleated. Retinas were isolated and digested in a solution containing papain, 15 IU/ml, and DNase, 15 µg/ml (Worthington Biochemicals) for 30 min at 37° C. Tissue was dissociated by gentle pipetting and passed through a 40-µm pore size cell strainer. Flow through was mixed with FBS and washed. Tissue trapped by the strainer was digested with collagenase type I (1 mg/ml; Worthington Biochemicals) for 30 min at 37° C. to free endothelial cells. After dissociation, mixing with FBS and washing, cells obtained after papain-DNase and collagenase treatment were pooled and counted. Viability of the cells was consistently >90% as assessed by trypan blue exclusion.

Retinal Cell Lines and CD40 Stimulation

A line of mouse retinal endothelial cells and a line of mouse retinal glial cells with Muller cell characteristics (Su, X., C. M. Sorenson, and N. Sheibani. 2003. Isolation and characterization of murine retinal endothelial cells. Mol. Vision. 9: 171-178, Scheef, E., S. Wang, C. M. Sorenson, and N. Sheibani. 2005. Isolation and characterization of murine retinal astrocytes. Mol. Vision 11: 613-624) were gifts from Dr. N. Sheibani (University of Wisconsin, Madison, WI). Cells were maintained as described at 33° C. in DMEM containing 20% FBS (HyClone), 2 mM L-glutamine, 2 mM sodium pyruvate, 20 mM HEPES, 1% nonessential amino acids, 100 µg/ml streptomycin, 100 U/ml penicillin, endothelial growth supplement (100 µg/ml; Sigma-Aldrich), and IFN-γ (44 U/ml; PeproTech). Cells were treated with or without mouse CD154 (¼ dilution of cell-free supernatants, a gift from Dr. R. Kornbluth, University of California San Diego; Ref. 36) or IL-1β (25 pg/ml; PeproTech) for 24 h at 37° C. Cells were used for flow cytometry, and cell supernatants were collected for ELISA.

Flow Cytometry

Suspensions of primary retinal cells were incubated with Fc block (BD Biosciences) followed by staining with anti-CD40 PE (BD Biosciences) and biotinylated anti-CD105 mAb followed by streptavidin-allophycocyanin (eBioscience) or appropriate isotype control mAbs. For detection of intracellular markers, cells were then fixed and permeabilized by using IntraPrep permeabilization reagent (Beckman Coulter) following the manufacturer's instructions (Subauste, C. S., M. Wessendarp, J.-A. C. Portillo, R. M. Andrade, L. M. Hinds, F. J. Gomez, A. G. Smulian, P. A. Grubbs, and L. A. Haglund. 2004. Pathogenspecific induction of CD154 is impaired in CD4+ T cells from HIV-infected individuals. J. Infect. Dis. 189: 61-70). Thereafter, cells were stained with antivimentin-FITC (Santa Cruz Biotechnologies), anti-rhodopsin mAb (ID4, a gift from Dr. K. Palczeweski, Case Western Reserve University) followed by allophycocyanin-conjugated secondary Ab (eBioscience) or appropriate isotype control Abs. After fixation with 1% paraformaldehyde, cells were analyzed using a LSR II (BD Biosciences). Expression of CD40 (corrected mean fluorescence intensity; cMFI) was analyzed on gated CD105+, vimentin+ cells, or rhodopsin+ cells. Retinal cell lines were stained with anti-CD40 allophycocyanin, anti-ICAM-1 PE or isotype control mAbs (eBiosciences).

ELISA

Supernatants from retinal cell lines cultured in 96-well plates were collected 24 h after addition of either mouse CD154 or IL-1β. Cell-free supernatants were used to measure concentrations of KC/CXCL1 (R&D Systems). The lower limit of detection of the ELISA was 2 pg/ml.

Statistical Analysis

All results were expressed as the mean±SEM. Data were analyzed by a two-tailed Student t test, ANOVA, and the nonparametric Kruskal-Wallis test followed by the Mann-Whitney U test. Differences were considered statistically significant at $p<0.05$.

Results

Figure 9A:
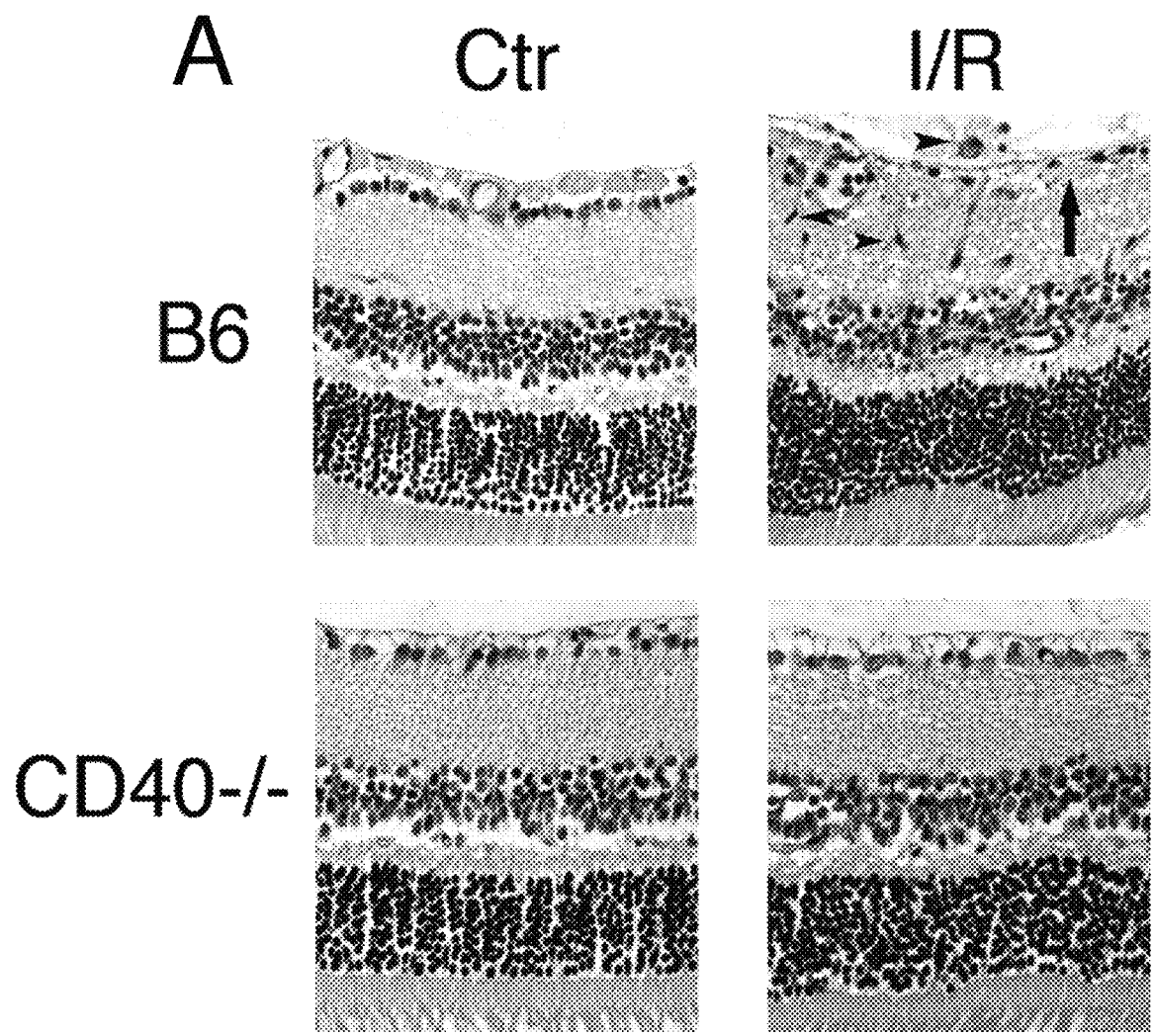
FIGS. 9A-C illustrate images showing CD40 promotes leukocyte infiltration, ganglion cell loss, and capillary degeneration after retinal ischemia/reperfusion (I/R). One eye from each B6 and CD40$^{-/-}$ mouse was subjected to I/R. Nonischemic eyes were used as controls (Ctr). Eyes were obtained 2 days (A and B) and 8 days (C) after I/R. A, Leukocytes in the retina and vitreous were noted in ischemic eyes from B6 mice (arrowheads) but not from CD40$^{-/-}$ mice. A marked decrease in the number of ganglion cells is observed in ischemic eyes from B6 (arrow) but not from CD40$^{-/-}$ mice. Original magnification, ×400.
Figure 11:
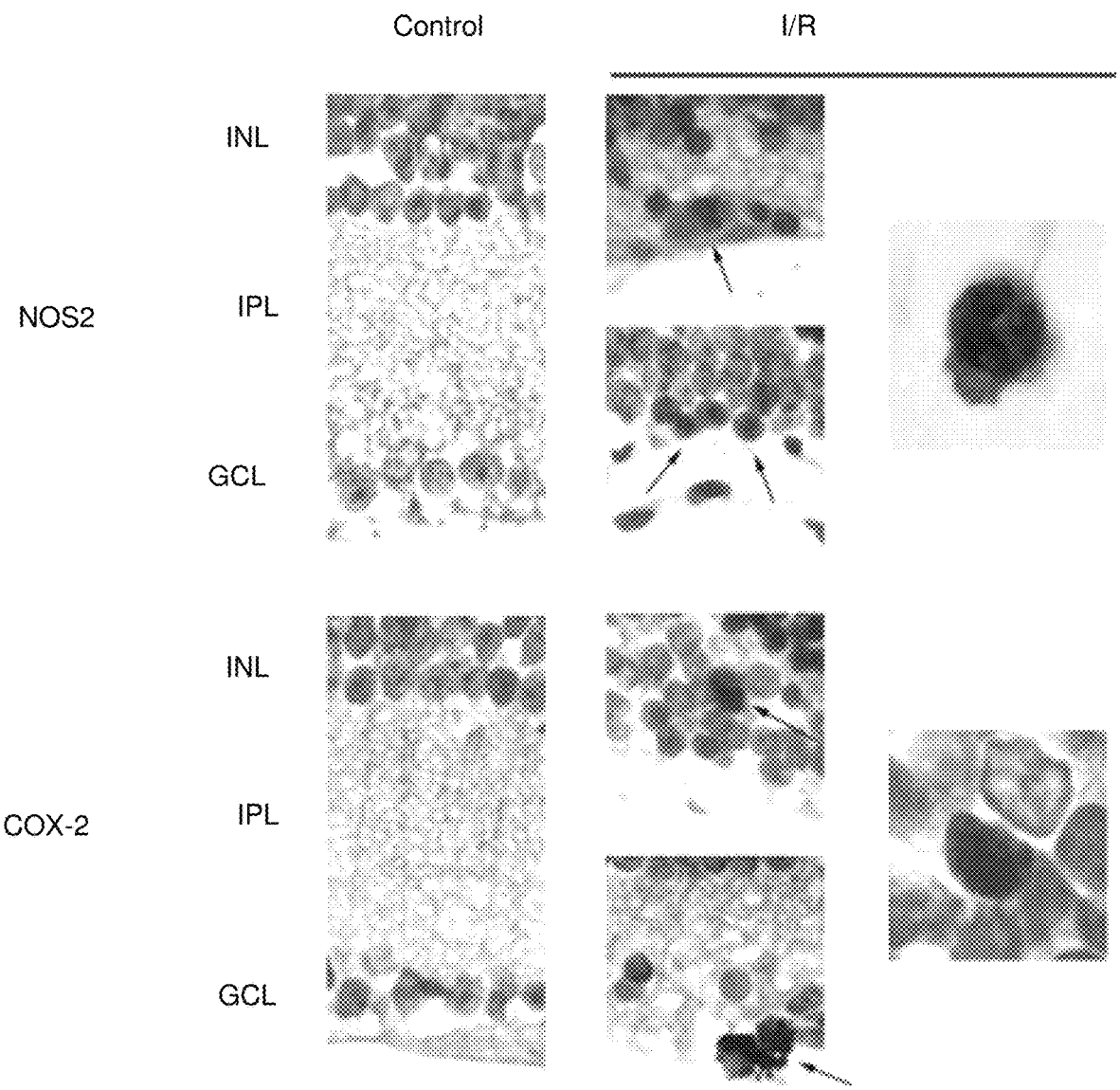
FIG. 11 illustrates images showing leukocytes that infiltrate ischemic retinas and vitreous express NOS2 and COX-2. Nonischemic eyes from B6 mice (Control) as well as eyes collected 2 days after I/R were sectioned and subjected to immunohistochemistry for NOS2 or COX-2. Arrows denote leukocytes that express these proteins. GCL, ganglion cell layer; IPL, inner plexiform layer; INL, inner nuclear layer. Note marked reduction of ganglion cells and thinning of inner plexiform layer in ischemic retinas. Original magnification, ×400. Images to the far right reveal a leukocyte in the vitreous that expresses NOS2 and another in the inner nuclear layer that expresses COX-2. Original magnification, ±1000.

CD40 is an Important Mediator of Inflammation and Neurovascular Degeneration After Retinal I/R We used a well-established model of I/R-induced retinal injury (transient elevation of IOP) to examine the in vivo relevance of CD40. The histological features of the retina from untreated B6 and $CD40^{-/-}$ mice were similar (FIG. 1A). Histological examination 2 days after I/R revealed the presence of leukocytes infiltrating in the inner layers of retinas and vitreous from B6 mice (FIG. 9A; see also FIG. 11). In marked contrast, no infiltrating leukocytes were detected in retinas from $CD40^{-/-}$ mice.

Figure 9B:
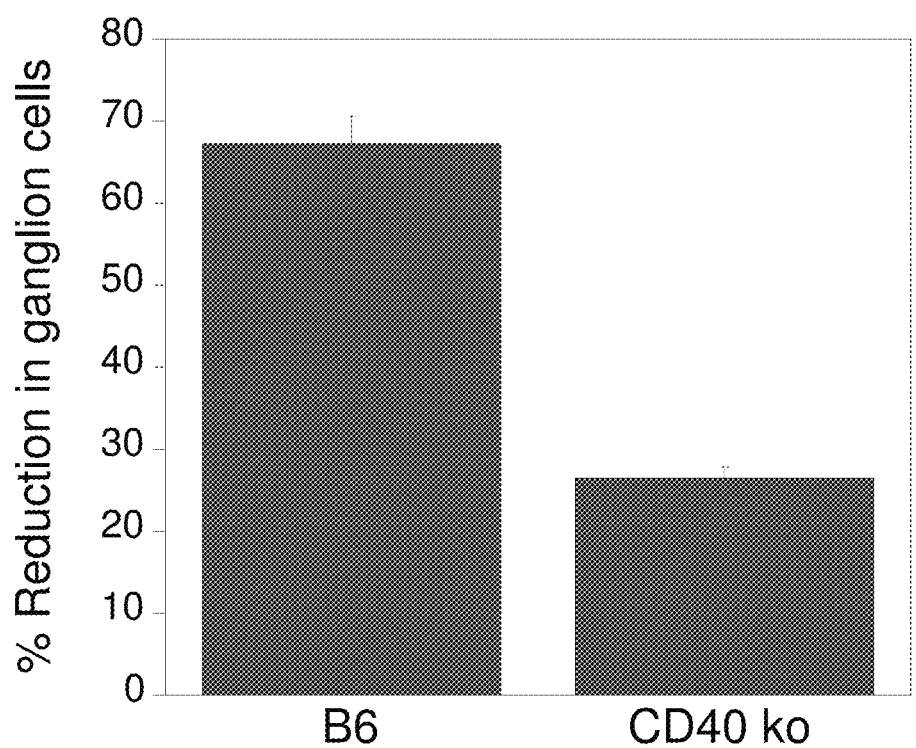
Figure 9C:
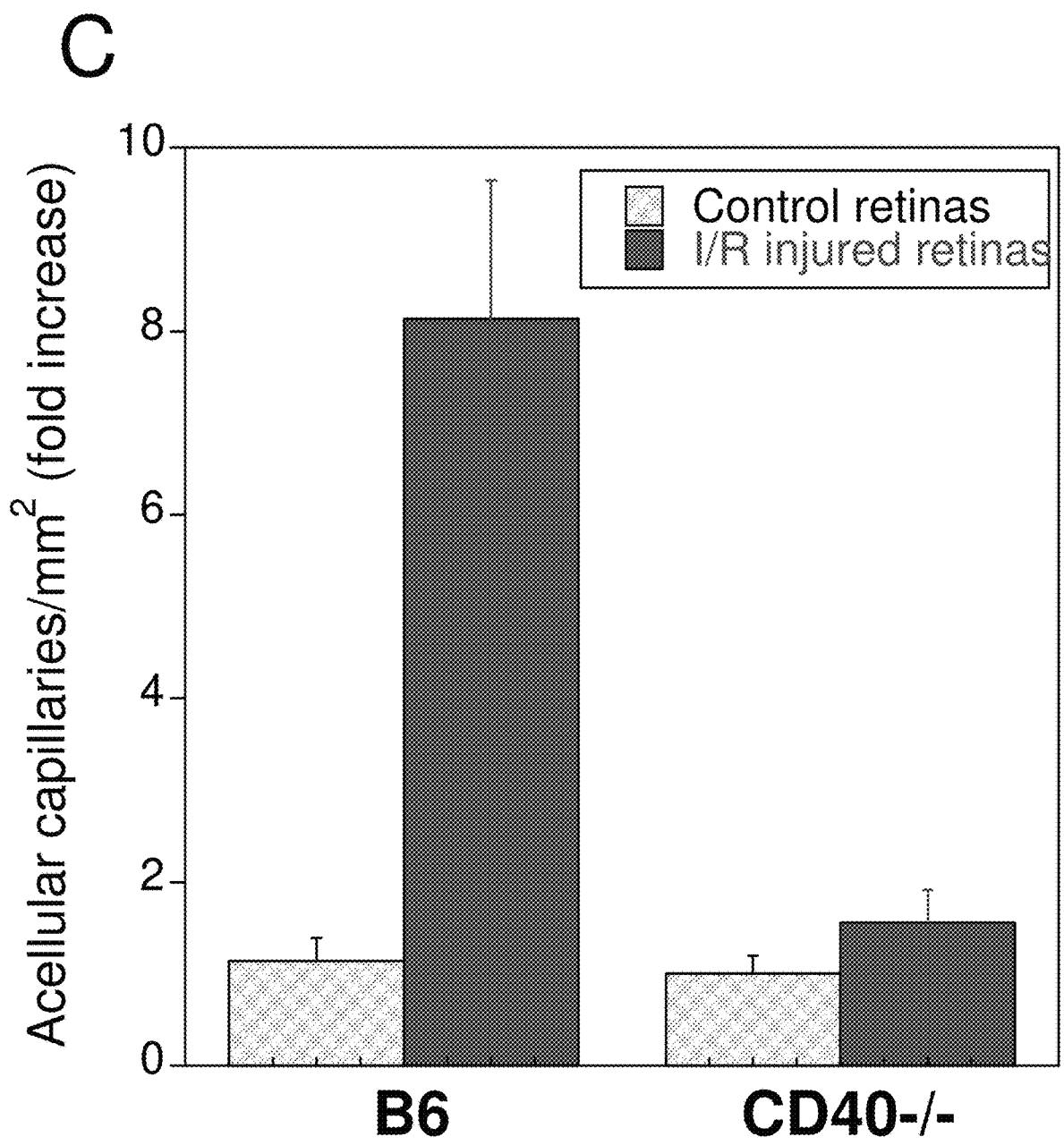

In addition to the presence of leukocytes, retinas from B6 mice collected 2 days after I/R revealed a marked decrease in the number of ganglion cells (average of 63% decrease; n=3; p=0.01; FIGS. 9, A and B). In contrast, retinas from $CD40^{-/-}$ mice subjected to I/R revealed a modest and statistically nonsignificant decrease in the number of ganglion cells (average of 26% decrease; n=3, p>0.05; FIGS. 9, A and B).

Capillary degeneration is an important feature of ischemic retinopathies including those caused by I/R and diabetes. Indeed, retinas from B6 mice revealed a marked increase in the number of degenerate (acellular) capillaries at 8 days post-I/R (n=5; p<0.001; FIG. 1C). $CD40^{-/-}$ mice were protected from the capillary degeneration induced by I/R given that there was only a modest increase in the number of acellular capillaries that was statistically nonsignificant (n=4; p>0.05). Taken together, these results indicate that CD40 is an important mediator of retinal inflammation and promotes neurovascular degeneration.

CD40 Controls NOS2 and COX-2 Expression in the Ischemic Retina

Figure 10:
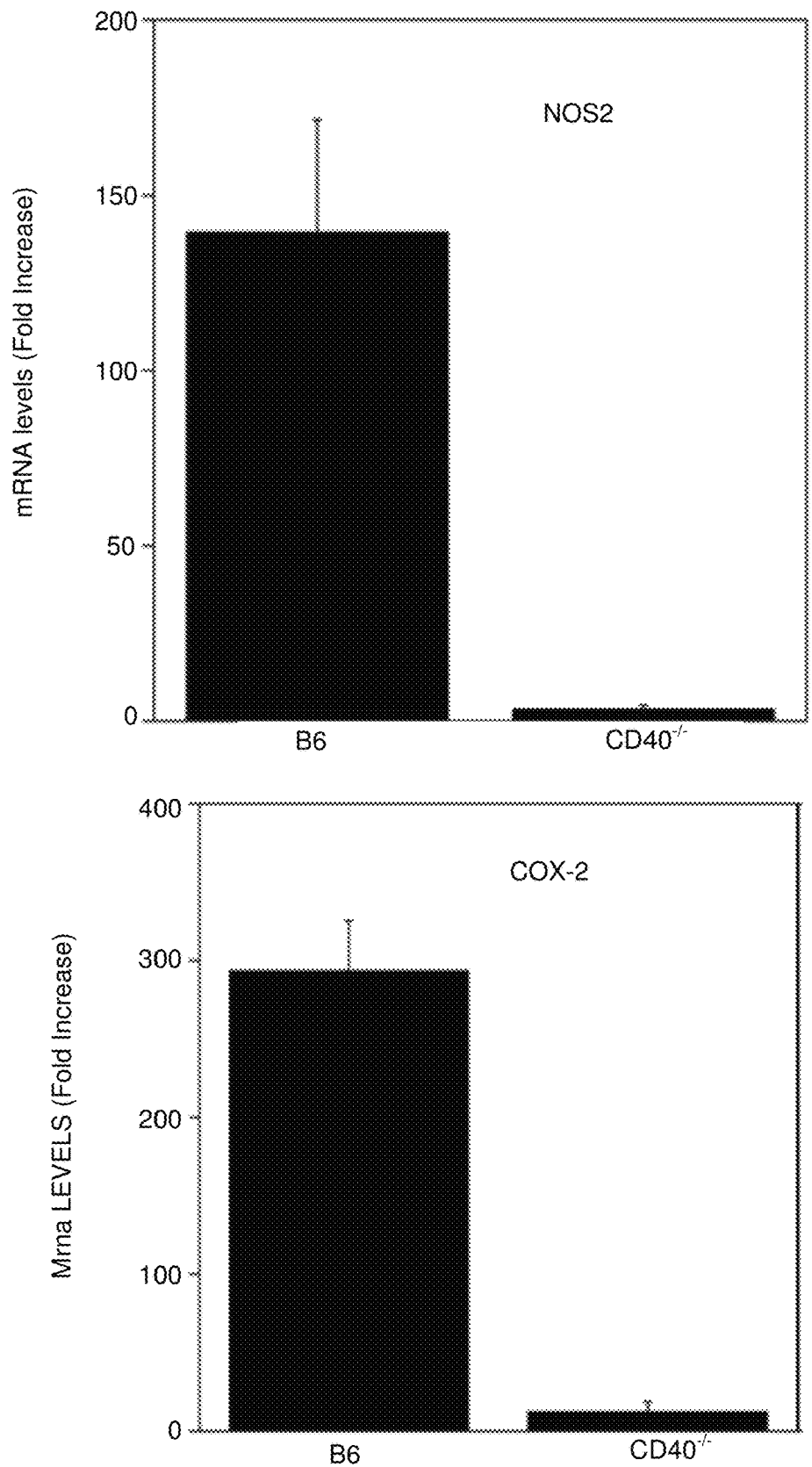
FIG. 10 illustrates graphs showing CD40 promotes up-regulation of NOS2 and COX-2 mRNA in ischemic retinas. One eye of each B6 and CD40$^{-/-}$ mouse was subjected to ischemia. After 24 h, RNA was isolated from ischemic and nonischemic retinas. cDNA was subjected to quantitative real time PCR. NOS2 and COX-2 mRNA levels were normalized against 18S rRNA. Data are expressed as fold increase of NOS2 and COX-2 in the ischemic vs the non ischemic retina values represent means±SEM (three to five mice per group).

We conducted experiments to identify mechanisms by which CD40 mediates retinal injury. NOS2 plays an important role in neurovascular degeneration in retinopathies including those mediated by acute ischemia and diabetes (Visual Sci. 48: 361-367, Hangai, M., N. Yoshimura, K. Hiroi, M. Mandai, and Y. Honda. 1996. Inducible nitric oxide synthase in retinal ischemia-reperfusion injury. Exp. Eye Res. 63: 501-509, Zheng, L., Y. Du, C. Miller, R. A. Gubitosi-Klug, T. S. Kern, S. Ball, and B. A. Berkowitz. 2007. Critical role of inducible nitric oxide synthase in degeneration of retinal capillaries in mice with streptozotocin-induced diabetes. Diabetologia 50: 1987-1996, Sennlaub, F., Y. Courtois, and O. Goureau. 2002. Inducible nitric oxide synthase mediates retinal apoptosis in ischemic proliferative retinopathy. J. Neurosci. 22: 3987-3993, Neufeld, A. H., S. Kawai, S. Das, S. Vora, E. Gachie, J. R. Connor, and P. T. Manning. 2002. Loss of retinal ganglion cells following retinal ischemia: the role of inducible nitric oxide synthase. Exp. Eye Res. 75: 521-528). In addition, COX-2 promotes neuronal injury after ischemia (Iadecola, C., K. Niwa, S. Zhao, M. Nagayama, E. Araki, S. Morham, and E. Ross. 2001. Reduced susceptibility to ischemic brain injury and N-methyl-D-aspartate-mediated neurotoxicity in cyclooxygenase-2-deficient mice. Proc. Natl. Acad. Sci. USA 98: 1294-1299). Thus, we examined whether CD40 controls the expression of NOS2 and COX-2 after I/R of the retina. I/R causes a marked up-regulation of NOS2 and COX-2 mRNA in the retinas of B6 mice (FIG. 10). In contrast, CD40$^{-/-}$ mice were protected from I/R-induced NOS2/COX-2 up-regulation (n=3; p<0.02). These results indicate that CD40 controls in vivo cellular responses linked to neural degeneration and inflammation.

Immunohistochemistry was performed to identify cells that express NOS2 and COX-2 in the early stages of retinal ischemia. While NOS2 was not detected in normal mouse retina, some cells in the ganglion cell layer and inner nuclear layer were weakly positive for COX-2 (FIG. 11) (Ju, W.-K., and A. H. Neufeld. 2002. Cellular localization of cyclooxygenase-1 and cyclooxygenase-2 in the normal mouse, rat, and human retina. J. Compar. Neurol. 452: 392-399). Infiltrating leukocytes that were intensely positive for NOS2 and COX-2 were detected in the vitreous and retinas from B6 mice subjected to I/R (FIG. 11). Thus, CD40 regulates the expression of NOS2 and COX-2 in part by promoting recruitment of leukocytes that express these molecules.

CD40 Mediates Up-Regulation of KC/CXCL1 and ICAM-1 in the Ischemic Retina

Figure 12:
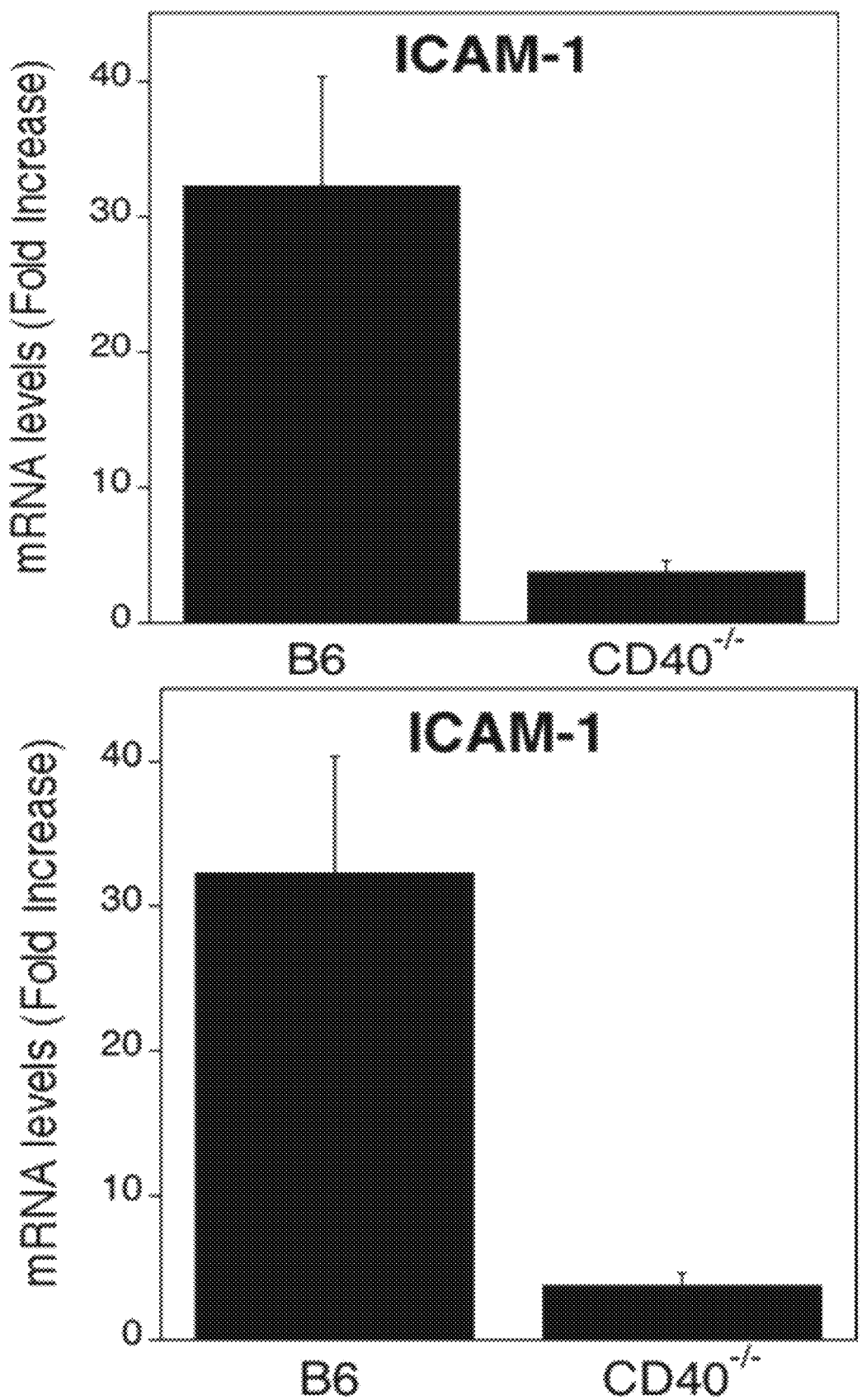
FIG. 12 illustrates graphs showing CD40 promotes up-regulation of KC/CXCL1 and ICAM-1 mRNA in ischemic retinas. One eye of each B6 and CD40$^{-/-}$ mouse was subjected to ischemia. After 24 h, RNA was isolated from ischemic and nonischemic retinas. cDNA was subjected to quantitative real time PCR. KC/CXCL1 and ICAM-1 mRNA levels were normalized against 18S rRNA. Data are expressed as fold increase of KC/CXCL1 and ICAM-1 in the ischemic v the nonischemic retina. Values represent means±SEM (three to five mice per group).

The retina is infiltrated by polymorphonuclear leukocytes in the early stages after ischemia (Neufeld, A. H., S. Kawai, S. Das, S. Vora, E. Gachie, J. R. Connor, and P. T. Manning. 2002. Loss of retinal ganglion cells following retinal ischemia: the role of inducible nitric oxide synthase. Exp. Eye Res. 75: 521-528). We hypothesized that CD40 mediates up-regulation of KC/CXCL1 in ischemic retinas because KC/CXCL1 can be produced by nonhemopoietic cells and mediates recruitment of polymorphonuclear leukocytes (Armstrong, D. A., J. A. Major, A. Chudyk, and T. A. Hamilton. 2004. Neutrophil chemoattractant genes KC and MIP-2 are expressed in different cell populations at sites of surgical injury. J. Leukocyte Biol. 75: 641-648). Using real-time PCR, we detected a marked up-regulation of KC/CXCL1 mRNA levels in retinas from B6 mice subjected to I/R (FIG. 12). Such up-regulation was abrogated in ischemic retinas from CD40$^{-/-}$ mice (n=4; p=0.01).

Next, we examined whether CD40 promotes up-regulation of the adhesion molecule ICAM-1 after I/R. ICAM-1 mRNA levels were increased in retinas from B6 mice subjected to I/R (FIG. 12). Such up-regulation was significantly inhibited in ischemic retinas from CD40$^{-/-}$ mice (n=4; p=0.03). Thus, CD40 regulates retinal expression of KC/CXCL1 and ICAM-1, events known to mediate leukocyte recruitment.

CD40 Induces ICAM-1 Up-Regulation as Well as KC/CXCL1 Production by Retinal Cells Endothelial and Muller cells are major components of the blood-retinal barrier (Tout, S., T. Chan-Ling, H. Hollander, and J. Stone. 1993. The role of Muller cells in the formation of the blood-retinal barrier. Neuroscience 55: 291-301). Thus, we reasoned that these cells might be involved in CD40-dependent expression of KC/CXCL1 and ICAM-1. To begin to test this hypothesis we determined whether these cells express CD40. Suspensions of primary mouse retinal cells were stained with Abs against CD105, vimentin (markers for endothelial and Muller cells, respectively), CD40, or control Abs. Flow cytometry analysis of gated CD105$^+$ and vimentin$^+$ cells revealed expression of CD40. In contrast, photoreceptors (the major subset of retinal cells) identified by intracellular staining with an anti-rhodopsin mAb, did not express CD40. We also used flow cytometry to examine whether the phenotypic composition of retinal cells as it relates to endothelial and Muller cells were different in B6 compared with CD40$^{-/-}$ mice. The percentages of retinal cells that were CD105$^+$ and vimentin+ were 0.9 and 36%, respectively, in B6 mice (n=4). Similar percentages were observed in CD40$^{-/-}$ mice (0.8 and 35%; n=2). Thus, it appears unlikely that the different responses to retinal ischemia observed in B6 compared with CD40$^{-/-}$ mice were explained by changes in retinal endothelial/Muller cell development in CD40$^{-/-}$ animals.

Figure 13:
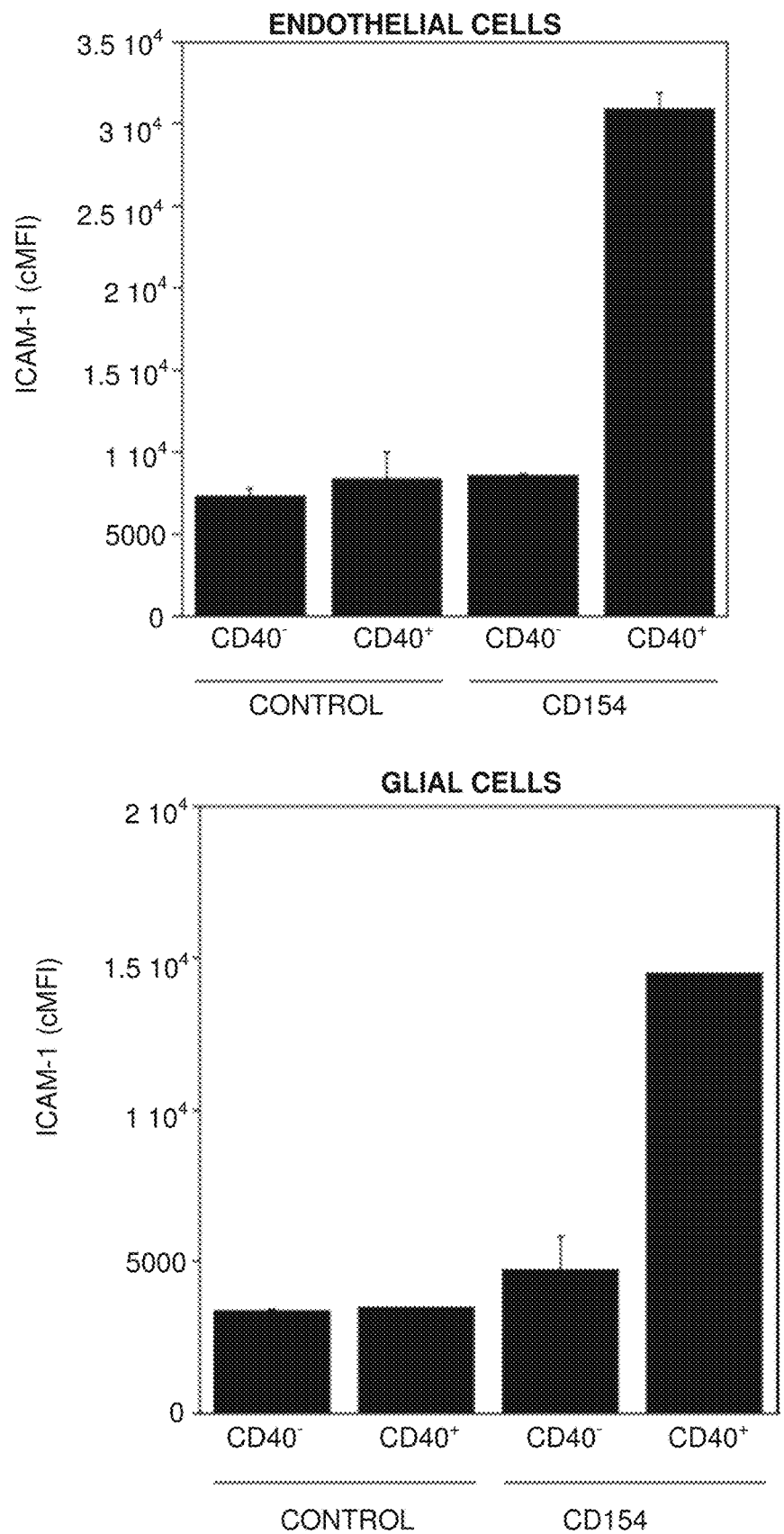
FIG. 13 illustrates graphs showing CD40 up-regulates ICAM-1 on retinal endothelial and glial cells. Lines of mouse retinal endothelial cells and retinal glia with Muller cell characteristics were incubated with or without mouse CD154 for 24 h. Cells were stained with mAbs against CD40 and ICAM-1. Expression of ICAM-1 (cMFI) on gated CD40$^-$ and CD40$^+$ cells are shown.
Figure 14:
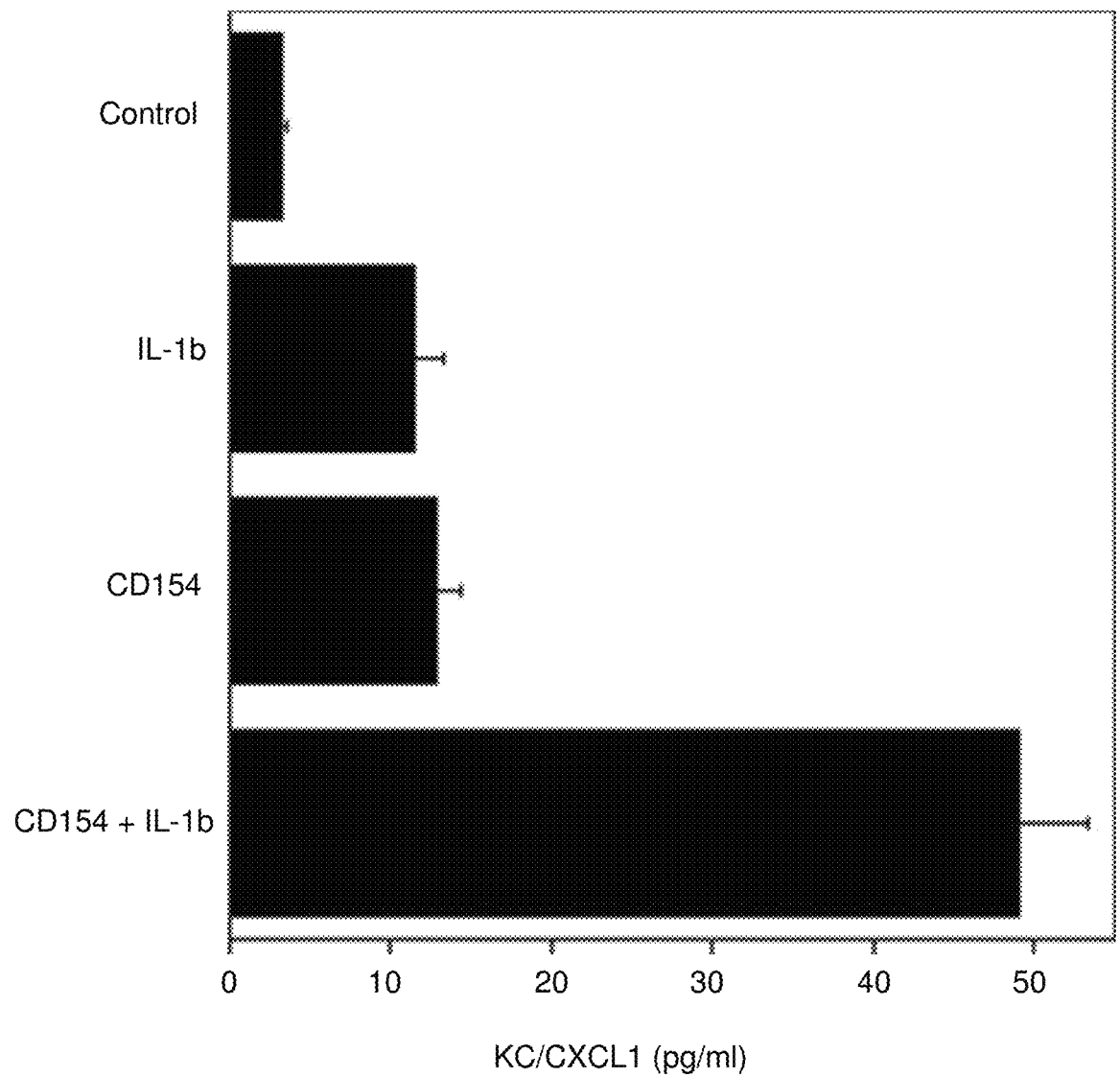
FIG. 14 illustrates a graph showing CD40 and IL-1β cooperate to trigger KC/CXCL1 production by retinal endothelial cells. A mouse retinal endothelial cell line was incubated with or without mouse CD154 or IL-1β (25 pg/ml). Supernatants were collected at 24 h and used to measure concentration of KC/CXCL1 by ELISA.

We used lines of mouse retinal endothelial cells and retinal glia with Muller cell characteristics to determine whether CD40 stimulation up-regulates ICAM-1. Incubation of these cells with mouse CD154 significantly increased expression of ICAM-1 on CD40$^+$ cells (FIG. 13; p<0.001). Next, we examined the effects of CD40 stimulation on KC/CXCL1 secretion. IL-1 is an important proinflammatory cytokine induced after ischemia that regulates chemokine production and mediates tissue injury (Yoneda, S., H. Tanihara, N. Kido, Y. Honda, W. Goto, H. Hara, and N. Miyawaki. 2001. Interleukin-1β mediates ischemic injury in the rat retina. Exp. Eye Res. 73: 661-667, Strieter, R. M., S. L. Kunkel, H. J. Showell, D. G. Remick, S. H. Phan, P. A. Ward, and R. M. Marks. 1989. Endothelial cell gene expression of a neutrophil chemotactic factor by TNF-α, LPS, and IL-1β. Science 243: 1467-1469). We explored whether CD40 and IL-1 cooperate to induce KC/CXCL1 production. Low concentrations of IL-1β (25 pg/ml) were used for these experiments. Compared with retinal endothelial cells incubated with CD154 or IL-1β alone, coincubation with CD154 plus IL-1β resulted in an increase in secretion of KC/CXCL (FIG. 14; p<0.01). Taken together, CD40 promotes retinal endothelial and Muller cell expression of molecules key for leukocyte recruitment.

Expression of CD40 in the Retina is Required for Development of Ischemic Retinopathy We conducted experiments to determine whether development of ischemic retinopathy required tissue expression of CD40. Bone marrow chimeras were generated using CD40$^{+/+}$ (B6) and CD40$^{-/-}$ mice. B6→B6 and CD40$^{-/-}$→CD40$^{-/-}$ transplants were generated as controls, and they behaved like nontransplanted B6 and CD40$^{-/-}$ animals, respectively. One eye per mouse was subjected to I/R at 4 wk posttransplant. As shown in FIG. 15, KO→B6 and B6→B6 mice exhibited leukocytic infiltrates and prominent loss of ganglion cells after retinal ischemia. In contrast, these findings were ameliorated in CD40→KO and KO→KO mice (p<0.05). In addition, although ICAM-1 and KC/CXCL1 mRNA were markedly up-regulated in KO→B6 mice, expression of these genes was blunted in B6→KO mice. Taken together, these studies indicate that whereas the origin of leukocytes (CD40$^{+/+}$ or CD40$^{-/-}$ animals) has little effect on the development of retinopathy, tissue expression of CD40 in the retina is pivotal for development of ischemic retinopathy.

Example 4

Cell-penetrating peptides are an effective way to impair protein-protein interactions. We showed that a cell permeable peptide that consists of the amino acid sequence of the TRAF2,3 site fused with HIV TAT$_{47-57}$ to make it cell permeable effectively blocks CD40-TRAF2,3 interactions and markedly inhibits inflammatory responses in vitro. The peptide impairs the CD40-TRAF2,3 pathway both in human and mouse cells since the amino acid sequence of the TRAF2,3 binding site is the same in both species. Retro inverso (ri) peptides made following reverse amino acid sequence and synthesized with D-amino acids can have identical function to those made with L-amino acids, but have the advantage of being resistant to peptidases. We examined the effects of a cell-penetrating ri CD40-TRAF2,3 blocking peptide in the development of inflammation and retinopathy after retinal ischemia. This model was chosen since: i) Ischemia plays a central role in tissue injury in various retinopathies including those caused by central retinal artery occlusion, retinal vein occlusion and diabetes. ii) These disorders remain a common cause of visual disability despite current therapeutic approaches. iii) Inflammation plays an important role in the development of retinopathy after retinal I/R and diabetes, and CD40 is a key driver of retinal inflammation and development of these retinopathies. We show that a ri CD40-TRAF2,3 blocking peptide markedly impairs inflammation and ganglion cell loss after retinal I/R, and this effect is similar to that observed in mice that lack CD40. Moreover, the peptide is effective even if administered after retinal ischemia. This example provides evidence that pharmacologic inhibition of the CD40-TRAF2,3 pathway effectively controls a CD40-driven inflammatory disorder.

Materials and Methods

Animals

Male C57BL/6 (B6) and CD40$^{-/-}$ mice (B6 background) were purchased from Jackson Laboratories (Bar Harbor, ME) and bred at Case Western Reserve University. Animals had a weight of 25 to 30 g when used for experiments. Studies were approved by the Institutional Animal Care and Use Committee of Case Western Reserve University School of Medicine.

Model of Retinal I/R

Retinal ischemia was induced as described (10, 37). The anterior chamber of one eye was cannulated with a 30-gauge needle. Intra-ocular pressure (IOP) was maintained at 80 to 90 mm Hg for 90 minutes. The other eye of the same animal was set up as a control. After ischemia, the needle was withdrawn, IOP was normalized, and reflow of the retinal circulation was documented visually. Animals were euthanized 2 days after I/R.

Cell-Penetrating Peptides

Peptide consisted of the TRAF2,3 binding site of CD40 that was made cell permeable by linking them to the TAT$_{47-57}$ cell penetrating peptide. Peptides were synthesized using D-amino acids following reverse amino acid sequence (ri format). The sequences for the CD40-TRAF2,3 blocking peptide was —NH$_2$-rrrqrrkkrgy ghlteqvhaatn-OH (SEQ ID NO: 49). The TAT$_{47-57}$ sequence is underlined. The peptide contains a proline (p) to histidine (h) substitution (shown in italics) that enhances affinity to TRAF2. Control (scrambled) peptide consisted of NH$_2$-rrrqrrkkrgy ntqalahtgevh-OH (SEQ ID NO: 50). The blocking peptide was also synthesized with Alexa Fluor 488 conjugated via maleimide coupling to an additional Cys in the N terminus. Peptides were manufactured by Biopeptide Co. (San Diego, CA) and were low in endotoxin and >98% pure by HPLC. Peptides were used at 1 μM in vitro experiments and 1 μg for in vivo studies unless otherwise stated. Peptides were not toxic to human Müller and retinal endothelial cells as assessed by alamarBlue cell viability assay (Invitrogen Corporation).

Histopathology

Histological changes induced by I/R were assessed as described before. Formalin-fixed, paraffin embedded sections were stained with H&E for light microscopy. The ganglion cell nuclei and infiltrating neutrophils were counted under 400×.

Immunohistochemistry

Sections were incubated with antibodies against ICAM-1 (eBiosciences, San Diego, CA), KC/CXCL1 (Novus, Littleton, CO) or NOS2 (EMD Millipore, Burlington, MA) followed by incubation with fluorescent secondary antibodies (Jackson ImmunoResearch Laboratories, Inc., West Grove, PA). Sections were also incubated with anti-vimentin antibody (Novus) or Tomato lectin (Vector Laboratories, Burlingame, CA). Retinas were analyzed using a Leica DMI 6000B epifluorescence microscope.

Real Time Quantitative RT-PCR

RNA was isolated from retinas using the RNeasy kit (Qiagen). After treatment with DNase (Ambion, Austin, TX), 0.5 μg of RNA was used to generate cDNA using oligo(dT)$_{12-18}$ primers and Superscript III reverse transcriptase (Invitrogen Life Technologies, Carlsbad, CA). cDNA was used as template for RT-PCR using SYBR GREEN PCR Master Mix (Applied Biosystems, Foster City, CA) and primers. Primer sequences for ICAM-1, KC/CXCL1, NOS2, COX-2 and 18S rRNA were previously described. Expression of these genes was assessed using a 7300 Real Time PCR System (Applied Biosystems). Each cDNA sample was run in triplicate. Samples were normalized according to the content of 18S rRNA.

Retinal Cells and CD40 Stimulation

Primary human retinal endothelial cells were obtained as described (9) and cultured in complete medium supplemented with endothelial cell growth supplement from bovine pituitary (15 μg/ml; Sigma Chemical, St Louis, MO) and insulin/transferrin/selenium (Sigma Chemical). Cell identity was confirmed by incorporation of acetylated low-density lipoprotein (>90%). Endothelial cells were used between passages 3 to 6. The human Müller cell line MIO M1 (gift from Dr. Gloria Limb; University College London, UK; >95% vimentin$^+$, CRALBP$^+$ and GFAP$^-$) was also used. Endothelial cells were incubated with multimeric human CD154 to induce CD40 stimulation (obtained from Dr. Richard Kornbluth, Multimeric Biotherapeutics Inc., La Jolla, CA) or with a non-functional CD154 mutant (T147N) as control.

Luciferase Assay

Peptides were tested as described using the mouse endothelial cells mHEVc that expresses a chimera of the extracellular domain of human CD40 and intracytoplasmic domain of mouse CD40 (hmCD40) with either a mutation that prevents recruitment of TRAF2,3 (hmCD40 ΔT2,3) or TRAF6 (hmCD40 ΔT6). These cells were transfected with pGL4.32luc2P/NF-κB-RE/Hygro vector (Promega Corporation, Madison, WI) encoding an NF-κB response element that drives the luciferase reporter gene luc2P (*Photinus pyralis*). Cells were pre-incubated with peptides for 3 hr. followed by stimulation with human CD154. Luciferase activity was assessed using a Steady-Glo luciferase assay system (Promega Corporation) and a luminometer. The effects of peptides on cell viability were examined using alamarBlue cell viability assay.

Flow Cytometry

Cells were incubated with anti-ICAM-1 mAb (eBiosciences). After fixation with 1% paraformaldehyde, cells were analyzed using an LSR II (Becton Dickinson).

Statistical Analysis

D'Agostino & Pearson omnibus test was used to confirm normal distribution of the data. Data were analyzed by 2-tailed Student's t test or ANOVA. Differences were considered statistically significant at $P<0.05$.

Results

Figure 16:
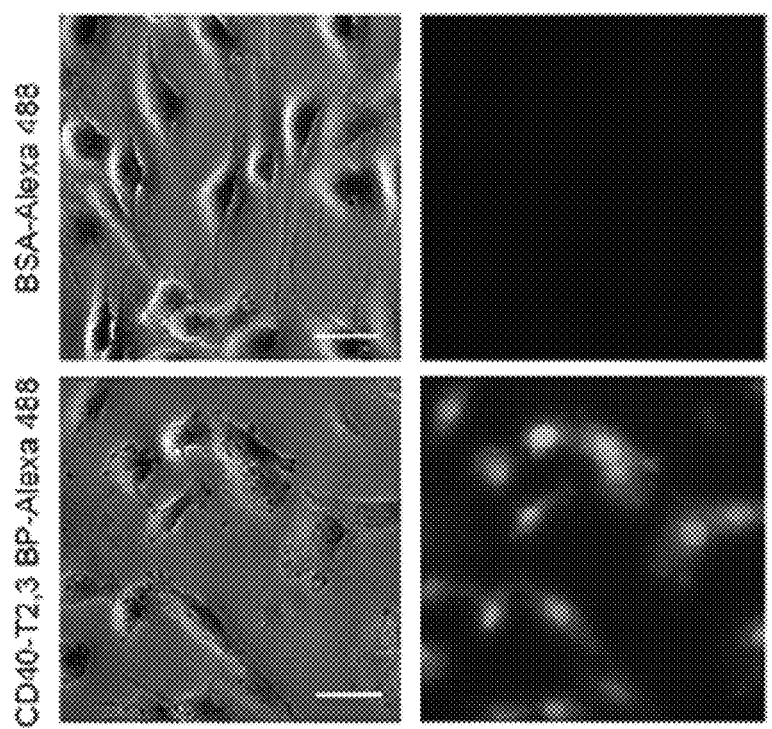
FIG. 16 illustrates an image showing ri CD40-TRAF2,3 blocking peptide penetrates cells. Human Müller cells were incubated in medium containing Alexa Fluor 488-conjugated ri CD40-TRAF2,3 blocking peptide or Alexa Fluor 488-conjugated albumin (both at 10 μM) for 3 h. Scale bar, 50 μm. Original magnification ×400. Images represent fluorescence of unfixed Müller cells after extensive washing of monolayers. Images are representative of 3 independent experiments.
Figure 17:
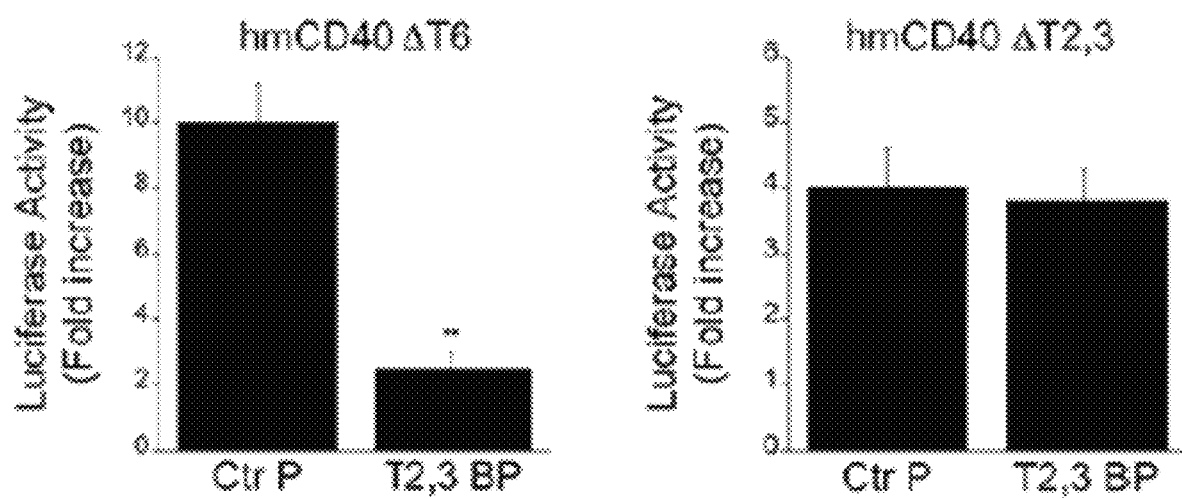
FIG. 17 illustrates graphs showing ri CD40-TRAF2,3 blocking peptide inhibits CD40-TRAF2,3 but not CD40-TRAF6 signaling. Mouse endothelial cells (mHEVc) that express an NF-κB response element that drives transcription of a luciferase reporter plus either hmCD40 ΔT2,3 or hmCD40 ΔT6 were pre-incubated with ri control peptide (Ctr P) or ri CD40-TRAF2,3 blocking peptide (T2,3 BP; both at 1 μM) or medium alone followed by stimulation with human CD154. Data are expressed as fold-increase in normalized luciferase activity in cells stimulated with CD154 compared to cells treated with respective peptide in the absence of CD154. Data shown represent Mean±SD. Results are representative of 2 independent experiments. **P<0.01.
Figure 18:
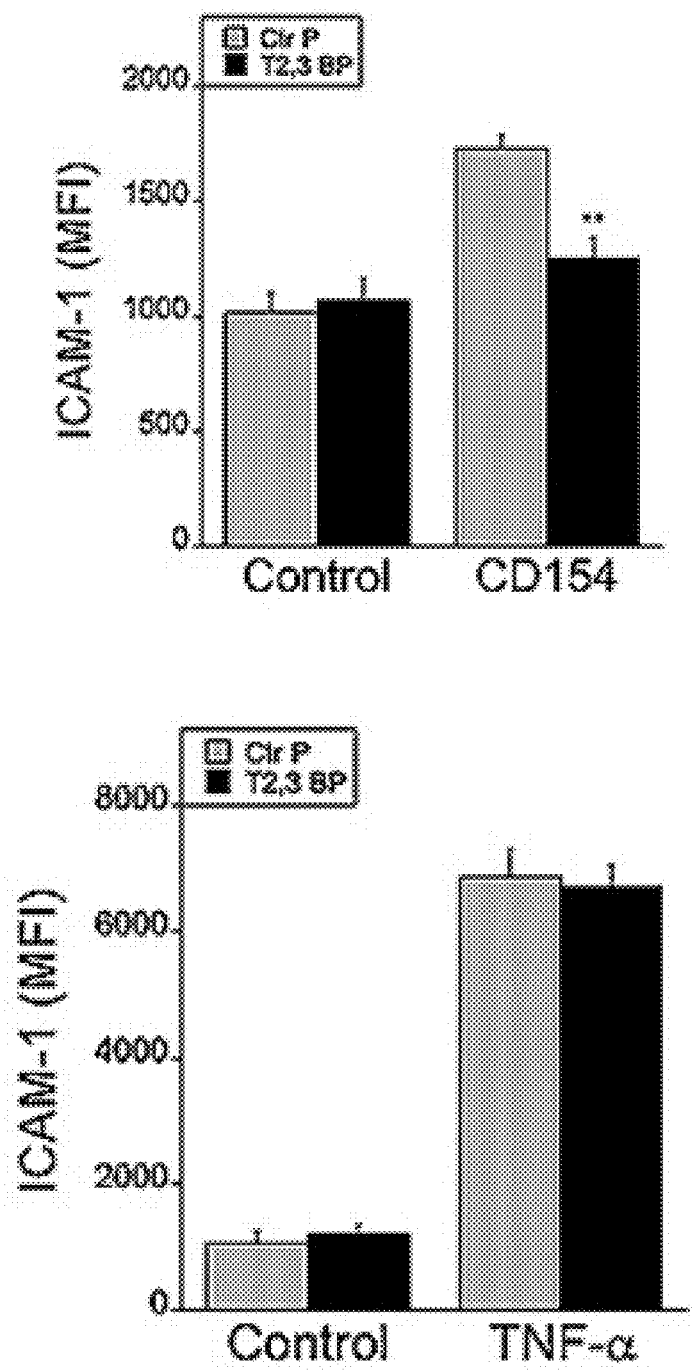
FIG. 18 illustrates graphs showing ri CD40-TRAF2,3 blocking peptide inhibits CD40-driven upregulation of ICAM-1. Human retinal endothelial cells were treated with ri control peptide (Ctr P) or ri CD40-TRAF2,3 blocking peptide (T2,3 BP; both at 1 μM) followed by stimulation with CD154 or TNF-α. Expression of ICAM-1 was assessed by flow cytometry at 24 h. Data shown represent Mean±SD. Results are representative of 2 independent experiments. **P<0.01.

Retro-Inverso (ri) CD40-TRAF2,3 Blocking Peptide Inhibits CD40-TRAF2,3 but not CD40-TRAF6 Signaling A ri version of the previously described $TAT_{47-57}$-based CD40-TRAF2,3 blocking peptide was generated. ri CD40-TRAF2,3 blocking peptide tagged with Alexa Fluor 488 was synthesized to determine whether it translocates inside cells. Using human Müller cells (the principal glia in the retina) as a model, immunofluorescence studies revealed intracellular incorporation of the fluorescent peptide after its addition to the culture medium (FIG. 16). Next, we examined whether the ri CD40-TRAF2,3 blocking peptide inhibited CD40-TRAF2,3 signaling. We used reporter cell lines that consisted of mouse endothelial cells expressing a human-mouse CD40 chimera (extracellular human CD40 and intracellular mouse CD40) that signaled either through the TRAF2,3 binding site (hmCD40 ΔT6) or the TRAF6 binding site (hmCD40 ΔT2,3). These cells expressed an NF-κB response element that drives a luciferase reporter gene. Reporter cells were incubated with ri control peptide or ri CD40-TRAF2,3 blocking peptide followed by stimulation with human CD154. The blocking peptide inhibited NF-κB activity only in cells that express CD40 that signals through the TRAF2,3 binding site (FIG. 17). Taken together, ri CD40-TRAF2,3 blocking peptide effectively impairs CD40-TRAF2,3 but not CD40-TRAF6 signaling.

ri CD40-TRAF2,3 Blocking Peptide Inhibits a CD40-Induced Pro-Inflammatory Response ICAM-1 upregulation in endothelial cells is a key event in the development of inflammatory disorders. We used CD40-induced upregulation of ICAM-1 in endothelial cells to determine if the ri CD40-TRAF2,3 blocking peptide impairs a pro-inflammatory response. Human retinal endothelial cells were incubated with control or blocking peptides followed by stimulation with CD154. ri CD40-TRAF2,3 blocking peptide impaired upregulation of ICAM-1 in response to CD154 (FIG. 18A). In contrast, the peptide had no effect on TNF-α-induced upregulation of ICAM-1 (FIG. 18B). Thus, ri CD40-TRAF2,3 blocking peptide inhibits a CD40-induced pro-inflammatory response.

Figure 19:
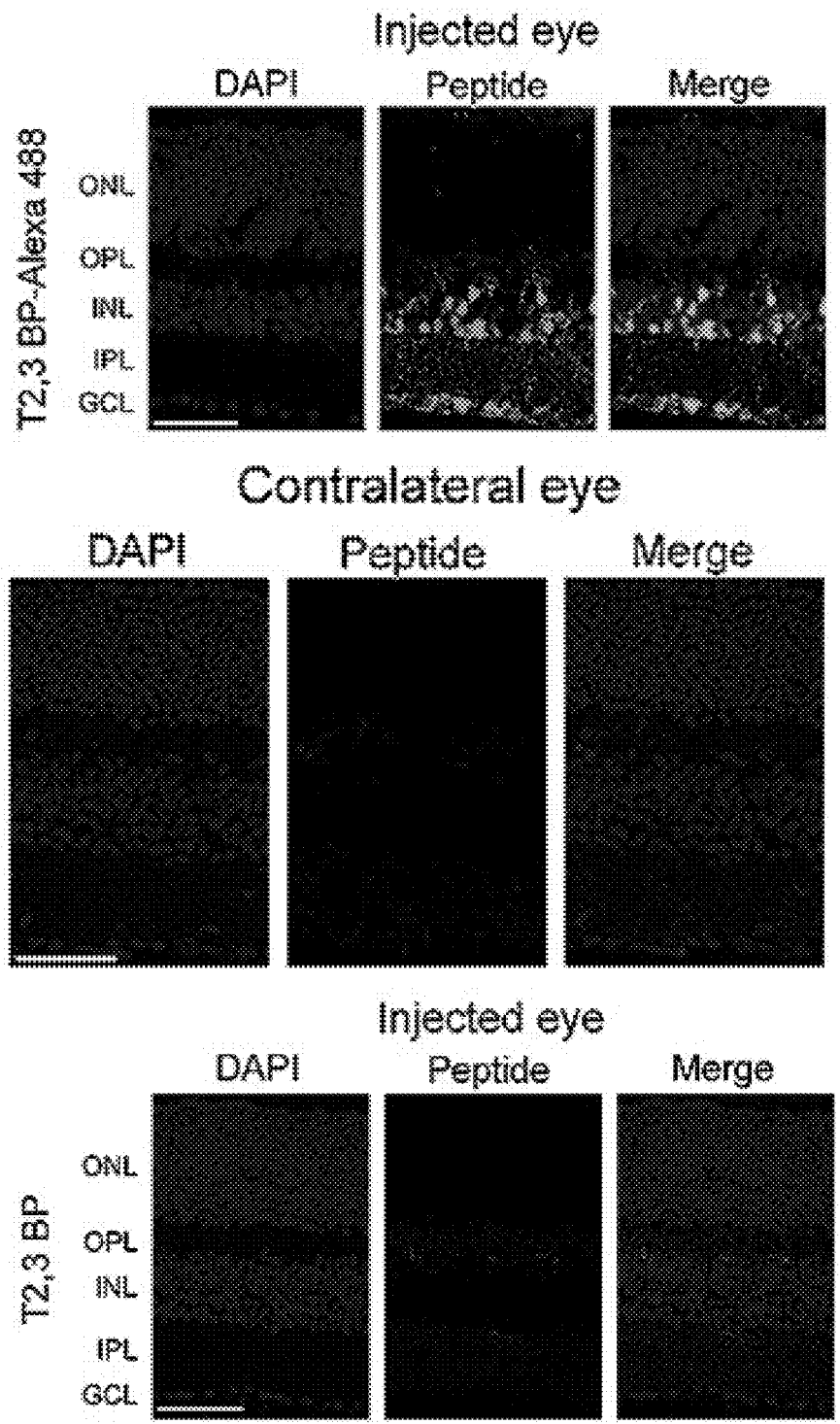
FIG. 19 illustrates images showing ri CD40-TRAF2,3 blocking peptide penetrates retinal cells. B6 mice received Alexa Fluor 488-conjugated ri CD40-TRAF2,3 blocking peptide or non-fluorescent ri CD40-TRAF2,3 blocking peptide (both 1 μg) via intravitreal injection of one eye. Injected and contralateral eyes were collected after 48 h and frozen sections were examined. GCL=Ganglion cell layer; IPL=Inner plexiform layer; INL=Inner nuclear layer. OPL=Outer plexiform layer; ONL=Outer nuclear layer. Scale bar, 50 μm. Original magnification ×400. Results are representative of 3 independent experiments.

Intravitreal Administration of ri CD40-TRAF2,3 Blocking Peptide Prior to I/R Protects Against Neuronal Cell Loss and Leukocyte Infiltration in a Manner Similar to that Observed in $CD40^{-/-}$ Mice To begin to test the in vivo effect of ri CD40-TRAF2,3 blocking peptide, we examined whether it translocates into retinal cells. Alexa Fluor 488-conjugated ri CD40-TRAF2,3 blocking peptide or non-fluorescent peptide were injected intravitreally and eyes were collected after 2 days. FIG. 19 shows uptake of fluorescent peptide that tended to localize in the inner retina, especially in nuclei located in this region. This is consistent with the pattern of nuclear accumulation reported for TAT. As described for other TAT-based cell penetrating peptides, the ri CD40-TRAF2,3 blocking peptide did not cause retinal pathology in the injected eye and was not detected in the contralateral eye (FIG. 19).

Figure 20A:
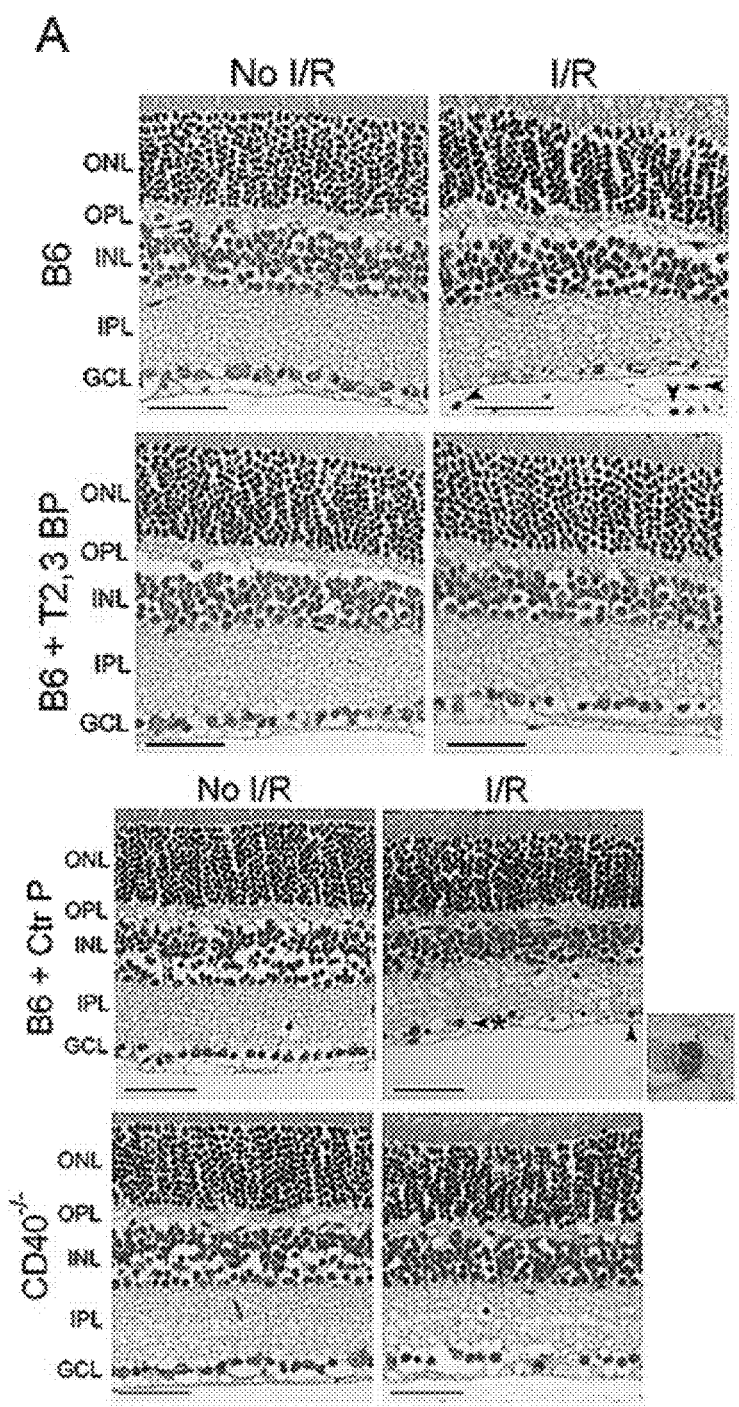
FIGS. 20(A-C) illustrate images and graphs showing ri CD40-TRAF2,3 blocking peptide protects against loss of ganglion cells and leukocyte infiltration in retinas subjected to I/R. One eye from each B6 and CD40$^{-/-}$ mouse was subjected to I/R. Contralateral non-ischemic eye was used as control. Eyes subjected to I/R in B6 mice were treated intravitreously with or without ri control peptide, ri CD40-TRAF2,3 blocking peptide (both 1 μg) 30 min prior to increase in IOP. Eyes were collected 2 d after I/R. A marked decrease in the number of ganglion cells is observed in ischemic eyes from B6 treated with ri control peptide or vehicle (original magnification ×400). Eyes from these mice also exhibited PMN infiltration in the inner retina and vitreous (arrowhead). Arrowhead plus asterix identifies a PMN magnified in the inset (original magnification ×600). Scale bar, 50 μm. Number of ganglion cells per mm. Number of infiltrating leukocytes in the inner retina and vitreous per section. GCL=Ganglion cell layer; IPL=Inner plexiform layer; INL=Inner nuclear layer. OPL=Outer plexiform layer.
Figure 20B:
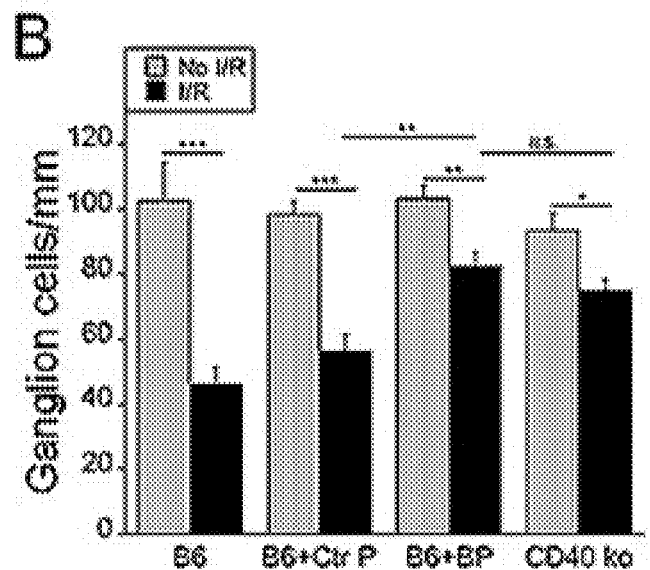
Figure 20C:
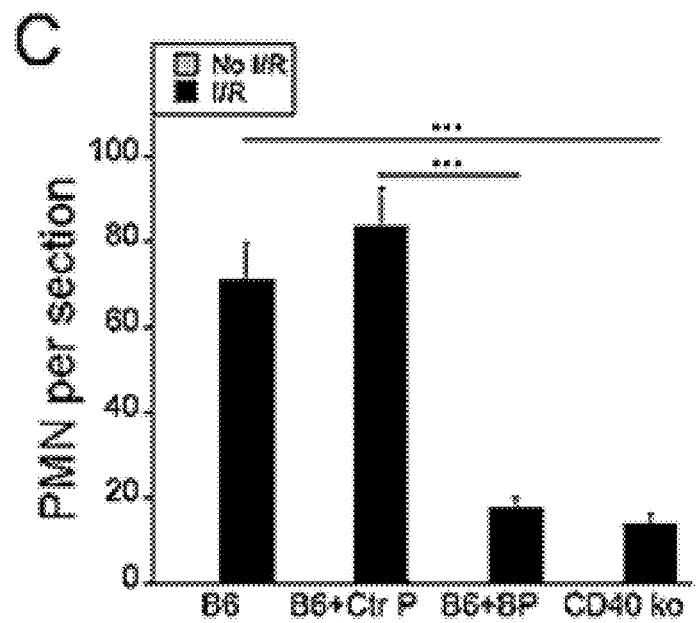

Next, we examined the in vivo effects of the ri CD40-TRAF2,3 blocking peptide using a model of I/R-induced retinal injury based on transient elevation of IOP. I/R of the retina causes loss of neurons (ganglion cells). Compared to contralateral non-ischemic eyes in B6 mice, eyes subjected to I/R developed a marked reduction in ganglion cells (FIGS. 20A, B). This effect was not altered by intravitreal injection of control peptide 1 h prior to retinal ischemia (FIGS. 20A, B). In contrast, eyes of B6 mice treated with ri CD40-TRAF2,3 blocking peptide and subjected to I/R exhibited a significant attenuation in the loss of ganglion cells. The protective effect of the blocking peptide was similar to that conferred by the lack of CD40 ($CD40^{-/-}$ mice) (FIGS. 20A, B).

Polymorphonuclear leukocytes (PMNs) infiltrate the retina in the early stages after I/R, a response that is considered central to the pathogenesis of neuronal loss after retinal I/R. Eyes from B6 mice treated with the control peptide developed PMN infiltration in the inner retina and vitreous (FIGS. 20A, C). In contrast, ischemic eyes from B6 mice treated with ri CD40-TRAF2,3 blocking peptide exhibited diminished inflammatory infiltrate, an effect that was similar to that observed in $CD40^{-/-}$ mice subjected to I/R (FIGS. 20A, C). Taken together, the ri CD40-TRAF2,3 blocking peptide effectively protects against I/R-induced neuronal cell loss and PMN infiltration.

Intravitreal Administration of ri CD40-TRAF2,3 Blocking Peptide Impairs I/R-Induced Upregulation of NOS2 and COX-2

PMN recruited after ischemia are known to express NOS2 and COX-2. Moreover, retinopathy induced by I/R causes upregulation of NOS2 and COX-2, molecules that are linked to the development of neuronal cell loss. Compared to contralateral non-ischemic eyes, eyes treated with the control peptide and subjected to I/R upregulated NOS2 and COX-2 mRNA levels (FIG. 21). Consequent with the reduction in PMN recruitment, eyes from B6 mice treated with ri CD40-TRAF2,3 blocking peptide exhibited impaired upregulation of NOS2 and COX-2, an effect that was similar to that observed in $CD40^{-/-}$ mice subjected to retinal I/R (FIG. 21).

Figure 22A:
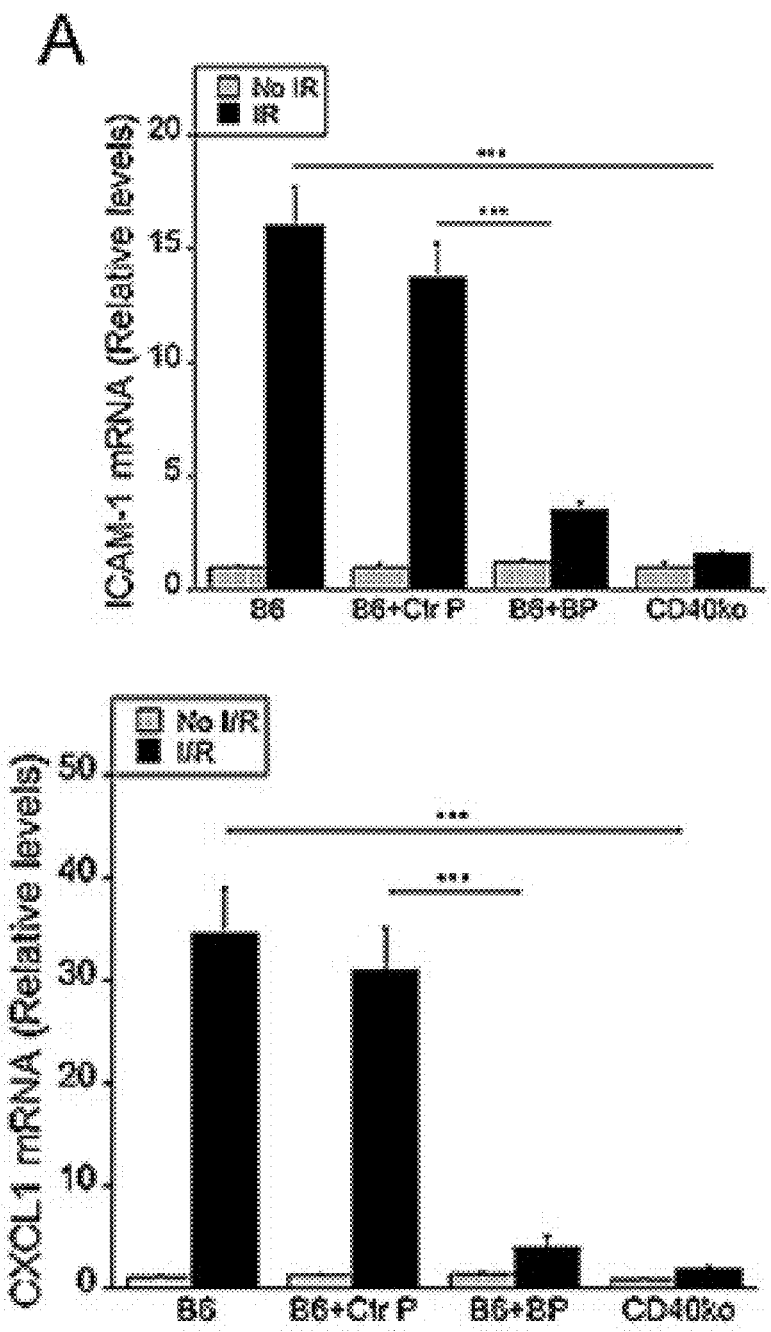
Figure 22B:
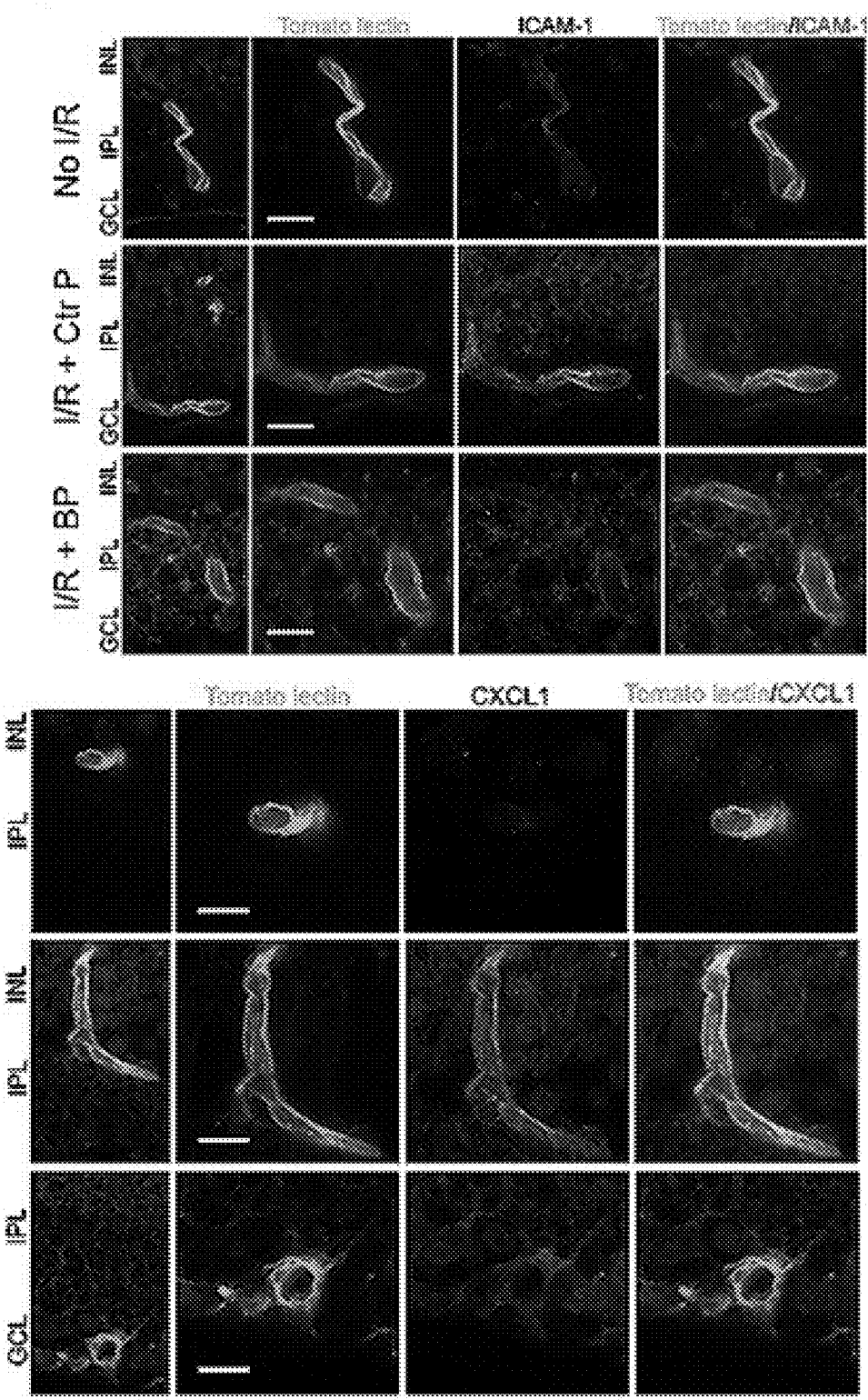

Intravitreal Administration of ri CD40-TRAF2,3 Blocking Peptide Impairs I/R-Induced ICAM-1 and KC/CXCL1 Upregulation in Retinal Endothelial Cells We examined the expression of ICAM-1 and KC/CXCL1, molecules that are central to PMN recruitment and that are upregulated after retinal I/R. Retinas subjected to I/R from B6 mice that received the control peptide showed marked upregulation of ICAM-1 and KC/CXCL1 mRNA levels (FIG. 22A). Administration of ri CD40-TRAF2,3 blocking peptide caused a significant reduction in ICAM-1 and KC/CXCL1 mRNA levels that was similar to that observed in the retinas of CD40$^{-/-}$ mice subjected to I/R (FIG. 22A). Next, we examined expression of these inflammatory molecules in retinal endothelial cells. Expression of ICAM-1 and KC/CXCL1 were increased in retinal endothelial cells from mice that received control peptide (FIG. 22B). In agreement with mRNA data, mice treated with the ri CD40-TRAF2,3 blocking peptide had decreased expression of these molecules in retinal endothelial cells (FIG. 22B). Thus, the ri CD40-TRAF2,3 blocking peptide protected against I/R-induced upregulation of ICAM-1 and KC/CXCL1 in retinal endothelial cells.

Intravitreal Administration of ri CD40-TRAF2,3 Blocking Peptide Impairs I/R-Induced KC/CXCL1 and NOS2 Upregulation in Müller Cells Retinal Müller cells play an important role in the development of inflammatory responses in the retina. Moreover, it has been suggested that Müller cells upregulate NOS2 after retinal ischemia. Immunohistochemistry studies revealed NOS2 upregulation in Müller cells from retinas subjected to I/R and treated with the control peptide (FIG. 23A). Moreover, Müller cells from these retinas also exhibited increased KC/CXCL1 expression (FIG. 23B). Treatment with ri CD40-TRAF2,3 blocking peptide impaired expression of these molecules in Müller cells from retinas subjected to I/R (FIG. 23A, B). Altogether, Müller cells from ischemic retinas upregulate NOS2 and KC/CXCL1, an effect that is impaired by the ri CD40-TRAF2,3 blocking peptide.

Intravitreal Administration of ri CD40-TRAF2,3 Blocking Peptide After I/R Protects Against Ganglion Neuron Loss and Retinal Inflammatory Responses Control or ri CD40-TRAF2,3 blocking peptide were administered 90 min post-retinal ischemia. As shown in FIG. 24, the blocking peptide protected against ganglion cell loss, leukocyte recruitment, and upregulation of ICAM-1, KC/CXCL1, NOS2 and COX-2. Thus, ri CD40-TRAF2,3 blocking peptide is effective in ameliorating the development of inflammation and neuronal loss even if administered after induction of retinal ischemia.

Studies in mice indicate that CD40 is a molecular target for treatment of various inflammatory and neuro-degenerative disorders. However, there is a need to find therapeutic approaches to inhibit CD40 signaling in humans since administration of neutralizing anti-CD154 mAbs, the approach used to block CD40 in mice, was found to be problematic due to the development of thrombo-embolic events. Moreover, generalized inhibition of CD40 signaling or inhibition of CD40-TRAF6 signaling are expected to lead to increased risk of infections caused by pathogens controlled by cell-mediated immunity. We show that inflammation can be controlled by pharmacologic inhibition of CD40-TRAF2,3 signaling, a pathway that does not mediate cellular responses key to cell-mediated immunity.

Using a model of retinal I/R, we show that a ri cell-penetrating CD40-TRAF2,3 blocking peptide markedly diminishes ICAM-1 and KC/CXCL1 upregulation and reduces PMN infiltration yielding a phenotype similar to that observed in CD40$^{-/-}$ mice subjected to retinal I/R. The in vivo effects of the ri blocking peptide correlate with the in vitro studies showing that CD40-TRAF2,3 signaling is crucial for adhesion molecule and chemokine upregulation in a broad range of cells. In addition, given that infiltrating PMN express NOS2 and COX-2, the reduction in PMN recruitment likely contributes to the effect of the CD40-TRAF2,3 blocking peptide in ameliorating the upregulation of NOS2 and COX-2. These molecules are linked to neural cell death and administration of NOS2 or COX-2 inhibitors reduces retinal pathology after I/R. Taken together, these results indicate that CD40-TRAF2,3 signaling is an important mediator of inflammation and neurodegeneration following ischemia. Importantly, pharmacologic inhibition of CD40-TRAF2,3 after ischemia protected against inflammation and achieved neuro-protection.

CD40 is an important driver of inflammation and pathology not only in retinal ischemia but also in ischemic stroke as well as pulmonary, liver and kidney I/R, conditions relevant to organ injury following cardiopulmonary by-pass and organ transplantation Like in the retina, ischemia in these organs leads to CD40-driven upregulation of chemokines and adhesion molecules, promoting leukocyte recruitment and tissue injury. While recruitment of leukocyte subsets such as macrophages, microglia and lymphocytes can play either a detrimental or a protective role after cerebral ischemia, several studies support the deleterious role of infiltrating PMN. Indeed, PMNs can be key mediators of injury after I/R and blockade of ICAM-1 or KC/CXCL1 protects against inflammation and organ injury after I/R. While it remains to be determined whether approaches to impair inflammatory responses can yield beneficial effects in patients with ischemic stroke, strategies that target adhesion molecules or chemokines have been found to be effective against other inflammatory disorders. The fundamental role of adhesion molecule and chemokine upregulation in inflammatory disorders supports that pharmacologic blockade of CD40-TRAF2,3 will likely control CD40-driven inflammatory disorders besides those triggered by ischemia.

Müller cells acquire expression of pro-inflammatory molecules that likely contribute to the pathogenesis of retinopathies. Studies in humans and animals suggested that Müller cells acquire NOS2 expression in ischemic and diabetic retinopathies. The present work indicates that indeed Müller cells express not only NOS2 is but also KC/CXCL1 in the ischemic retina. Moreover, pharmacologic inhibition of the CD40-TRAF2,3 pathway reduces expression of these molecules in Müller cells suggesting that this pathway also operates in Müller cells to drive responses believed to promote tissue injury. Of relevance, in vitro studies in Müller cells that express CD40 with mutations in CD40-TRAF2,3 binding site or Müller cells treated with a CD40-TRAF2,3 blocking peptide revealed that the CD40-TRAF2,3 pathway is a major inducer of pro-inflammatory responses in Müller cells.

The need to find novel approaches to treat CD40-driven inflammatory disorders together with the central role of TRAFs as mediators of the effects of CD40 stress the importance of examining inhibition of CD40-TRAF signaling for potential therapeutic application. Prior studies centered on the effects of inhibition of CD40-TRAF6 signaling in hematopoietic cells. Our studies uncovered that CD40-TRAF2,3 signaling is critical to development of inflammation and neuronal cell loss. This finding is important because inhibition of CD40-TRAF2,3 signaling is expected to be accompanied by a reduced risk of infections compared to general inhibition of CD40 signaling or inhibition of CD40-TRAF6 signaling. While all these approaches are expected to impair antibody production, in contrast to inhibition of CD40 or CD40-TRAF6 signaling, blockade of the CD40-TRAF2,3 pathway would leave largely intact various aspects of cell-mediated immunity central to resistance against opportunistic pathogens.

Cell-penetrating peptides have been used in studies that address fundamental biology questions, in pre-clinical therapeutic studies and have also resulted in clinical trials. Given that $TAT_{47-57}$-based CD40-TRAF2,3 blocking peptide inhibits CD40-TRAF2,3 signaling and CD40-dependent inflammatory responses in vitro, we generated a ri peptide as an initial pharmacologic approach to block CD40-TRAF2,3 signaling in vivo. Intravitreal administration of this peptide may become an attractive approach for the treatment of ocular disorders (e.g., ischemic retinopathies, diabetic retinopathy and perhaps glaucoma) since $TAT_{47-57}$-based ri cell-penetrating peptides are good tools for transporting molecules into retinal cells and they appear to persist in the retina for at least 14 d after a single intravitreal injection.

In summary, this Example shows pharmacologic inhibition of the CD40-TRAF2,3 pathway as a novel approach to control CD40-driven inflammation. This work shows therapeutic approaches to treat CD40-driven inflammatory disorders based on pharmacologic blockade of CD40-TRAF2,3 signaling either by administration of a CD40-TRAF2,3 blocking peptide or a small molecule inhibitor of CD40-TRAF2,3 signaling. This approach is likely to be effective in a broad range of CD40-mediated diseases given that blockade of this pathway restricts fundamental pro-inflammatory responses.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A composition comprising:
a cell-permeable polypeptide that competitively inhibits binding of TRAF2 to the TRAF2,3 binding domain of CD40 of cells, the cell-permeable polypeptide comprising a membrane transduction domain and a retro-inverso peptide of a CD40-TRAF2,3 blocking peptide comprising the amino acid sequence that is at least 70% identical to SEQ ID NO: 10.

2. The composition of claim 1, the CD40-TRAF2,3 blocking peptide having an amino acid sequence selected from SEQ ID NO: 29, SEQ ID NO: 30, SEQ ID NO: 31, SEQ ID NO: 32, SEQ ID NO: 33: SEQ ID NO: 34, or SEQ ID NO: 35.

3. The composition of claim 1, the retro-inverso CD40-TRAF2,3 blocking peptide having an amino acid sequence selected from SEQ ID NO: 39, SEQ ID NO: 40, SEQ ID NO: 41, SEQ ID NO: 42, SEQ ID NO: 43: SEQ ID NO: 44, or SEQ ID NO: 45.

4. The composition of claim 1, the cell-permeable polypeptide comprising a membrane transduction domain, the cell-permeable polypeptide consisting essentially of SEQ ID NO: 12 or SEQ ID NO: 13.

5. The composition of claim 1, wherein the cell-permeable polypeptide has an amino acid sequence selected from SEQ ID NO: 46, SEQ ID NO: 47, SEQ ID NO: 48, or SEQ ID NO: 49.

6. The composition of claim 1, further comprising a pharmaceutically acceptable carrier.

* * * * *